United States Patent
Kumar et al.

(10) Patent No.: US 12,378,587 B2
(45) Date of Patent: Aug. 5, 2025

(54) RECOMBINANT METHANOTROPHIC BACTERIA FOR INDIGO BIOSYNTHESIS AND METHODS THEREOF

(71) Applicant: STRING BIO PRIVATE LIMITED, Karnataka (IN)

(72) Inventors: Rajeev S. Kumar, Karnataka (IN); Vinita Lukose, Karnataka (IN); Shruthi S, Karnataka (IN); Ezhilkani Subbian, Karnataka (IN); Shirish Gajanan Gole, Karnataka (IN); Deepika Singh, Karnataka (IN)

(73) Assignee: String Bio Private Limited, Karnataka (IN)

( * ) Notice: Subject to any disclaimer, the term of this patent is extended or adjusted under 35 U.S.C. 154(b) by 630 days.

(21) Appl. No.: 17/632,363

(22) PCT Filed: Aug. 3, 2020

(86) PCT No.: PCT/IB2020/057323
§ 371 (c)(1),
(2) Date: Feb. 2, 2022

(87) PCT Pub. No.: WO2021/024160
PCT Pub. Date: Feb. 11, 2021

(65) Prior Publication Data
US 2022/0411837 A1    Dec. 29, 2022

(30) Foreign Application Priority Data
Aug. 2, 2019 (IN) .............. 201941031391

(51) Int. Cl.
C12N 15/52 (2006.01)
C12N 1/20 (2006.01)
C12N 1/32 (2006.01)
C12P 17/16 (2006.01)

(52) U.S. Cl.
CPC .............. *C12P 17/165* (2013.01); *C12N 1/20* (2013.01); *C12N 1/32* (2013.01); *C12N 15/52* (2013.01); *C12Y 114/13008* (2013.01); *C12Y 401/99001* (2013.01); *C12Y 402/0102* (2013.01)

(58) Field of Classification Search
CPC ... C12N 1/20; C12N 1/32; C12N 9/88; C12Y 401/99001
See application file for complete search history.

(56) References Cited

U.S. PATENT DOCUMENTS

2022/0411837 A1* 12/2022 Kumar .................... C12N 1/32

OTHER PUBLICATIONS

Berry et al., "Application of metabolic engineering to improve both the production and use of biotech indigo" Journal of Industrial Microbiology & Biotechnology, 2002, 28:127-133.
Database: NCBI, Title: 3-deoxy-7-phosphoheptulonate synthase AroG [Methylococcus capsulatus] [NCBI Reference Sequence: WP_010960376.1] Jun. 20, 2019, 1 pages.
Database: NCBI, Title: Acyl-CoA dehydrogenase-like protein [Acinetobacter baumannii ATCC 17978] [GenBank: ABO12291.2] Jan. 31, 2014, 2 pages.
Database: NCBI, Title: flavin-containing monooxygenase FMO [Expression vector pTMH406] [GenBank: AUO17141.1], Jan. 22, 2018, 1 page.
Database: NCBI, Title: putative SocE suppressor [*Myxobacter* sp. HK1] [GenBank: AAX51947.1] Mar. 27, 2005, 1 pages.
Diaz et al., "Bioengineering Strategies for Protein-Based Nanoparticles." Genes, 2018, 9(7):370.
Han et al., "Optimization of bio-indigo production by recombinant *E. coli* harboring fmo gene," Enzyme and Microbial Technology, 2008, 42(7):617-623.
International Search Report in International Application No. PCT/IB2020/057323, dated Nov. 27, 2020, 12 pages.
International Preiliminary Report on Patentability in International Application No. PCT/IB2020/057323, dated Feb. 8, 2022, 8 pages.
Li and Young, "A new suite of tnaA mutants suggests that *Escherichia coli* tryptophanase is regulated by intracellular sequestration and by occlusion of its active site" BMC Microbiology, 2015, 15:14.
Ma et al., "Biodegradation and Biotransformation of Indole: Advances and Perspectives" Frontiers in microbiology, 2018, 9(2625):1-18.
Mitchell, "Genetic Fusions Defining trp and lac operon Regulatory Elements" Journal of Molecular Biology, 1975, 93(3):331-350.
Boya et al., "Diversity of the Tryptophanase Gene and Its Evolutionary Implications in Living Organisms," Microorganisms, Oct. 15, 2021, 9:2156, 24 pages.
Chen et al., "Bacterial flavin-contained monooxygenase is trimethy lamine monooxygenase," PNAS, Oct. 25, 2011, 108(43):17791-17796.
Crawford, "Nucleotide Sequence of the trpB Gene in *Escherichia coli* and *Salmonella typhimurium*," Journal of Molecular Biology, 1980, 142:486-502.

* cited by examiner

*Primary Examiner* — Tekchand Saidha
(74) *Attorney, Agent, or Firm* — Fish & Richardson P.C.

(57) ABSTRACT

The instant disclosure is in the field of biosciences, more particularly towards molecular and industrial biotechnology. The present disclosure relates to recombinant methanotrophic bacteria capable of synthesizing indigo from methane comprising a gene encoding enzyme for increasing concentration of indole and a gene encoding enzyme for converting the indole to indoxyl. The present disclosure also relates to a method of developing the recombinant methanotrophic bacteria, and a method of indigo biosynthesis by the recombinant methanotrophic bacteria in presence of a methane source.

17 Claims, 6 Drawing Sheets
Specification includes a Sequence Listing.

RECOMBINANT METHANOTROPHIC BACTERIA FOR INDIGO BIOSYNTHESIS AND METHODS THEREOF

CROSS REFERENCE OF RELATED APPLICATIONS

This application is a U.S. National Phase application under 35 U.S.C. § 371 of International Patent Application No. PCT/IB2020/057323, filed on Aug. 3, 2020, which claims the priority of Indian patent application Ser. No. 20/194,1031391, filed on Aug. 2, 2019, the disclosure of which is incorporated herein by reference in its entirety.

SEQUENCE LISTING

This application contains a Sequence Listing that has been submitted electronically as an ASCII text file named 53690-0002US1SequenceListing.txt. The ASCII text file, created on Feb. 2, 2022 is 120 kilobytes in size. The material in the ASCII text file is incorporated by reference in its entirety.

TECHNICAL FIELD

The instant disclosure is in the field of biosciences, more particularly towards molecular and industrial biotechnology. The present disclosure relates to recombinant methanotrophic bacteria, a method of developing said recombinant methanotrophic bacteria, and methods and applications related to indigo biosynthesis by the recombinant methanotrophic bacteria.

BACKGROUND OF THE DISCLOSURE

Indigo and its derivative pigments are considered to be one of the oldest classes of dyes known to man and extensively used in the textile industry. Indigo has been prized since antiquity for its vibrancy and deep blue color. India was the leading producer of natural indigo until the chemical synthesis took over the market. Until 2011, about 50,000 tons of indigo has been synthesized per year, of which 95% is used to dye over 4 billion denim garments. Indigo is also used as a food colorant and in the cosmetic industry.

While there is a high and unprecedented demand for indigo, such a demand presents serious environmental concerns mainly because of two important reasons. First, industrial scale indigo synthesis (chemical/synthetic route) relies on aniline, a by-product derived from the petroleum product benzene. Further, the chemical synthesis involves use of hazardous chemicals like formaldehyde, hydrogen cyanide, and strong bases. Second, as indigo is insoluble in water, it is reduced to the water-soluble form by using hazardous reducing agents. Sodium dithionite is the widely used reducing agent in industries because of its low cost and short reduction time. Said reducing agent and its derivatives are major pollutants of effluents from textile industries and subsequently have hazardous influences on public health.

Indigo is thus majorly produced by chemical synthesis and said synthetic counterparts have replaced the natural production. However, due to the industrial importance of indigo and the drawbacks of chemical synthesis as discussed above, there exists a need to provide a scalable, cost-effective, biological and ecofriendly route for indigo synthesis. The present disclosure addresses said need.

SUMMARY OF THE DISCLOSURE

The present disclosure relates to a recombinant methanotrophic bacterium capable of producing indigo from methane, comprising:
a gene encoding enzyme for increasing concentration of indole; and
a gene encoding enzyme for converting the indole to indoxyl,
wherein the concentration of indole is increased by:
a) conversion of tryptophan to indole, or
b) reducing or preventing formation of tryptophan from indole, or both a) and b).

In some embodiments, the gene encoding enzyme for increasing concentration of indole is a gene encoding tryptophanase (TnaA), or a gene encoding mutant beta subunit of tryptophan synthase (mutant TrpB), or a combination thereof. In some embodiments, the conversion of tryptophan to indole is facilitated by TnaA, and the mutant TrpB reduces or prevents tryptophan formation from indole thereby enhancing accumulation of indole.

In some embodiments, the gene encoding enzyme for converting the indole to indoxyl is a gene encoding an oxidase or dehydrogenase. In some embodiments, the oxidase is an indole oxidase. In some embodiments, the indole oxidase is flavin-containing monooxygenase (FMO).

In some embodiments, the dehydrogenase is acyl-CoA dehydrogenase-like protein (IacA), or a combination thereof. In some embodiments, the gene encoding enzyme for converting the indole to indoxyl is a gene encoding FMO or a gene encoding IacA, or a combination thereof.

In some embodiments, the recombinant methanotrophic bacterium comprises an overexpressed gene DAHP Synthase, AroF, AroB, AroD, AroE, AroK, AroA, AroC, and combinations thereof; a knocked-down gene selected from the group consisting of tryptophan operon regulator, tyrosine aminotransferase, aspartate aminotransferase and combinations thereof.

The present method also describes a method for developing the recombinant methanotrophic bacterium as described above, comprising engineering a wild-type methanotrophic bacterium with one or more genes as defined above to obtain the recombinant methanotrophic bacterium.

The present disclosure further describes a process for producing indigo from methane, comprising culturing the recombinant methanotrophic bacterium as described above, in presence of a methane source.

In some embodiments, the culturing of the recombinant methanotrophic bacterium is carried out at a temperature ranging from about 30° C. to 50° C., a pH ranging from about 3 to 8, and for a time-period ranging from 24 hours to 240 hours, and the culturing mode is selected from the group consisting of batch, fed batch, continuous process and combinations thereof.

The present disclosure further provides use of the recombinant methanotrophic bacterium as described above for production of indigo.

DESCRIPTION OF THE DISCLOSURE

Figure 1:
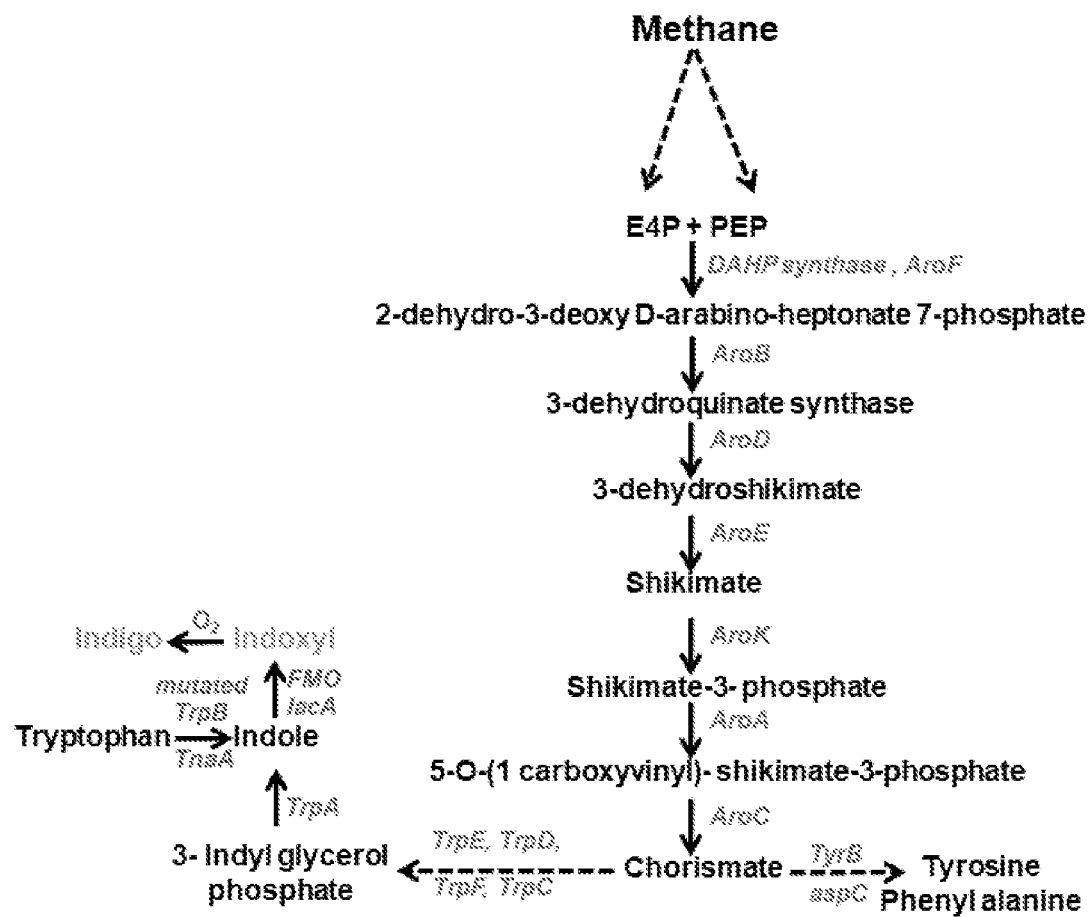
FIG. 1 depicts a flow-chart of the present disclosure indicating conversion of methane to indigo in recombinant methanotrophic bacteria via shikimic acid pathway.
Figure 2:
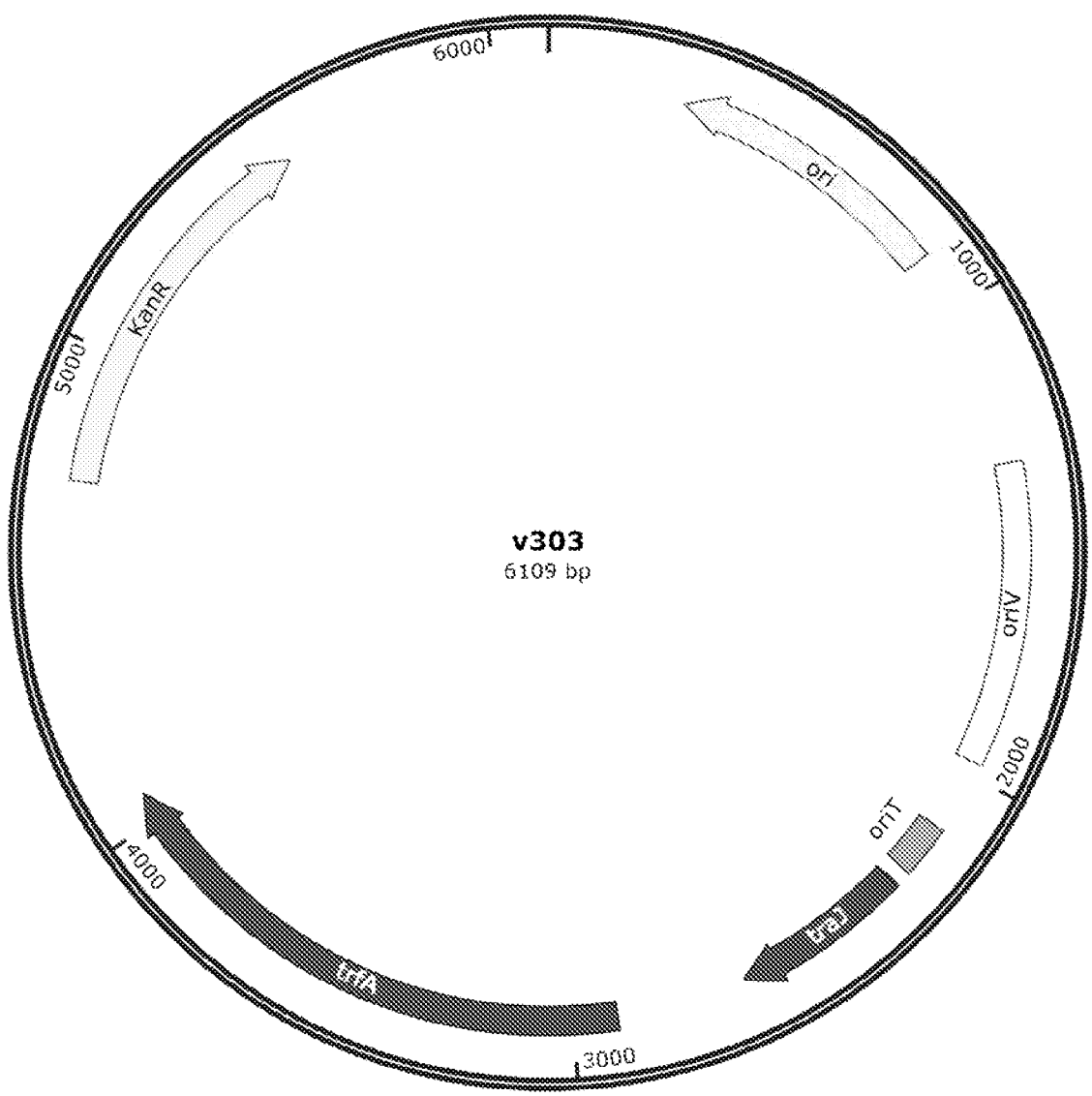
FIG. 2 illustrates the shuttle vector backbone for gene overexpression of tryptophanase or oxygenase or a combination thereof, for expression in methanotrophic bacteria.
Figure 3:
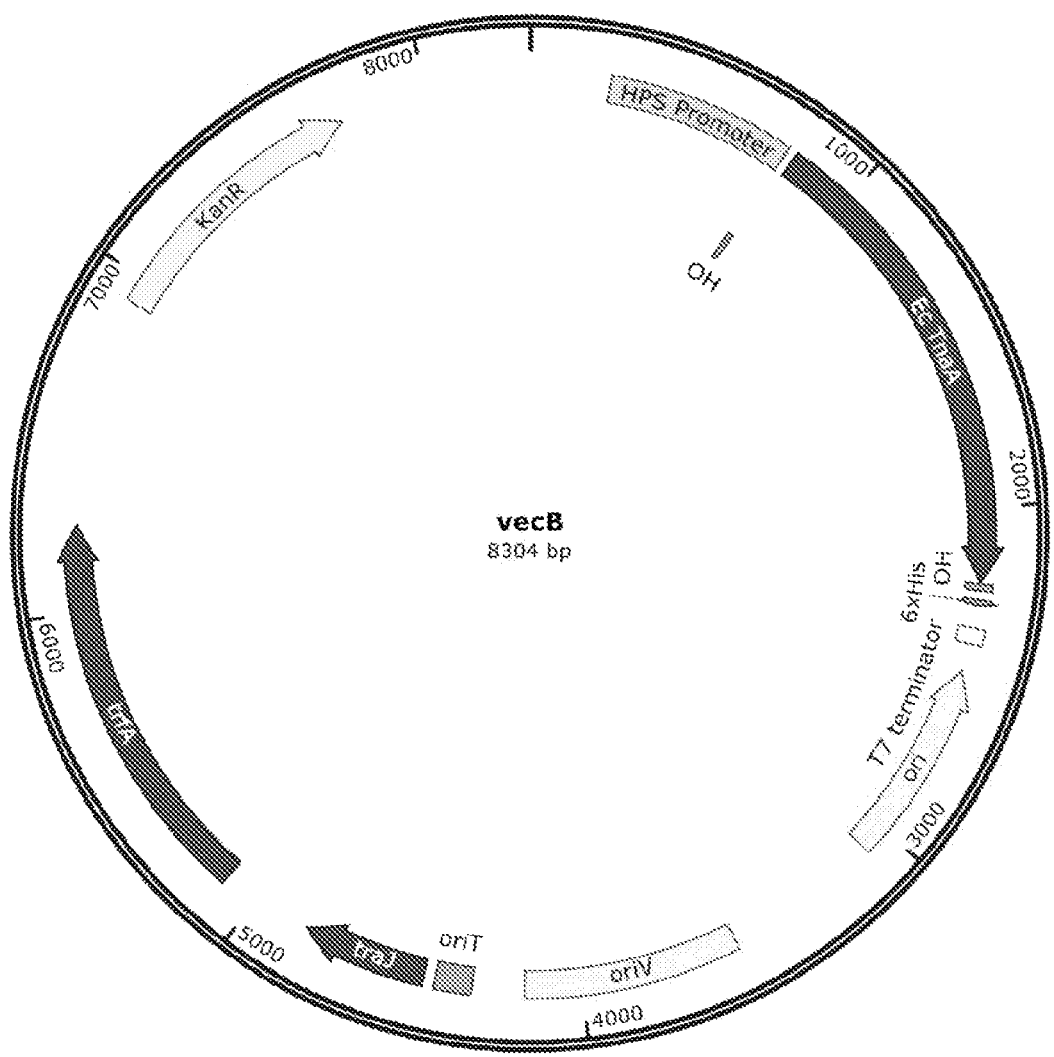
FIG. 3 illustrates a shuttle vector for overexpression of tryptophanase gene from *Escherichia coli* strain XL1-Blue from hps promoter in methanotrophic bacteria.
Figure 4:
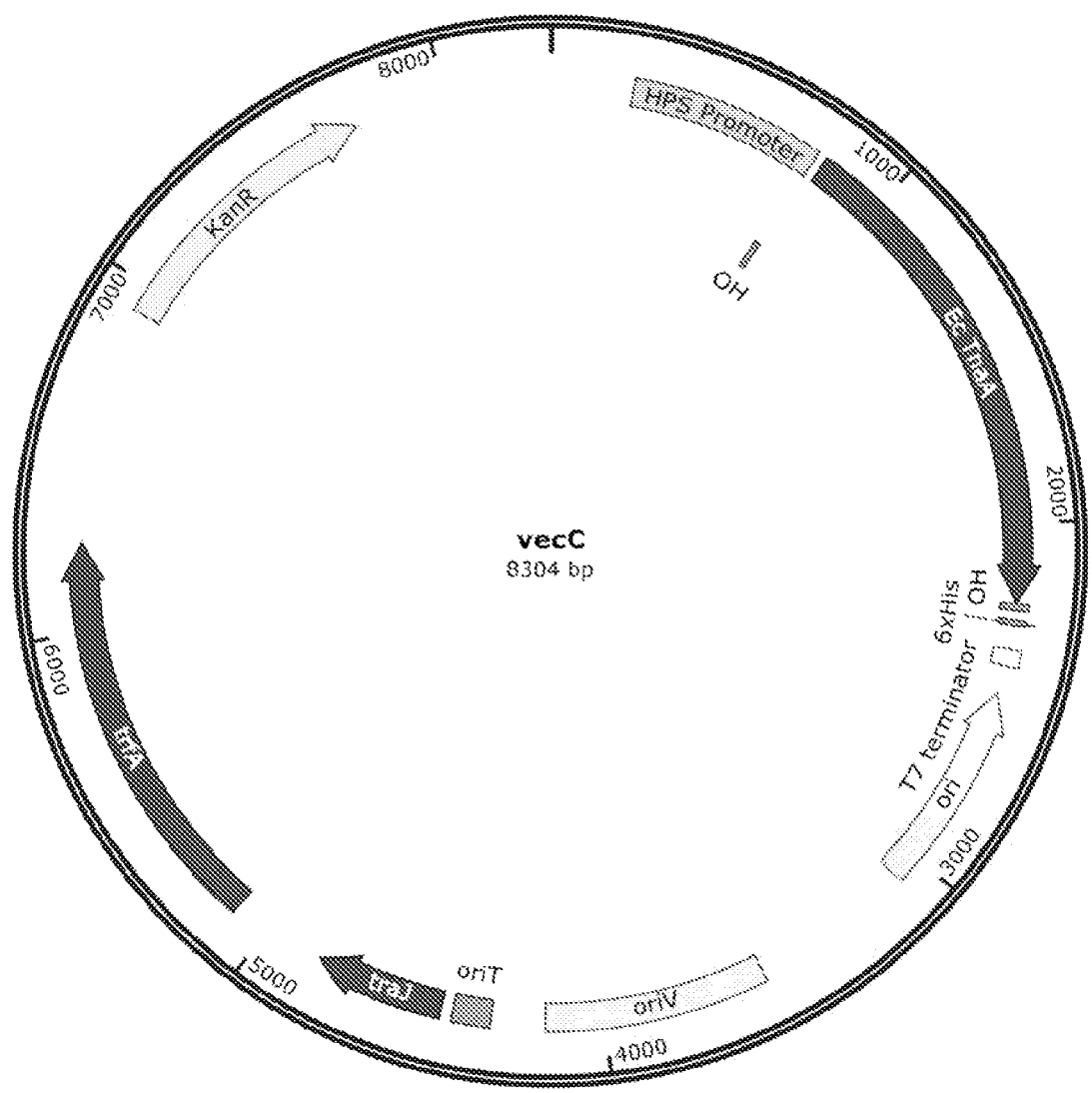
FIG. 4 illustrates a shuttle vector for overexpression of tryptophanase gene from *Escherichia coli* strain S17-1 from hps promoter in methanotrophic bacteria.
Figure 5:
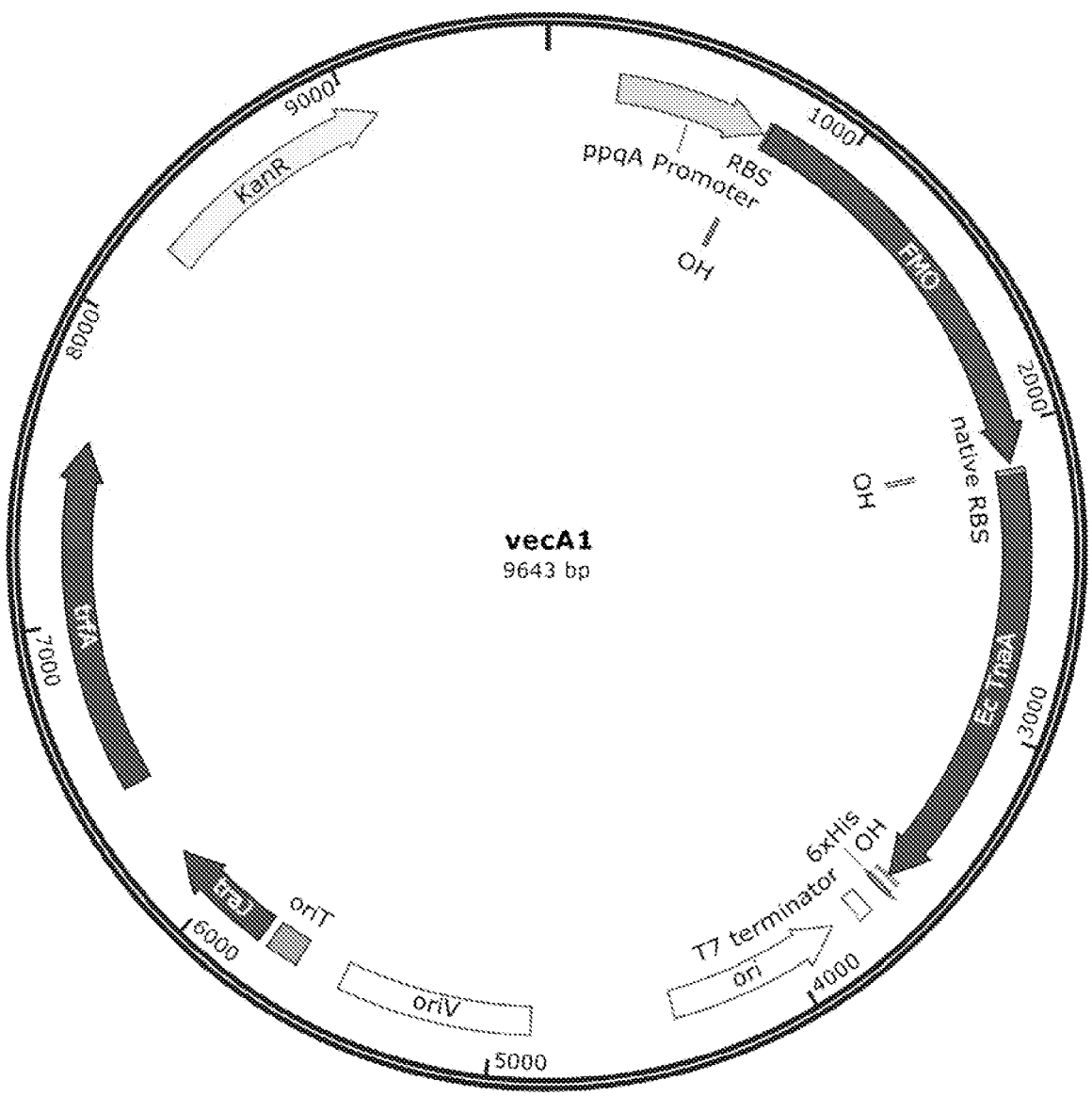
FIG. 5 illustrates a shuttle vector for overexpression of FMO and TnaA as an operon from ppqA promoter in methanotrophic bacteria.
Figure 6:
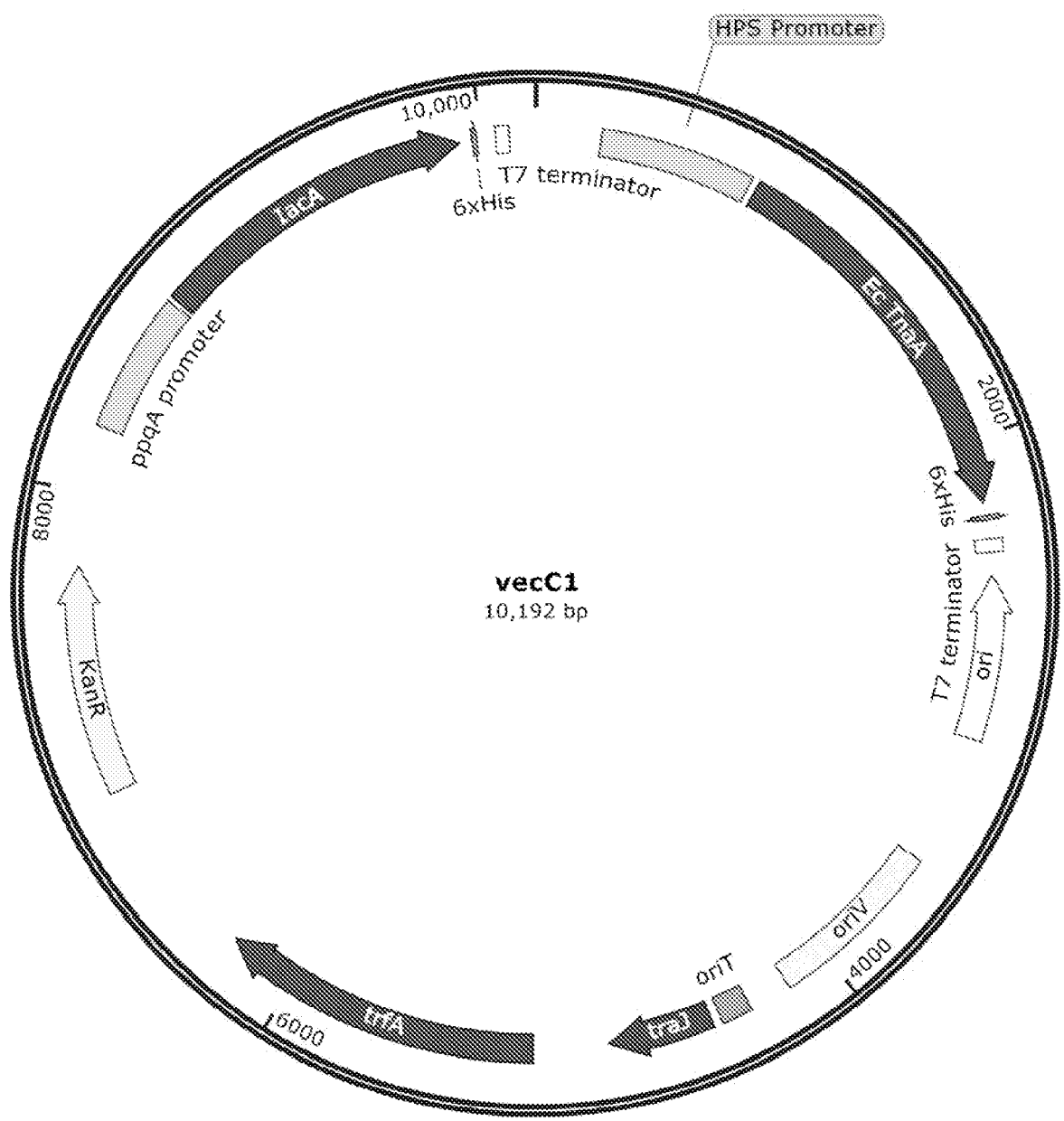
FIG. 6 illustrates a shuttle vector for overexpression of TnaA from hps promoter and IacA from ppqA promoter in methanotrophic bacteria.

As used herein, the term "genetic engineering", "genetic manipulation", "recombination", "recombinant DNA technology" and the likes are used interchangeably and refers to the act of modifying the genetic makeup/DNA of an organism. This modification for example, by way of introduction of a foreign gene/DNA into the organism, or manipulation of existing gene/DNA of the organism, to arrive at a recombinant organism. Thus, the term "recombinant" or the likes and variant terminologies thereof is also within the purview of the above definition. In some embodiments, the present disclosure provides a recombinant methanotrophic bacterium.

As used herein, the term "native" gene(s) refers to the gene(s) known to be naturally present/existing in an organism. The term native gene(s) refers to the gene(s) known to be naturally present/existing in an organism, that may be further transformed to another organism to develop a recombinant organism. Thus, the term "native" gene(s) refers to any gene that occurs naturally in an organism, regardless of whether it is further modified or transformed into another organism to create such a recombinant organism. For example, the term native gene(s) refers to the gene(s) known to be naturally present/existing in a methanotrophic bacterium, that may be further employed for genetic engineering to develop a recombinant methanotrophic bacterium. Similarly, the term native gene(s) refers to the gene(s) known to be present/existing in the same methanotrophic bacterium which may be further modified for genetic engineering to modify the bacterium to a recombinant methanotrophic bacterium.

Additionally, when the gene employed for genetic engineering is a native gene, it means that the recombinant methanotrophic bacterium obtained by the genetic engineering has one or more additional copy of said native gene apart from the copy/copies already present or existing in the methanotrophic bacterium before genetic engineering.

As used herein, the term "heterologous" gene(s) refers to the gene that is not native, i.e. not present or existing naturally in an organism. Accordingly, the term heterologous gene(s) refers to the gene(s) that is not present or existing naturally in an organism, for example, a methanotrophic bacterium and a gene from another organism. Thus, the term heterologous gene(s) also refers to the gene(s) that is from a non-methanotrophic organism and is used for modifying a methanotrophic bacterium to obtain a genetically modified/recombinant methanotrophic bacterium. Further, the heterologous gene can be an unmodified heterologous gene, or a modified heterologous gene. In some embodiments, a modified heterologous gene comprises a codon-optimized heterologous gene, a mutated heterologous gene, or a combination thereof.

In some embodiments, the native gene, the heterologous gene or a combination thereof are expressed through genomic expression, extra chromosomal expression, episomal expression or any combinations thereof.

As used herein, the term "overexpression" of gene(s) refers to expression of one or more copies of a gene to produce one or more copies of corresponding protein. This overexpression can be of a single gene, or two or more genes. In some embodiments, a single gene is overexpressed. In some embodiments, the overexpression is of two or more genes expressed separately or expressed simultaneously. In some embodiments, expression of two or more genes simultaneously is also termed as 'co-expression'. Therefore, in some embodiments, the term overexpression also encompasses 'co-expression'.

The overexpressed gene can be a native gene, a heterologous gene, or a combination thereof. In some embodiments, overexpression refers to the features including but not limiting to: expression of one or more copies of gene(s) native to methanotrophic bacterium; expression of one or more copies of gene(s) heterologous to methanotrophic bacterium; or expression of one or more copies of native gene(s) and heterologous gene(s) in methanotrophic bacterium.

In some embodiments, overexpression by expressing one or more copies of native gene(s) in a methanotrophic bacterium is achieved by transforming additional copies of said native gene(s) into the methanotrophic bacterium; enhancing the expression of the already existing (native) gene in the methanotrophic bacterium; or a combination thereof.

In some embodiments, overexpression by expressing of one or more copies of native gene(s) in methanotrophic bacterium is achieved by transforming one or more copies of said native gene(s) into a methanotrophic bacterium. In some embodiments, expression of a single additional copy of a native gene by transformation in methanotrophic bacterium refers to overexpression of said native gene in the methanotrophic bacterium. In some embodiments, expression of two or more additional copies of a native gene by transformation in methanotrophic bacterium refers to overexpression of said gene in the methanotrophic bacterium.

In some embodiments, overexpression refers to enhancing the expression of a native gene in a methanotrophic bacterium, wherein said enhancement is by producing one or more copies of the gene in addition to the copy/copies already produced in the methanotrophic bacterium. Such overexpression by enhancing the expression of the native gene is achieved by altering the strength of a promoter in methanotrophic bacterium, by deletion/overexpression/mutation of positive or negative regulators controlling the gene expression, by optimizing the gene sequence to enable better transcription, by optimizing the gene sequence to enable better translation, by optimizing the gene sequence to enhance protein expression and folding, by co-expression of chaperones to enable better expression and folding, by optimizing the gene sequence to enhance protein activity or any combinations thereof. In some embodiments, altering the strength of the promoter to enhance the expression of native gene comprises replacing the native promoter with promoter of higher strength, mutating the native promoter to optimize the promoter regulatory elements, overexpression/deletion/mutation of transcriptional or translational regulators driving protein expression, or any combinations thereof.

In some embodiments, overexpression by expression of one or more copies of heterologous gene(s) in methanotrophic bacterium is achieved by transforming the heterologous gene(s) in a methanotrophic bacterium. In some embodiments, expression of a single copy of a heterologous gene in methanotrophic bacterium refers to overexpression of said gene in the methanotrophic bacterium, especially when such a gene is not naturally present in the said bacterium. In some embodiments, expression of two or more copies of a heterologous gene in methanotrophic bacterium refers to overexpression of said gene in the methanotrophic bacterium.

In some embodiments, overexpression is achieved through expression of a transformed gene (either a native gene, a heterologous gene or both) in methanotrophic bacteria by genomic integration, extrachromosomal DNA expression, episomal expression, or any combination thereof.

In some embodiments, the level of overexpression of the gene can be varied based on number of factors regulating gene expression including but not limited to: whether the gene is present or expressed episomally, extra-chromosomally or on the genome; the nature of the promoter used to drive expression; codon optimization of the gene sequence; number of copies of the gene introduced; the sequence of the ribosomal binding site and so on.

As used herein, the term "co-expression" of gene(s) refers to simultaneous expression of two or more genes. The two or more genes are native genes or heterologous genes to an organism, or a combination of both native and heterologous genes. In some embodiments, the two or more genes are native genes to a methanotrophic bacterium. In some embodiments, the two or more genes are heterologous genes to a methanotrophic bacterium. In some embodiments, the two or more genes are a combination of native and heterologous genes to a methanotrophic bacterium.

In some embodiments, the co-expression genes are driven by same or different promoters. In some embodiments, the two or more co-expression genes can be expressed in a single vector or multiple vectors.

In some embodiments, the co-expression genes can be expressed on the genome. In some embodiments, the co-expression genes are for extrachromosomal expression. In some embodiments, the co-expression genes are for episomal expression. In some embodiments, the co-expression genes are expressed through any combination of episomal expression, extrachromosomal expression and genomic expression.

In some embodiments, the level of co-expression of the gene can be varied based on number of factors regulating gene expression including but not limited to: whether the genes are present or expressed episomally, extra-chromosomally or on the genome; the nature of the promoter used to drive expression; codon optimization of the gene sequence; number of copies of the gene introduced; the sequence of the ribosomal binding site; modification of regulators driving gene expression, and so on.

As used herein, the term "knock down" of gene(s) refers to reducing or down-regulating or completely terminating the expression of gene(s). In some embodiments, knock down of gene(s) can be achieved by complete removal or deletion of the gene, or partial removal or deletion of the gene. In some embodiments, knock down of gene(s) can also be achieved by introducing a transgene or point mutation to lower or terminate gene expression, by introducing a stop codon at alternate sites or other known approaches of gene knock-down. In some embodiments, knock down of gene(s) can be achieved by replacing the gene of interest with a homologue of lower activity or no activity.

As used herein, the term "enzyme" refers to a protein that helps to convert substrates to products in a biological reaction.

In some embodiments, an enzyme can be a "oxygenase" that are involved in the transfer of oxygen molecules to a substrate. During the course of the reaction, the substrate is oxidized to produce an intermediate product or final product or a combination of both. In some embodiments, the enzyme can be "dehydrogenase" that oxidizes a substrate by reducing an electron acceptor, usually $NAD^+/NADP^+$ or a flavin coenzyme such as FAD or FMN.

As used herein, the term "indole" refers to an aromatic heterocyclic organic compound with a bicyclic structure, consisting of a six-membered benzene ring fused to a five-membered nitrogen-containing pyrrole ring with a molecular formula of $C_8H_7N$.

As used herein, the term "indoxyl" refers to an aromatic heterocyclic organic compound with a bicyclic structure, consisting of a six-membered benzene ring fused to a five-membered nitrogen-containing pyrrole ring having an hydroxyl group with a molecular formula of $C_8H_7NO$.

As used herein, the term "indigo" refers to an aromatic heterocyclic organic compound consisting of respectively of two six-membered benzene rings fused to a five-membered nitrogen-containing pyrrole ring a molecular formula of $C_{16}H_{10}N_2O_2$.

The present disclosure aims at providing a commercially scalable, cost-effective, biological and ecofriendly route for indigo synthesis. In particular, the present disclosure deviates from the traditional/conventional chemical synthesis of indigo and provides a sustainable and eco-friendly route for producing indigo in biological system.

Indigo is a derivative of the native aromatic amino acid biosynthesis pathway. In the present disclosure, recombinant methanotrophic bacteria are provided which have been engineered for synthesis of indigo from methane.

Methane is a sustainable source of carbon. Currently, solutions to convert methane into useful products are limited. Methanotrophic bacteria (methanotrophs) use significantly different metabolic pathways as they use only methane or Cl substrates as the sole carbon and energy source. The present inventors were able to engineer methanotrophic bacteria to enable the developed recombinant methanotrophs to convert methane to indigo via. shikimic acid pathway.

Accordingly, the present disclosure provides engineered methanotrophs for conversion of methane to indigo. The present disclosure particularly provides recombinant methanotrophic bacteria capable of producing indigo from methane.

The present disclosure provides recombinant methanotrophic bacterium capable of producing indigo from methane, said bacterium comprising one or more genes capable of increasing concentration of indole followed by conversion of said indole to indoxyl during methane utilization via. shikimic acid pathway, wherein subsequent oxidation of indoxyl results in indigo.

In some embodiments, the present disclosure provides a recombinant methanotrophic bacterium capable of producing indigo from methane, comprising:
  a gene encoding enzyme for increasing concentration of indole; and
  a gene encoding enzyme for converting the indole to indoxyl,
wherein the concentration of indole is increased by:
a) conversion of tryptophan to indole, or
b) reducing or preventing formation of tryptophan from indole, or both a) and b).

In some embodiments, the present disclosure provides a recombinant methanotrophic bacterium capable of producing indigo from methane, comprising:
  a gene encoding enzyme for increasing concentration or levels of indole; and a gene encoding enzyme for converting the indole to indoxyl, wherein the concentration of indole is increased, among others, by conversion of tryptophan to indole, or by preventing or reducing the rate of formation of tryptophan from indole, or both.

In some embodiments, the concentration of indole is increased in the recombinant methanotrophic bacterium by at least about five-fold compared to a corresponding wild-type methanotrophic bacterium.

In some embodiments, the concentration of indole is increased in the recombinant methanotrophic bacterium by about five-fold to fifty fold compared to a corresponding wild-type methanotrophic bacterium.

In some embodiments, the concentration of indole is increased in the recombinant methanotrophic bacterium by about five-fold, eight-fold, ten-fold, fifteen fold, twenty fold, thirty fold, forty fold or fifty fold compared to a corresponding wild-type methanotrophic bacterium.

In some embodiments of the present disclosure,
the gene encoding enzyme for increasing concentration of indole, and
the gene encoding enzyme for converting the indole to indoxyl,
are heterologous genes i.e. genes not native to methanotrophic bacterium.

In some embodiments, the increase in concentration of indole is caused by overexpression, codon optimization, mutation or any combination thereof, of the gene encoding enzyme for converting the tryptophan to indole.

In some embodiments, the conversion of the indole to indoxyl is caused by overexpression, codon optimization, mutation or any combination thereof, of the gene encoding enzyme for converting the indole to indoxyl.

In some embodiments, the gene encoding enzyme for increasing concentration of indole is a gene encoding tryptophanase (TnaA).

In some embodiments, the gene encoding enzyme for increasing concentration of indole is a gene encoding mutant beta subunit of tryptophan synthase (mutant TrpB).

In some embodiments, the gene encoding enzyme for increasing concentration of indole is a gene encoding tryptophanase (TnaA) and a gene encoding mutant beta subunit of tryptophan synthase (mutant TrpB).

In some embodiments, increasing concentration of indole comprises conversion of tryptophan to indole. In some embodiments, said conversion of tryptophan to indole is facilitated or catalyzed by TnaA.

In some embodiments, increasing concentration of indole comprises reducing or preventing formation of tryptophan from indole. In some embodiments, preventing formation of tryptophan refers to preventing the conversion of indole to tryptophan. In some embodiments, reducing formation of tryptophan from indole refers to reducing the rate of conversion of indole to tryptophan. In some embodiments reducing formation of tryptophan from indole refers to reducing the rate of conversion of indole to tryptophan completely. In some embodiments, reducing formation of tryptophan from indole refers to reducing the rate of conversion of indole to tryptophan by about at least two fold when compared to the conversion of indole to tryptophan in presence of an enzyme catalyzing conversion of indole to tryptophan. In some embodiments, the enzyme which catalyzes conversion of indole to tryptophan is a wild-type or native TrpB enzyme. Accordingly, in some embodiments, reducing formation of tryptophan from indole refers to reducing the rate of conversion of indole to tryptophan by about at least two fold when compared to the conversion of indole to tryptophan in presence of a wild-type or native TrpB enzyme.

In some embodiments, reducing the formation of tryptophan from indole refers to reducing the rate of conversion of indole to tryptophan by about at least three fold, four fold, five-fold, six fold, seven fold, eight fold, nine fold, ten-fold or completely, when compared to the conversion of indole to tryptophan in presence of a wild-type or native TrpB enzyme.

In some embodiments, preventing the formation of tryptophan from indole refers to preventing the conversion of indole to tryptophan completely, when compared to the conversion of indole to tryptophan occurring in presence of a wild-type or native TrpB enzyme.

In some embodiments, the formation of tryptophan from indole is reduced or prevented by mutating native TrpB.

In some embodiments, the mutant TrpB refers to a TrpB gene which is mutated within the methanotrophic bacterium by known mutation techniques to obtain a mutant TrpB gene, or a mutant TrpB gene developed and transformed into the methanotrophic bacterium, or a combination thereof.

In some embodiments, the B domain (TrpB) of tryptophan synthase catalyzes the condensation of serine and indole to form tryptophan. Mutation in TrpB prevents tryptophan formation (irrespective of presence of active alpha subunit) and leads to accumulation of indole.

In some embodiments, the gene encoding enzyme for converting the indole to indoxyl is a gene encoding an oxidase or dehydrogenase.

In some embodiments, the gene encoding enzyme for converting the indole to indoxyl is a gene encoding an indole oxidase.

In some embodiments, the indole oxidase is a flavin-containing monooxygenase (FMO).

In some embodiments, the gene encoding enzyme for converting the indole to indoxyl is a gene encoding a dehydrogenase.

In some embodiments, the dehydrogenase is a acyl-CoA dehydrogenase-like protein (IacA).

In some embodiments, the gene encoding enzyme for converting the indole to indoxyl is selected from a gene encoding flavin-containing monooxygenase (FMO), a gene encoding acyl-CoA dehydrogenase-like protein (IacA), or a combination thereof.

In some embodiments, the gene encoding enzyme for converting the indole to indoxyl is a gene encoding flavin-containing monooxygenase (FMO).

In some embodiments, the gene encoding enzyme for converting the indole to indoxyl is a gene encoding acyl-CoA dehydrogenase-like protein (IacA).

In some embodiments, the gene encoding enzyme for converting the indole to indoxyl is a gene encoding flavin-containing monooxygenase (FMO) and a gene encoding acyl-CoA dehydrogenase-like protein (IacA).

In some embodiments, the genes encoding TnaA, mutant TrpB, FMO and IacA are heterologous genes. In some embodiments, said heterologous genes TnaA, mutant TrpB, FMO and IacA are unmodified, codon-optimized, mutated, or any combination of heterologous genes thereof. In some embodiments, mutated or codon-optimized genes are employed to achieve the desired expression of said genes TnaA, mutant TrpB, FMO and IacA, thereby leading to indigo synthesis in the recombinant methanotrophic bacterium. In embodiments of the present disclosure, wild-type/naturally occurring methanotrophic bacteria do not have indigo biosynthesis pathway genes including TnaA, mutant TrpB, FMO and IacA and therefore does not produce any indigo.

In some embodiments, the heterologous genes encoding TnaA, mutant TrpB, FMO and IacA are sourced from bacteria, plant, yeast, or any combination thereof.

In some embodiments, the TnaA gene is sourced from *E. coli*. In some embodiments, the TnaA gene is sourced from *E. coli* strain K-12. In some embodiments, the TnaA gene is sourced from *E. coli* strain K-12 of genotype XL1-Blue. In some embodiments, the TnaA gene is sourced from *E. coli* strain K-12 of genotype S17-1.

In some embodiments, the TnaA gene is sourced from organisms belonging to Eubacteria, Archaebacteria, fungi, plants and combinations thereof.

In some embodiments, the TnaA gene is sourced from *E. coli* species, *Kleibsella oxytoca, Shigella* species and/or other organisms comprising TnaA gene.

In some embodiments, the TrpB gene is sourced from a methanotrophic bacterium, wherein said TrpB gene is either mutated in the methanotrophic bacterium by known mutation techniques to obtain a mutant TrpB gene, or a mutant TrpB gene is developed and transformed into a methanotrophic bacterium. Accordingly, said mutant TrpB gene is a heterologous gene for the methanotrophic bacterium. In embodiments discussed above, the mutant TrpB reduces or prevents the reversible formation of tryptophan from indole.

In some embodiments, the TrpB gene is sourced from *Methylococcus capsulatus* and the recombinant methanotrophic bacterium of the present disclosure comprises a mutant TrpB gene.

In some embodiments, the TrpB gene is sourced from organisms belonging to Eubacteria, Archaebacteria, fungi, plants, and combinations thereof.

In some embodiments, the TrpB gene is sourced from *Arabidopsis thaliana, Bacillus subtilis, E. coli* K12, *Saccharomyces cerevisiae* and/or other organisms comprising TrpB gene.

In some embodiments, the FMO gene is sourced from *Methylophaga* sp or *Corynebacterium* sp.

In some embodiments, the FMO gene is sourced from *Methylophaga* sp. selected from a group comprising *Methylophaga aminisulfidivorans* MP, *Methylophaga* sp strain SK1 and a combination thereof. In some embodiments, the FMO gene is sourced from *Corynebacterium* sp. selected from a group comprising *Corynebacterium glutamicum, Corynebacterium jeikeium, Corynebacterium striatum, Corynebacterium bovis*, and combinations thereof.

In some embodiments, the FMO gene is sourced from Methylophaga sp. and codon-optimized for expression in a methanotrophic bacterium. In some embodiments, the FMO gene is sourced from Methylophaga sp. and codon-optimized for expression in *Methylococcus capsulatus, Methylomicrobium buryatense*, or a combination thereof.

In some embodiments, the FMO gene is sourced from *Corynebacterium glutamicum* and codon-optimized for expression in a methanotrophic bacterium. In some embodiments, the FMO gene is sourced from *Corynebacterium glutamicum* and codon-optimized for expression in *Methylococcus capsulatus, Methylomicrobium* buryatense, or a combination thereof.

In some embodiments, the IacA gene is sourced from *Acinetobacter baumannii*.

In some embodiments, the IacA gene is sourced from *Acinetobacter baumannii* and codon-optimized for expression in *Methylococcus capsulatus, Methylomicrobium* buryatense, or a combination thereof.

In some embodiments, the TnaA comprises a nucleic acid sequence set forth as SEQ ID NO. 1 or a nucleic acid sequence having at least 80% identity to SEQ ID NO. 1; and a corresponding amino acid sequence set forth as SEQ ID NO. 2 or an amino acid sequence having at least 80% identity to SEQ ID NO. 2. In some embodiments, the TnaA gene comprising a nucleic acid sequence set forth as SEQ ID NO. 1 is a gene from *Escherichia coli* XL1-Blue strain. In some embodiments, the TnaA gene comprising a nucleic acid sequence set forth as SEQ ID NO. 1 is a gene from *Escherichia coli* S17-1 strain.

In some embodiments, the mutant TrpB comprises a nucleic acid sequence set forth as SEQ ID NO. 3 or a nucleic acid sequence having at least 80% identity to SEQ ID NO. 3; and a corresponding amino acid sequence set forth as SEQ ID NO. 4 or an amino acid sequence having at least 80% identity to SEQ ID NO. 4. In some embodiments, the mutant TrpB comprises a nucleic acid sequence set forth as SEQ ID NO. 3 wherein a wild-type/native TrpB gene is sourced from *Methylococcus capsulatus* and is mutated to develop SEQ ID NO. 3.

In some embodiments, the FMO comprises a nucleic acid sequence set forth as SEQ ID NO. 5 or a nucleic acid sequence having at least 80% identity to SEQ ID NO. 5; and a corresponding amino acid sequence set forth as SEQ ID NO. 6 or an amino acid sequence having at least 80% identity to SEQ ID NO. 6. In some embodiments, the FMO gene comprises a nucleic acid sequence set forth as SEQ ID NO. 5 which is a codon-optimized gene for expression in methanotrophic bacteria. In some embodiments, the FMO gene is sourced from *Methylophaga aminisulfidivorans* and codon-optimized to develop SEQ ID NO. 5 for expression in methanotrophic bacteria.

In some embodiments, the FMO comprises a nucleic acid sequence set forth as SEQ ID NO. 36 or a nucleic acid sequence having at least 80% identity to SEQ ID NO. 36; and a corresponding amino acid sequence set forth as SEQ ID NO. 37 or an amino acid sequence having at least 80% identity to SEQ ID NO. 37. In some embodiments, the FMO gene comprises a nucleic acid sequence set forth as SEQ ID NO. 36 which is a codon-optimized gene for expression in methanotrophic bacteria. In some embodiments, the FMO gene is sourced from *Corynebacterium glutamicum* and codon-optimized to develop SEQ ID NO. 36 for expression in methanotrophic bacteria.

In some embodiments, the IacA comprises a nucleic acid sequence set forth as SEQ ID NO. 7 or a nucleic acid sequence having at least 80% identity to SEQ ID NO. 7; and a corresponding amino acid sequence set forth as SEQ ID NO. 8 or an amino acid sequence having at least 80% identity to SEQ ID NO. 8. In some embodiments, the IacA gene comprises a nucleic acid sequence set forth as SEQ ID NO. 7 which is a codon-optimized gene for expression in methanotrophic bacteria. In some embodiments, the IacA gene is sourced from *Acinetobacter baumannii* and codon-optimized to develop SEQ ID NO. 7 for expression in methanotrophic bacteria.

In some embodiments, the nucleic acid sequence or corresponding amino acid sequence that possesses at least 80% identity with respect to the nucleic acid or amino acid sequences described above (TnaA, mutant TrpB, FMO and IacA) encompasses nucleic acid or amino acid sequences having 80%, 81%, 82%, 83%, 84%, 85%, 86%, 87%, 88%, 89%, 90%, 91%, 92%, 93%, 94%, 95%, 96%, 97%, 98%, or 99% identity, including all values falling within the range of 80% to 99.99%.

In some embodiments, the recombinant methanotrophic bacterium of the present disclosure comprises an overexpressed gene, said overexpressed gene selected from a group comprising 3-Deoxy-D-arabinoheptulosonate 7-phosphate synthase (DAHP synthase), Phospho-2-dehydro-3-deoxyheptonate aldolase (AroF), 3-Dehydroquinate synthase (AroB), 3-dehydroquinate dehydratase (AroD), Shikimate dehydrogenase (AroE), Shikimate kinase (AroK), 3-Phosphoshikimate 1-carboxyvinyltransferase (AroA), Chorismate synthase (AroC) and combinations thereof.

In some embodiments, the recombinant methanotrophic bacterium of the present disclosure comprises an overexpressed gene of shikimic acid or shikimate pathway, said overexpressed gene of shikimate pathway selected from a group comprising 3-Deoxy-D-arabinoheptulosonate 7-phosphate synthase (DAHP synthase), Phospho-2-dehydro-3-deoxyheptonate aldolase (AroF), 3-Dehydroquinate synthase (AroB), 3-dehydroquinate dehydratase (AroD), Shikimate dehydrogenase (AroE), Shikimate kinase (AroK), 3-Phosphoshikimate 1-carboxyvinyltransferase (AroA), Chorismate synthase (AroC), and combinations thereof.

In some embodiments, the recombinant methanotrophic bacterium of the present disclosure comprises the overexpressed gene DAHP synthase. In some embodiments, the DAHP synthase is a native gene of methanotrophic bacterium, or a heterologous gene from a non-methanotrophic source. In some embodiments, the DAHP synthase is a native gene of *Methylococcus capsulatus*.

In some embodiments, the recombinant methanotrophic bacterium of the present disclosure comprises the overexpressed gene AroF. In some embodiments, the AroF is a native gene of methanotrophic bacterium, or a heterologous gene from a non-methanotrophic source. In some embodiments, the AroF is a heterologous gene sourced from *E. coli*. In some embodiments, the AroF is a heterologous gene sourced from *E. coli*, wherein said AroF is mutated to develop a mutant AroF to alter regulation of the shikimate pathway.

In some embodiments, the recombinant methanotrophic bacterium of the present disclosure comprises the overexpressed gene AroB. In some embodiments, the AroB is a native gene of methanotrophic bacterium, or a heterologous gene from a non-methanotrophic source. In some embodiments, the AroB is a native gene of *Methylococcus capsulatus*.

In some embodiments, the recombinant methanotrophic bacterium of the present disclosure comprises the overexpressed gene AroD. In some embodiments, the AroD is a native gene of methanotrophic bacterium, or a heterologous gene from a non-methanotrophic source. In some embodiments, the AroD is a native gene of *Methylococcus capsulatus*.

In some embodiments, the recombinant methanotrophic bacterium of the present disclosure comprises the overexpressed gene AroE. In some embodiments, the AroE is a native gene of methanotrophic bacterium, or a heterologous gene from a non-methanotrophic source. In some embodiments, the AroE is a native gene of *Methylococcus capsulatus*.

In some embodiments, the recombinant methanotrophic bacterium of the present disclosure comprises the overexpressed gene AroK. In some embodiments, the AroK is a native gene of methanotrophic bacterium, or a heterologous gene from a non-methanotrophic source. In some embodiments, the AroK is a native gene of *Methylococcus capsulatus*.

In some embodiments, the recombinant methanotrophic bacterium of the present disclosure comprises the overexpressed gene AroA. In some embodiments, the AroA is a native gene of methanotrophic bacterium, or a heterologous gene from a non-methanotrophic source. In some embodiments, the AroA is a native gene of *Methylococcus capsulatus*.

In some embodiments, the recombinant methanotrophic bacterium of the present disclosure comprises the overexpressed gene AroC. In some embodiments, the AroC is a native gene of methanotrophic bacterium, or a heterologous gene from a non-methanotrophic source. In some embodiments, the AroC is a native gene of *Methylococcus capsulatus*.

In some embodiments, the genes DAHP Synthase, AroF, AroE, AroK, AroB, AroC, AroA and AroD are derived from methanotrophic bacteria. In some embodiments, the genes DAHP Synthase, AroF, AroE, AroK, AroB, AroC, AroA and AroD are derived from methanotrophic bacterium selected from a group comprising *Methylococcus capsulatus, Methylomicrobium buryatense, Methylomicrobium alcaliphilum, Methylomicrobium kenyanse, Methylomicrobium album, Methylocapsa acidiphila, Methylocella silvestris, Methylosinus trichosporium, Methylacidiphilum infernorum* V4, *Methylomonas methanica, Methylosinus sporium, Methylocella palustris, Methylocystis parvus, Methylovulum miyakonense, Methylocystis echinoides, Methylomonas rubra, Methylococcus thermophilus, Methylomonas aurantiaca, Methylomonas fodinarum, Methylomicrobium japanense* and *Methylococcaceae bacterium*.

In some embodiments, the overexpression of the gene in the recombinant methanotrophic bacterium of the present disclosure is achieved by altering promoter strength of native gene(s) of methanotrophic bacterium. In some embodiments, the overexpression of the gene in the recombinant methanotrophic bacterium of the present disclosure is achieved by altering promoter strength of native gene of methanotrophic bacterium selected from the group consisting of DAHP Synthase, AroF, AroB, AroD, AroE, AroK, AroA, AroC and combinations thereof.

In some embodiments, the overexpression of the gene in the recombinant methanotrophic bacterium of the present disclosure is achieved by transforming a gene selected from the group consisting of DAHP Synthase, AroF, AroB, AroD, AroE, AroK, AroA, AroC and combinations thereof, and wherein the transformed gene is a native gene to methanotrophic bacterium, or is a heterologous gene. In some embodiments, overexpression is achieved in the recombinant methanotrophic bacterium by transforming a native gene selected from the group consisting of DAHP Synthase, AroB, AroD, AroE, AroK, AroA, AroC and combinations thereof, into a methanotrophic bacterium. In some embodiments, overexpression is achieved in the recombinant methanotrophic bacterium by transforming a heterologous gene such as AroF, into a methanotrophic bacterium. In some embodiments, the native gene, the heterologous gene or both are either unmodified, codon-optimized, mutated or any combination thereof. In some embodiments, mutated or codon-optimized genes are employed to achieve the desired expression of said genes, thereby leading to indigo synthesis in the recombinant methanotrophic bacterium.

In some embodiments, the recombinant methanotrophic bacterium of the present disclosure comprises a knocked-down gene. In some embodiments, said knocked-down gene is selected from the group consisting of genes downregulating the transcription of tryptophan operon such as Tryptophan operon regulator, tyrosine aminotransferase, aspartate aminotransferase, or any combinations thereof.

In some embodiments, aspartate transaminase and aspartate aminotransferase are used interchangeably and refer to enzymes that catalyze the reversible transfer of an amino group between aspartate and glutamate. These enzymes play a key role in amino acid metabolism.

In some embodiments, the gene encoding DAHP synthase comprises a nucleic acid sequence set forth as SEQ ID NO. 9 or a nucleic acid sequence having at least 80% identity to SEQ ID NO. 9; and a corresponding amino acid sequence set forth as SEQ ID NO. 10 or an amino acid sequence having at least 80% identity to SEQ ID NO. 10.

In some embodiments, the gene encoding AroF comprises a nucleic acid sequence set forth as SEQ ID NO. 11 or a nucleic acid sequence having at least 80% identity to SEQ ID NO. 11; and a corresponding amino acid sequence set forth as SEQ ID NO. 12 or an amino acid sequence having at least 80% identity to SEQ ID NO. 12.

In some embodiments, the gene encoding AroF comprises a nucleic acid sequence set forth as SEQ ID NO. 38 or a nucleic acid sequence having at least 80% identity to SEQ ID NO. 38; and a corresponding amino acid sequence set forth as SEQ ID NO. 39 or an amino acid sequence having at least 80% identity to SEQ ID NO. 39.

In some embodiments, the gene encoding AroF comprises a nucleic acid sequence set forth as SEQ ID NO. 40 or a nucleic acid sequence having at least 80% identity to SEQ ID NO. 40; and a corresponding amino acid sequence set forth as SEQ ID NO. 41 or an amino acid sequence having at least 80% identity to SEQ ID NO. 41.

In some embodiments, the gene encoding AroF comprises a nucleic acid sequence set forth as SEQ ID NO. 42 or a nucleic acid sequence having at least 80% identity to SEQ ID NO. 42; and a corresponding amino acid sequence set forth as SEQ ID NO. 43 or an amino acid sequence having at least 80% identity to SEQ ID NO. 43.

In some embodiments, the gene encoding AroF comprises a nucleic acid sequence set forth as SEQ ID NO. 44 or a nucleic acid sequence having at least 80% identity to SEQ ID NO. 44; and a corresponding amino acid sequence set forth as SEQ ID NO. 45 or an amino acid sequence having at least 80% identity to SEQ ID NO. 45.

In some embodiments, the gene encoding AroB comprises a nucleic acid sequence set forth as SEQ ID NO. 13 or a nucleic acid sequence having at least 80% identity to SEQ ID NO. 13; and a corresponding amino acid sequence set forth as SEQ ID NO. 14 or an amino acid sequence having at least 80% identity to SEQ ID NO. 14.

In some embodiments, the gene encoding AroD comprises a nucleic acid sequence set forth as SEQ ID NO. 15 or a nucleic acid sequence having at least 80% identity to SEQ ID NO. 15; and a corresponding amino acid sequence set forth as SEQ ID NO. 16 or an amino acid sequence having at least 80% identity to SEQ ID NO. 16.

In some embodiments, the gene encoding AroE comprises a nucleic acid sequence set forth as SEQ ID NO. 17 or a nucleic acid sequence having at least 80% identity to SEQ ID NO. 17; and a corresponding amino acid sequence set forth as SEQ ID NO. 18 or an amino acid sequence having at least 80% identity to SEQ ID NO. 18.

In some embodiments, the gene encoding AroK comprises a nucleic acid sequence set forth as SEQ ID NO. 19 or a nucleic acid sequence having at least 80% identity to SEQ ID NO. 19; and a corresponding amino acid sequence set forth as SEQ ID NO. 20 or an amino acid sequence having at least 80% identity to SEQ ID NO. 20.

In some embodiments, the gene encoding AroA comprises a nucleic acid sequence set forth as SEQ ID NO. 21 or a nucleic acid sequence having at least 80% identity to SEQ ID NO. 21; and a corresponding amino acid sequence set forth as SEQ ID NO. 22 or an amino acid sequence having at least 80% identity to SEQ ID NO. 22.

In some embodiments, the gene encoding AroC comprises a nucleic acid sequence set forth as SEQ ID NO. 23 or a nucleic acid sequence having at least 80% identity to SEQ ID NO. 23; and a corresponding amino acid sequence set forth as SEQ ID NO. 24 or an amino acid sequence having at least 80% identity to SEQ ID NO. 24.

In some embodiments, the gene encoding a tryptophan operon regulator comprises a nucleic acid sequence having at least 80% identity to SEQ ID NO. 30, and a corresponding amino acid sequence having at least 80% identity to SEQ ID NO. 31.

In some embodiments, the gene encoding tyrosine aminotransferase comprises a nucleic acid sequence having at least 80% identity to SEQ ID NO. 59; and a corresponding amino acid sequence having at least 80% identity to SEQ ID NO. 60.

In some embodiments, the gene encoding aspartate transaminase comprises a nucleic acid sequence set forth as SEQ ID NO. 34 or a nucleic acid sequence having at least 80% identity to SEQ ID NO. 34; and a corresponding amino acid sequence set forth as SEQ ID NO. 35 or an amino acid sequence having at least 80% identity to SEQ ID NO. 35.

In some embodiments, the nucleic acid sequence or corresponding amino acid sequence that possesses at least 80% identity with respect to the nucleic acid or amino acid sequences described above (DAHP Synthase, AroF, AroE, AroK, AroB, AroC, AroA, AroD, tryptophan operon regulator and aspartate transaminase) encompasses nucleic acid or amino acid sequences having 80%, 81%, 82%, 83%, 84%, 85%, 86%, 87%, 88%, 89%, 90%, 91%, 92%, 93%, 94%, 95%, 96%, 97%, 98%, or 99% identity, including all values falling within the range of 80% to 99.99%.

In some embodiments, the recombinant methanotrophic bacteria comprising TnaA gene improves indole level by converting tryptophan to indole, and thereby reduces tryptophan levels in the shikimic acid pathway.

In some embodiments, the recombinant methanotrophic bacteria comprising mutated TrpB gene improves flux towards indigo formation in the shikimic acid pathway by reducing or preventing the formation of tryptophan from indole.

In some embodiments, the recombinant methanotrophic bacteria comprising gene selected from FMO, IacA, or a combination thereof, improves flux towards indigo formation in the shikimic acid pathway by catalyzing the conversion of indole to indoxyl.

In some embodiments, the overexpressed gene(s) in the recombinant methanotrophic bacteria increases the endogenous pool of shikimic acid pathway metabolites, thereby enhancing indigo formation in the recombinant methanotrophic bacteria. In some embodiments, the recombinant methanotrophic bacteria of the present disclosure comprising overexpressed gene(s) selected from DAHP Synthase, AroF, AroE, AroK, AroB, AroC, AroA, AroD, or any combination of the genes thereof, improve flux towards chorismate formation in the shikimic acid pathway.

In some embodiments, the knocked-down gene(s) in the recombinant methanotrophic bacteria improves the flux towards indigo biosynthesis by reducing the formation of tyrosine and phenyl alanine in the shikimic acid pathway. In some embodiments, the knocked-down gene(s) in the recombinant methanotrophic bacteria improves the flux towards indole formation from chorismate.

In some embodiments of the present disclosure, the recombinant methanotrophic bacterium is selected from the group consisting of *Methylococcus capsulatus, Methylomicrobium buryatense, Methylomicrobium alcaliphilum, Methylomicrobium kenyanse, Methylomicrobium album, Methylocapsa acidiphila, Methylocella silvestris, Methylosinus trichosporium, Methylacidiphilum infernorum* V4, *Methylomonas methanica, Methylosinus sporium, Methylocella palustris, Methylocystis parvus, Methylovulum miyakonense, Methylocystis echinoides, Methylomonas rubra, Methylococcus thermophilus, Methylomonas aurantiaca, Methylomonas fodinarum, Methylomicrobium japanese* and *Methylococcaceae bacterium*.

In some embodiments of the present disclosure, the recombinant methanotrophic bacterium is selected from a group comprising *Methylococcus capsulatus, Methylomicrobium buryatense, Methylosinus trichosporium, Methylomicrobium alcaliphilum* and *Methylomicrobium kenyanse*.

In some embodiments of the present disclosure, the recombinant methanotrophic bacterium is *Methylococcus capsulatus*.

In some embodiments of the present disclosure, the recombinant methanotrophic bacterium is *Methylococcus capsulatus* Bath strain.

In some embodiments of the present disclosure, the recombinant methanotrophic bacterium is *Methylomicrobium buryatense*.

In some embodiments of the present disclosure, the recombinant methanotrophic bacterium is *Methylomicrobium buryatense* strain 5G.

In some embodiments of the present disclosure, the recombinant methanotrophic bacterium comprises a gene encoding tryptophanase (TnaA) and a gene encoding flavin-containing monooxygenase (FMO).

In some embodiments of the present disclosure, the recombinant methanotrophic bacterium comprises a gene encoding tryptophanase (TnaA) and a gene encoding acyl-CoA dehydrogenase-like protein (IacA).

In some embodiments of the present disclosure, the recombinant methanotrophic bacterium comprises a gene encoding tryptophanase (TnaA), a gene encoding flavin-containing monooxygenase (FMO), and a gene encoding acyl-CoA dehydrogenase-like protein (IacA).

In some embodiments of the present disclosure, the recombinant methanotrophic bacterium comprises a gene encoding mutant beta subunit of tryptophan synthase (mutant TrpB) and a gene encoding flavin-containing monooxygenase (FMO).

In some embodiments of the present disclosure, the recombinant methanotrophic bacterium comprises a gene encoding mutant beta subunit of tryptophan synthase (mutant TrpB) and a gene encoding acyl-CoA dehydrogenase-like protein (IacA).

In some embodiments of the present disclosure, the recombinant methanotrophic bacterium comprises a gene encoding mutant beta subunit of tryptophan synthase (mutant TrpB), a gene encoding flavin-containing monooxygenase (FMO), and a gene encoding acyl-CoA dehydrogenase-like protein (IacA).

In some embodiments of the present disclosure, the recombinant methanotrophic bacterium comprises a gene encoding tryptophanase (TnaA), a gene encoding mutant beta subunit of tryptophan synthase (mutant TrpB) and a gene encoding acyl-CoA dehydrogenase-like protein (IacA).

In some embodiments of the present disclosure, the recombinant methanotrophic bacterium comprises a gene encoding tryptophanase (TnaA), a gene encoding mutant beta subunit of tryptophan synthase (mutant TrpB) and a gene encoding flavin-containing monooxygenase (FMO).

In some embodiments of the present disclosure, the recombinant methanotrophic bacterium comprises genes encoding TnaA, mutant TrpB, IacA and FMO.

In all the above embodiments describing different gene combinations, the recombinant methanotrophic bacterium is selected from the group consisting of *Methylococcus capsulatus, Methylomicrobium buryatense, Methylomicrobium Methylomicrobium kenyanse, Methylomicrobium album, Methylocapsa Methylocella silvestris, Methylosinus trichosporium, Methylacidiphilum infernorum* V4, *Methylomonas methanica, Methylosinus sporium, Methylocella palustris, Methylocystis parvus, Methylovulum miyakonense, Methylocystis echinoides, Methylomonas rubra, Methylococcus thermophilus, Methylomonas aurantiaca, Methylomonas fodinarum, Methylomicrobium japanese* and *Methylococcaceae bacterium*.

In all the above embodiments describing different gene combinations, the recombinant methanotrophic bacterium is *Methylococcus capsulatus*.

In all the above embodiments describing different gene combinations, the recombinant methanotrophic bacterium is *Methylomicrobium buryatense*.

In some embodiments, the present disclosure provides recombinant methanotrophic bacteria comprising:
(i) a gene encoding enzyme for increasing concentration of indole, and a gene encoding enzyme for converting the indole to indoxyl; and
(ii) optionally, an overexpressed gene, a knocked-down gene, or a combination of the overexpressed gene and the knocked-down gene.

In some embodiments, the present disclosure provides recombinant methanotrophic bacteria comprising:
  (i) a gene encoding enzyme for increasing concentration of indole, and a gene encoding enzyme for converting the indole to indoxyl; and
  (ii) an overexpressed gene.

In some embodiments, the present disclosure provides recombinant methanotrophic bacteria comprising:
  (i) a gene encoding enzyme for increasing concentration of indole, and a gene encoding enzyme for converting the indole to indoxyl; and
  (ii) a knocked-down gene.

In some embodiments, the present disclosure provides recombinant methanotrophic bacteria comprising:
  (i) a gene encoding enzyme for increasing concentration of indole, and a gene encoding enzyme for converting the indole to indoxyl; and
  (ii) a combination of overexpressed gene and knocked-down gene.

In some embodiments of the present disclosure, the recombinant methanotrophic bacterium comprises:
  a gene selected from TnaA, mutant TrpB, and a combination thereof;
  a gene selected from FMO, IacA, and a combination thereof, and
  a gene selected from an overexpressed gene, a knocked-down gene, or a combination thereof, wherein the overexpressed gene is selected from the group consisting of DAHP Synthase, AroF, AroB, AroD, AroE, AroK, AroA, AroC and combinations thereof, and the knocked-down gene is selected from the group consisting of tryptophan operon regulator genes, tyrosine aminotransferase, aspartate aminotransferase, and combinations thereof.

In some embodiments of the present disclosure, the recombinant methanotrophic bacterium comprises:
  a gene selected from TnaA, mutant TrpB, and a combination thereof;
  a gene selected from FMO, IacA, and a combination thereof, and
  an overexpressed gene selected from the group consisting of DAHP Synthase, AroF, AroB, AroD, AroE, AroK, AroA, AroC and combinations thereof.

In some embodiments of the present disclosure, the recombinant methanotrophic bacterium comprises:
  a gene selected from TnaA, mutant TrpB, and a combination thereof;
  a gene selected from FMO, IacA, and a combination thereof; and
  a knocked-down gene selected from the group consisting of tryptophan operon regulator genes, tyrosine aminotransferase, aspartate aminotransferase and combinations thereof.

In some embodiments of the present disclosure, the recombinant methanotrophic bacterium comprises:
  TnaA gene;
  FMO gene; and
  overexpressed gene of shikimate pathway.

In some embodiments of the present disclosure, the recombinant methanotrophic bacterium comprises:
  TnaA gene;
  FMO gene; and
  one or more overexpressed genes selected from a group consisting of aroA, aroC, aroK, aroE, aroD, DAHP synthase, aroB and aroF.

In some embodiments of the present disclosure, the recombinant methanotrophic bacterium comprises:
  TnaA gene;
  FMO gene; and
  overexpressed genes aroA, aroC, aroK, aroE, aroD, DAHP synthase, aroB and aroF In some embodiments of the present disclosure, the recombinant methanotrophic bacterium comprises:
  TnaA gene;
  FMO gene; and
  one or more overexpressed genes selected from a group consisting of aroA, aroC, aroK, aroE, DAHP synthase, aroB and aroF.

In some embodiments of the present disclosure, the recombinant methanotrophic bacterium comprises:
  TnaA gene or mutant TrpB gene in combination with FMO gene or lac gene; and
  knocked-down gene comprising tryptophan operon regulator gene(s).

In some embodiments of the present disclosure, the recombinant methanotrophic bacterium comprises:
  TnaA gene;
  FMO gene; and
  knock-down of tryptophan operon regulator gene(s).

In some embodiments of the present disclosure, the recombinant methanotrophic bacterium comprises:
  TnaA gene;
  FMO gene;
  knock-down of tryptophan operon regulator gene(s); and
  overexpressed gene(s) of shikimate pathway.

In some embodiments of the present disclosure, the recombinant methanotrophic bacterium comprises:
  TrpB gene;
  FMO gene; and
  overexpressed gene(s) of shikimate pathway.

In some embodiments of the present disclosure, the recombinant methanotrophic bacterium comprises:
  TrpB gene;
  FMO gene; and
  knock-down of tryptophan operon regulator gene(s).

In some embodiments of the present disclosure, the recombinant methanotrophic bacterium comprises:
  TnaA gene;
  IacA gene; and
  overexpressed gene(s) of shikimate pathway.

In some embodiments of the present disclosure, the recombinant methanotrophic bacterium comprises:
  mutant TrpB gene;
  IacA gene; and
  overexpressed gene(s) of shikimate pathway.

In all the above embodiments describing different gene combinations comprising: a gene encoding enzyme for increasing concentration of indole, a gene encoding enzyme for converting the indole to indoxyl, and optionally an overexpressed gene and/or knocked-down gene, the recombinant methanotrophic bacterium is selected from the group consisting of *Methylococcus capsulatus, Methylomicrobium buryatense, Methylomicrobium alcaliphilum, Methylomicrobium kenyanse, Methylomicrobium album, Methylocapsa acidiphila, Methylocella silvestris, Methylosinus trichosporium, Methylacidiphilum infernorum* V4, *Methylomonas methanica, Methylosinus sporium, Methylocella palustris, Methylocystis parvus, Methylovulum miyakonense, Methylocystis echinoides, Methylomonas rubra, Methylococcus thermophilus, Methylomonas aurantiaca, Methylomonas fodinarum, Methylomicrobium japanense* and *Methylococcaceae bacterium*.

In all the above embodiments describing different gene combinations comprising: a gene encoding enzyme for increasing concentration of indole, a gene encoding enzyme for converting the indole to indoxyl, and optionally an overexpressed gene and/or knocked-down gene, the recombinant methanotrophic bacterium is *Methylococcus capsulatus*.

In all the above embodiments describing different gene combinations comprising: a gene encoding enzyme for increasing concentration of indole, a gene encoding enzyme for converting the indole to indoxyl, and optionally an overexpressed gene and/or knocked-down gene, the recombinant methanotrophic bacterium is *Methylomicrobium buryatense*.

In various embodiments of the present disclosure, the recombinant methanotrophic bacterium can comprise any of the genes encoding enzyme for increasing concentration of indole and genes encoding enzyme for converting the indole to indoxyl, in combination with any of the overexpressed gene and/or knocked-down gene described herein.

In some embodiments of the present disclosure, any homologue of the genes described herein can be employed for engineering the recombinant methanotrophic bacterium.

Thus, the present disclosure provides recombinant methanotrophic bacterium as described above which convert methane to indigo. In particular, the present disclosure describes expression or overexpression of heterologous genes, overexpression of native genes, knock down of genes, and combinations thereof, involved in shikimic acid pathway and intermediate metabolites as an approach to synthesize indigo in methanotrophic bacterium.

Shikimate pathway derived metabolites act as precursors for a wide variety of natural products that not only play crucial role in growth and physiological response, but also have high economical value. Intermediates from this pathway are channeled towards different metabolic branches for formation of diverse end-products including aromatic amino acids and their derivatives. Based on aromatic amino acid metabolism and methane metabolism, the present inventors have carefully employed target genes (heterologous genes and native genes) for overexpression and optionally knock down to further enhance the levels of the metabolites. Wild-type methanotrophic bacteria do not synthesize indigo. Particularly, the wild-type methanotrophic bacteria do not have a mechanism to utilize indole for indigo biosynthesis. For manipulation of indigo production in methanotrophic bacteria, the present invention employs/targets genes for increasing indole concentration in the cells and to convert the indole to indoxyl, which further leads to indigo biosynthesis in recombinant methanotrophs. Genes encoding the enzymes TnaA, mutant TrpB, IacA and FMO in different combinations were particularly employed. Optionally, genes of shikimate pathway regulating flux to chorismate are also targeted for overexpression thereby leading to increased concentrations of chorismate. Said genes include but are not limited to DAHP Synthase, AroF, AroE, AroK, AroB, AroC, AroA, and AroD. Other optional target genes are genes of shikimate pathway regulating flux to aromatic amino acid biosynthesis (tryptophan, tyrosine and phenyl alanine). In particular, the genes related to the tryptophan operon regulators, tyrosine aminotransferase, aspartate transaminase are knocked-down to improve the flux towards indigo biosynthesis in recombinant methanotrophs.

Accordingly, in some embodiments of the present disclosure, the conversion of methane to indigo in the recombinant methanotrophic bacteria occurs via the following shikimic acid pathway/mechanism: methane is converted to chorismate followed by conversion of chorismate to tryptophan (a key aromatic amino acid). The levels/concentrations of indole is increased by converting tryptophan to indole, or alternatively by reducing or preventing formation of tryptophan from indole, or both. The conversion of tryptophan to indole is catalyzed by employing enzymes such as TnaA. The mutant TrpB prevents the formation of tryptophan from indole and hence overexpression of mutant TrpB results in indole accumulation. The indole thus synthesized/accumulated is converted to indoxyl in the presence of oxidase or dehydrogenase such as FMO, IacA or a combination thereof. Indoxyl undergoes oxidation in air to form indigo, the blue colored dye.

In an embodiment of the present disclosure, the conversion of methane to indigo in the recombinant methanotrophic bacteria via. shikimic acid pathway is illustrated in FIG. 1.

In embodiments of the present disclosure, the source of methane used by the recombinant methanotrophic bacteria for the production of target metabolites is selected from a group comprising biogas, natural gas, landfill gas, organic waste, pure methane, any source comprising methane and combinations thereof.

The present disclosure thus describes engineering of methane, central carbon metabolism and shikimic acid pathway to improve availability of branch point metabolites and aromatic amino acids for production of indigo in methanotrophic bacteria. This enables the production of indigo by employing the recombinant methanotrophic bacteria described herein using a cost-effective substrate (methane) through a sustainable and ecofriendly process. More particularly, said biosynthesis of indigo is accomplished by genetic transformation of methanotrophic bacteria for expression of specific genes described herein that catalyze the synthesis and accumulation of target compounds from methane.

While the aforementioned aspects have been described for developing a recombinant methanotrophic bacterium for production of indigo compound, each of the aforementioned aspects are identically applicable for a recombinant methanotrophic bacterium developed for production of indoxyl compound. Thus, in some embodiments, the present disclosure also provides a recombinant methanotrophic bacterium capable of producing indoxyl from methane, comprising:
   a gene encoding enzyme for increasing concentration of indole; and
   a gene encoding enzyme for converting the indole to indoxyl,
wherein the concentration of indole is increased by conversion of tryptophan to indole, or by reducing or preventing formation of tryptophan from indole, or both.

Further, while indoxyl is known to readily undergo spontaneous dimerisation in presence of molecular oxygen to produce indigo, a skilled person will understand and know the techniques to isolate said indoxyl for industrial use/applications (prior to its conversion to indigo), and each of such techniques/methodologies to isolate indoxyl are within the purview of the present disclosure and claims.

The present disclosure further provides a method for developing the recombinant methanotrophic bacteria as described above, said method comprising:
   a) transforming or mutating a gene encoding enzyme for increasing concentration of indole, in a wild-type methanotrophic bacteria; and
   b) transforming a gene encoding enzyme for converting the indole to indoxyl, in a wild-type methanotrophic bacteria.

In some embodiments, the method for developing the recombinant methanotrophic bacteria comprises:
   a) transforming a gene encoding an enzyme for conversion of tryptophan to indole, transforming a mutated gene encoding an enzyme for reducing or preventing formation of tryptophan from indole, mutating a gene encoding enzyme for conversion of indole to tryptophan, or any combinations thereof; and
   b) transforming a gene encoding enzyme for converting the indole to indoxyl.

In some embodiments, the method for developing the recombinant methanotrophic bacteria comprises:
   a) transforming a TnaA gene for conversion of tryptophan to indole, transforming a mutant TrpB gene for reducing or preventing formation of tryptophan from indole, or any combinations thereof; and
   b) transforming a gene encoding oxidase or dehydrogenase for converting the indole to indoxyl.

In some embodiments of the method for developing the recombinant methanotrophic bacteria, gene encoding oxidase or dehydrogenase is FMO, IacA or a combination thereof.

In some embodiments, the method for developing the recombinant methanotrophic bacteria comprises:
   a) transforming a TnaA gene, a mutant TrpB gene, or a combination thereof; and
   b) transforming FMO gene, IacA gene, or a combination thereof.

In some embodiments, the method for developing the recombinant methanotrophic bacteria comprises:
   a) designing vector(s) for expression of TnaA gene, a mutant TrpB gene, or a combination thereof, and FMO gene, IacA gene, or a combination thereof; and b) transforming the vector into a wild-type methanotrophic bacteria, to obtain the recombinant methanotrophic bacteria.

In some embodiments, the vector is a single vector expressing TnaA gene.

In some embodiments, the vector is a single vector expressing mutant TrpB gene.

In some embodiments, the vector is a single vector expressing FMO gene.

In some embodiments, the vector is a single vector expressing IacA gene.

In some embodiments, the vector is a co-expression vector expressing a combination of TnaA gene and mutant TrpB.

In some embodiments, the vector is a co-expression vector expressing a combination of FMO gene and IacA gene.

In some embodiments, the vector is a co-expression vector expressing a combination of TnaA gene and a gene selected from FMO gene and IacA gene.

In some embodiments, the vector is a co-expression vector expressing a combination of TnaA gene, FMO gene and IacA gene.

In some embodiments, the vector is a co-expression vector expressing a combination of mutant TrpB and a gene selected from FMO gene and IacA gene.

In some embodiments, the vector is a co-expression vector expressing a combination of mutant TrpB, FMO gene and IacA gene.

In some embodiments, the method for developing the recombinant methanotrophic bacteria further comprises:
a) overexpressing genes selected from a group comprising DAHP Synthase, AroF, AroE, AroK, AroB, AroC, Aro and AroD;
b) knocking-down of genes selected from a group comprising tryptophan operon regulator, tyrosine aminotransferase, aspartate transaminase and combinations thereof; or
c) overexpressing genes and knocking-down of genes as defined in steps (a) and (b), to obtain the recombinant methanotrophic bacteria.

In some embodiments, the method for developing the recombinant methanotrophic bacteria further comprises:
a) designing vector(s) for expression of one or more overexpression genes selected from a group comprising DAHP Synthase, AroF, AroE, AroK, AroB, AroC, AroA, AroD and; and transforming the vector into methanotrophic bacteria; and/or
b) knocking-down of genes selected from tryptophan operon regulator, tyrosine aminotransferase, aspartate transaminase and combinations thereof to obtain the recombinant methanotrophic bacteria.

In some embodiments, the vector is a single vector expressing each overexpression gene separately, or a co-expression vector expressing two or more overexpression genes, wherein the overexpression genes are selected from a group comprising DAHP Synthase, AroF, AroE, AroK, AroB, AroC, AroA and AroD.

In some embodiments, the method for developing the recombinant methanotrophic bacteria comprises:

a) transforming a TnaA gene, transforming a mutant TrpB gene, and/or mutating a native TrpB gene in a methanotrophic bacterium;
b) transforming an FMO gene and/or a IacA gene; and
c) optionally, overexpressing genes selected from a group comprising DAHP Synthase, AroF, AroE, AroK, AroB, AroC, AroA, AroD and combinations thereof, and/or knocking-down of genes selected from tryptophan operon regulator, tyrosine aminotransferase, aspartate transaminase and combinations thereof, in a wild-type methanotrophic bacterium, to obtain the recombinant methanotrophic bacterium.

In some embodiments, overexpressing the genes selected from a group comprising DAHP Synthase, AroF, AroE, AroK, AroB, AroC, AroA and AroD, is carried out by transforming said genes into methanotrophic bacteria, altering promoter strength of native genes, or a combination of both.

In some embodiments, expression, overexpression and/or knock-down of the genes described herein in the methods of the present disclosure can be performed in any sequence/order to develop the recombinant methanotrophic bacteria of the present disclosure. Thus, in other words, the sequence/order of engineering the genes to develop the recombinant methanotrophic bacteria does not adversely impact the end result i.e. obtaining of the recombinant methanotrophic bacteria of the present disclosure.

In some embodiments of the method for developing recombinant methanotrophic bacteria described herein, the developed recombinant methanotrophic bacterium is selected from a group comprising *Methylococcus capsulatus, Methylomicrobium buryatense, Methylomicrobium alcaliphilum, Methylomicrobium kenyanse, Methylomicrobium album, Methylocapsa acidiphila, Methylocella silvestris, Methylosinus trichosporium, Methylacidiphilum infernorum* V4, *Methylomonas methanica, Methylosinus sporium, Methylocella palustris, Methylocystis parvus, Methylovulum miyakonense, Methylocystis echinoides, Methylomonas rubra, Methylococcus thermophilus, Methylomonas aurantiaca, Methylomonas fodinarum, Methylomicrobium japanense* and *Methylococcaceae bacterium*.

In some embodiments of the method for developing recombinant methanotrophic bacteria described herein, the developed recombinant methanotrophic bacterium is selected from a group comprising *Methylococcus capsulatus, Methylomicrobium buryatense, Methylomicrobium alcaliphilum, Methylosinus trichosporium* and *Methylomicrobium kenyanse*.

In some embodiments of the method for developing recombinant methanotrophic bacteria described herein, the developed recombinant methanotrophic bacterium is *Methylococcus capsulatus*.

In some embodiments of the method for developing recombinant methanotrophic bacteria described herein, the developed recombinant methanotrophic bacterium is *Methylomicrobium buryatense*.

In some embodiments of the present disclosure, the method for developing recombinant methanotrophic bacteria comprises the following general steps:

Designing single or multiple vectors comprising gene of interest selected from TnaA, mutant TrpB, FMO, IacA, DAHP Synthase, AroF, AroE, AroK, AroB, AroC, AroA, AroD, genes of tryptophan operon regulators, tyrosine aminotransferase
and aspartate aminotransferase

↓

Transforming a host cell (eg. *E. coli*) with the vector(s)

↓

Selection of host cell transformants (eg. *E. coli* transformants)

↓

Transforming gene of interest in methanotrophic bacterium from
the host cell transformants (eg. *E. coli* transformants) using conjugation
technique (eg. solid mating technique or liquid mating technique)

↓

Selection of methanotrophic bacteria transformants (recombinant
methanotrophic bacteria)

In some embodiments of the present disclosure, the method for developing recombinant methanotrophic bacteria comprises the following general steps:

Designing single or multiple vectors comprising gene of interest selected from TnaA, mutant TrpB, FMO, IacA, DAHP Synthase, AroF, AroE, AroK, AroB, AroC, AroA, AroD, genes of tryptophan operon regulators, tyrosine aminotransferase
and aspartate aminotransferase

↓

Transforming methanotrophic bacterium with the vector(s) by
transformation techniques

↓

Selection of methanotrophic bacteria transformants (recombinant
methanotrophic bacteria)

In some embodiments of the present disclosure, exemplary methods/protocols for developing recombinant methanotrophic bacteria is described in the examples below.

While the aforementioned aspects have been described for a method to develop a recombinant methanotrophic bacterium for production of indigo compound, each of the aforementioned method aspects are identically applicable for a recombinant methanotrophic bacterium developed for production of indoxyl compound. Thus, in some embodiments, the present disclosure also provides a method of developing a recombinant methanotrophic bacterium capable of producing indoxyl from methane, comprising:
  a gene encoding enzyme for increasing concentration of indole; and
  a gene encoding enzyme for converting the indole to indoxyl,
wherein the concentration of indole is increased by conversion of tryptophan to indole, or by reducing or preventing formation of tryptophan from indole, or both.

Further, while indoxyl is known to readily undergo spontaneous dimerisation in presence of molecular oxygen to produce indigo, a skilled person will understand and know the techniques to isolate said indoxyl for industrial use/applications (prior to its conversion to indigo), and each of such techniques/methodologies to isolate indoxyl are within the purview of the present disclosure and claims.

The present disclosure further describes recombinant plasmid or vector for expression of the genes described herein.

In some embodiments, the present disclosure provides vector(s) for expression of genes selected from a group comprising TnaA gene, mutant TrpB gene, FMO gene, IacA gene and combinations thereof.

In some embodiments, the present disclosure provides vector(s) for expression of genes selected from a group comprising DAHP Synthase, AroF, AroE, AroK, AroB, AroC, AroA and AroD.

In some embodiments, the present disclosure provides vector(s) for knocking-down genes selected from a group comprising tryptophan operon regulators, tyrosine aminotransferase, and aspartate transaminase and combinations thereof.

In some embodiments, an expression cassette is provided comprising a promoter, operator, regulator, the gene of interest, terminator, ribosomal binding site and antibiotic resistance genes. In some embodiments, the gene of interest is selected from a group comprising TnaA gene, mutant TrpB gene, FMO gene, IacA gene, DAHP Synthase, AroF, AroE, AroK, AroB, AroC, AroA, AroD, genes of tryptophan operon regulators, tyrosine aminotransferase, aspartate aminotransferase and combinations thereof.

In some embodiments, the vector described herein comprises elements including:
(i) the expression cassette comprising promoter, regulator, operator, gene of interest (genes selected from a group comprising TnaA gene, mutant TrpB gene, FMO gene, IacA gene, DAHP Synthase, AroF, AroE, AroK, AroB, AroC, AroA, AroD and combinations thereof), terminator, ribosomal binding site and antibiotic resistance genes,
(ii) origins of replication compatible with the assembly/transient host organism used for cloning and the final expression host,
(iii) antibiotic resistance markers for selection of vector,
(iv) transfer genes required for conjugation, and combinations thereof.

In some embodiments, the promoter for regulating expression of gene of interest is selected from a group comprising formaldehyde activating enzyme-1 (Fae-1), formaldehyde activating enzyme-2 (Fae-2), coenzyme PQQ synthesis protein (ppqA), methanol dehydrogenase (pmxaf), 3-hexulose-6-phosphate synthase (hps), particulate methane monooxygenase ($\sigma$70), soluble methano monooxygenase ($\sigma$54) and combinations thereof. Said promoter drives the expression of the gene of interest described above either alone or as an operon for gene overexpression.

In some embodiments, the promoters described herein can be isolated or derived from any source. In some embodiments, the promoters described herein are either isolated from methantrophic bacteria selected from *Methylococcus capsulatus, Methylomicrobium buryatense, Methylomicrobium alcaliphilum, Methylomicrobium kenyanse, Methylomicrobium album, Methylocapsa acidiphila, Methylocellasilvestris, Methylosinus trichosporium, Methylacidiphilum infernorum V4, Methylomonas methanica, Methylosinus sporium, Methylocella palustris, Methylocystis parvus, Methylovulum miyakonense, Methylocystis echinoides,*

*Methylomonas rubra, Methylococcus thermophilus, Methylomonas aurantiaca, Methylomonas fodinarum, Methylomicrobium japanense* and *Methylococcaceae bacterium*, or from other bacteria such as *Escherichia. coli*. In some embodiments, the promoters can be native promoters or mutated promoters.

In some embodiments, the promoters are selected from a group comprising SEQ ID NO. 46, SEQ ID NO. 47, SEQ ID NO. 48 and SEQ ID NO. 49.

In some embodiments, the vector is selected from a group comprising of broad host range shuttle vectors that have origin of replication, selection markers, conjugative transfer genes for expression and propagation in methanotrophs and *E. coli*. In one embodiment of the present disclosure, the vectors include IncP/IncQ Origin of replication based vectors, pBBR origin based vectors or similar vectors for achieving the purpose set forth in the present invention (developing recombinant methanotrophic bacteria).

In some embodiments of the present disclosure, the target genes (gene of interest) and promoters are PCR amplified and cloned in vectors. Subsequently, operons containing any combination of target genes described herein are generated for increasing the metabolite pool and target metabolite biosynthesis using methane as substrate.

In another embodiment of the present disclosure, the knock-down of genes selected from tryptophan operon regulator genes, asparatate transaminase or a combination thereof is carried out by techniques selected from homologous recombination, promoter replacement, point mutagenesis, RNA interference (RNAi), Clustered Regularly Interspaced Short Palindromic Repeats (CRISPRs) and any other known technique of gene knock-down.

The present disclosure further relates to a method of producing indigo from methane.

The present disclosure particularly relates to a method of producing indigo from methane, comprising culturing the recombinant methanotrophic bacteria described herein in presence of a methane source. More particularly, the present disclosure describes fermentation/conversion of methane to indigo by employing the recombinant methanotrophic bacteria described herein.

In some embodiments, the methane is a sole carbon and energy source for the recombinant methanotrophic bacterium of the present disclosure. In other words, the recombinant methanotrophic bacterium of the present disclosure only uses methane as a carbon and energy source. In some embodiments, the recombinant methanotrophic bacterium only uses methane as a carbon and energy source, and does not use any other carbon and energy source for growth/metabolism.

In some embodiments of the present disclosure, the methane source employed for the production of indigo is selected from the group comprising pure methane, biogas, natural gas, landfill gas, organic waste, any source comprising methane and combinations thereof.

In some embodiments, the method of producing indigo comprises:
(i) receiving methane source as an input/substrate;
(ii) culturing the recombinant methanotrophic bacteria described herein in presence of methane, thereby converting methane to indigo; and
(iii) optionally, isolating or purifying the indigo from the culture.

In some embodiments, the method of producing indigo comprises:
(i) receiving input selected from a group comprising biogas, natural gas, landfill gas, organic waste, pure methane, any methane containing source, and combinations thereof;
(ii) culturing the recombinant methanotrophic bacteria described herein in presence of said input, thereby converting methane present in the input to indigo; and
(iii) optionally, isolating or purifying the indigo from the culture.

In some embodiments of the method of producing indigo according to the present disclosure, the recombinant methanotrophic bacterium employed is selected from the group consisting of *Methylococcus capsulatus, Methylomicrobium buryatense, Methylomicrobium alcaliphilum, Methylomicrobium kenyanse, Methylomicrobium album, Methylocapsa acidiphila, Methylocella silvestris, Methylosinus trichosporium, Methylacidiphilum infernorum* V4, *Methylomonas methanica, Methylosinus sporium, Methylocella palustris, Methylocystis parvus, Methylovulum miyakonense, Methylocystis echinoides, Methylomonas rubra, Methylococcus thermophilus, Methylomonas aurantiaca, Methylomonas fodinarum, Methylomicrobium japanense* and *Methylococcaceae bacterium*.

In some embodiments, the method of producing indigo comprises:
(i) receiving input selected from a group comprising biogas, natural gas, landfill gas, organic waste, pure methane, any methane containing source, and combinations thereof;
(ii) culturing recombinant *Methylococcus capsulatus* described herein in presence of said input, thereby converting methane present in the input to indigo; and
(iii) optionally, isolating or purifying the indigo from the culture.

In some embodiments, the method of producing indigo comprises:
(i) receiving input selected from a group comprising biogas, natural gas, landfill gas, organic waste, pure methane, any methane containing source, and combinations thereof;
(ii) culturing recombinant *Methylomicrobium* buryatense described herein in presence of said input, thereby converting methane present in the input to indigo; and
(iii) optionally, isolating or purifying the indigo from the culture.

In some embodiments, the method of producing indigo as described above is carried out at a temperature ranging from about 30° C. to 50° C.

In some embodiments, the method of producing indigo as described above is carried out at a pH ranging from about 3.0 to about 8.0.

In some embodiments, the method of producing indigo as described above is carried out for a time-period ranging from 24 hours to 240 hours.

In some embodiments, the method of producing indigo as described above is carried out for a time-period ranging from 24 hours to 120 hours.

In some embodiments, the method of producing indigo is carried out by a culturing mode selected from a group comprising batch culturing, fed-batch culturing, continuous culturing, and combinations thereof.

In some embodiments, the culturing of the recombinant methanotrophic bacterium is carried out at a temperature ranging from about 30° C. to 50° C., a pH ranging from about 3 to 8, for a time-period ranging from 24 hours to 240 hours, and by a culturing mode selected from a group comprising batch culturing, fed-batch culturing, continuous culturing, and combinations thereof.

In some embodiments, the growth of recombinant methanotrophic bacterial cells of the present disclosure under suitable culturing conditions facilitate formation of indigo from methane resulting in the microbial synthesis of isolatable quantities of indigo. In some embodiments, the present disclosure also describes optimization of the process of fermentation of recombinant methanotrophic bacterium in the presence of gaseous substrate (methane) to enhance the biomass and product (indigo) yield.

It will be understood by a person of ordinary skill in the art that any recombinant methanotrophic bacterium comprising the genes (target gene or gene of interest) described above can be suitably subjected to culturing at a temperature, pH values, time period, media concentrations, culturing mode and other process/culturing parameters, for indigo production.

While the aforementioned aspects have been described for methods of producing indigo from methane, each of the aforementioned aspects of said method are identically applicable for a method for producing indoxyl by culturing the recombinant methanotrophic bacterium described herein in presence of a methane source. Thus, in some embodiments, the present disclosure also provides a method for producing indoxyl from methane, comprising culturing the recombinant methanotrophic bacterium, said bacterium comprising:

a gene encoding enzyme for increasing concentration of indole; and a gene encoding enzyme for converting the indole to indoxyl, wherein the concentration of indole is increased by conversion of tryptophan to indole or by preventing formation of tryptophan from indole, or both.

Further, while indoxyl is known to readily undergo spontaneous dimerisation in presence of molecular oxygen to produce indigo, a skilled person will understand and know the techniques to isolate said indoxyl for industrial use/applications (prior to its conversion to indigo), and each of such techniques/methodologies to culture the recombinant methanotrophic bacterium and isolate indoxyl are within the purview of the present disclosure and claims.

The present disclosure further relates to use of a recombinant methanotrophic bacterium for production of indigo from methane, said bacterium comprising:

a gene encoding enzyme for increasing concentration of indole; and a gene encoding enzyme for converting the indole to indoxyl, wherein the concentration of indole is increased by conversion of tryptophan to indole, or by reducing or preventing formation of tryptophan from indole, or both.

In embodiments relating to the use of recombinant methanotrophic bacterium for production of indigo from methane, the features of said recombinant methanotrophic bacterium is according to the embodiments described above and is incorporated herein in its entirety.

While the aforementioned aspects have been described for use of the recombinant methanotrophic bacterium for conversion of methane to indigo, each of the aforementioned aspects of use are identically applicable for use of said recombinant methanotrophic bacterium for conversion of methane to indoxyl. Thus, in some embodiments, the present disclosure also provides use of a recombinant methanotrophic bacterium for production of indoxyl from methane, said bacterium comprising:

a gene encoding enzyme for increasing concentration of indole; and a gene encoding enzyme for converting the indole to indoxyl, wherein the concentration of indole is increased by conversion of tryptophan to indole, or by reducing or preventing formation of tryptophan from indole, or both.

Further, while indoxyl is known to readily undergo spontaneous dimerisation in presence of molecular oxygen to produce indigo, a skilled person will understand and know the techniques to isolate said indoxyl for industrial use/applications (prior to its conversion to indigo), and each of such techniques/methodologies to use the recombinant methanotrophic bacterium and isolate indoxyl are within the purview of the present disclosure and claims.

The present disclosure also provides a method of enhancing the production of indigo in a methanotrophic bacterium comprising: developing a recombinant methanotrophic bacterium as described herein; and culturing the recombinant methanotrophic bacterium in presence of a methane source.

In embodiments relating to the method of enhancing production of indigo in a methanotrophic bacterium, the features of developing a recombinant methanotrophic bacterium and culturing the recombinant methanotrophic bacterium are according to the embodiments described above and is incorporated herein in its entirety.

In some embodiments of the recombinant methanotrophic bacterium and methods of the present disclosure, the recombinant methanotrophic bacterium described herein produces at least about 0.01 g/L of indigo when compared to the corresponding wild-type methanotrophic bacterium which does not produce any indigo. In some embodiments, the recombinant methanotrophic bacterium of the present disclosure produces at least about 0.1 g/L of indigo when compared to the corresponding wild-type methanotrophic bacterium which does not produce any indigo. In some embodiments the recombinant methanotrophic bacterium of the present disclosure produces at least about 0.5 g/L of indigo when compared to the corresponding wild-type methanotrophic bacterium which does not produce any indigo. In some embodiments, the recombinant methanotrophic bacterium of the present disclosure produces about 0.01 g/L to about 50 g/L of indigo.

Thus, as shown in the above disclosure and embodiments, the approach of indigo biosynthesis described herein enables a greener and more sustainable solution for manufacturing indigo. The present disclosure simultaneously provides a solution to address the environmental concerns related to discharge of toxic byproducts that are produced during chemical synthesis of indigo, and at the same time utilizes methane (a powerful greenhouse gas with a global warming potential) to produce a valuable product such as indigo.

Additional embodiments and features of the present disclosure will be apparent to one of ordinary skill in art based on the description and embodiments provided herein. The embodiments herein provide various features and advantageous details thereof in the description. Descriptions of well-known/conventional methods and techniques are omitted so as to not unnecessarily obscure the embodiments herein. Further, the disclosure herein provides for examples illustrating the above described embodiments, and in order to illustrate the embodiments of the present disclosure certain aspects have been employed. The examples used herein for such illustration are intended merely to facilitate an understanding of ways in which the embodiments herein may be practiced and to further enable those of skill in the art to practice the embodiments herein. Accordingly, the following examples should not be construed as limiting the scope of the embodiments herein.

EXAMPLES

Biological Materials: The wild-type methanotrophic bacteria *Methylococcus capsulatus* was procured from Professor Colin Murrell at University of East Anglia, UK. *Methylomicrobium buryatense* used for transformation experiments was a gift from Dr. Yuri Trotsenko, at Pushchino Institute of Biochemistry and Physiology of Microorganisms, Russian Academy of Sciences, Russia. *E. coli* XL1-Blue and S17 strains for sourcing TnaA gene were a gift from Prof. Colin Murrell, University of East Anglia, UK. Wild-type TrpB gene was sourced from *Methylococcus capsulatus* which was obtained as mentioned above. Genes for FMO and IacA were codon optimized and chemically synthesized.

Example 1

Cloning of Indigo Pathway Genes into a Shuttle Vector

Indigo biosynthesis requires tryptophan as a precursor molecule. Tryptophan can be converted to indole by tryptophanase enzyme (TnaA). Alternatively, a mutant beta subunit of tryptophan synthase enzyme (mutant Trp B) can aid in indole accumulation. Indole thus formed can be converted to indoxyl in presence of a suitable oxygenase enzyme (eg. FMO) or a dehydrogenase (eg. IacA). The indoxyl molecule undergoes spontaneous dimerisation in presence of molecular oxygen producing indigo. Different sets of genes were generated to engineer recombinant methanotrophic strains for indigo production as listed in Table 1.

TABLE 1

Vectors for Indigo Biosynthesis

| Vector Name | Promoter | Gene encoding enzyme for increasing concentration of indole | Gene encoding enzyme for converting indole to indoxyl (Indole Oxidase genes) |
|---|---|---|---|
| VecA1 | ppqA (SEQ ID NO. 46) | TnaA (from *E. coli* XL1 Blue) (SEQ ID NO. 1) | FMO (from *Methylophaga aminisulfidivorans*) (SEQ ID NO. 5 - codon-optimized) |
| VecA2 | ppqA (SEQ ID NO. 46) | TnaA (from *E. coli* S17) (SEQ ID NO. 1) | FMO (from *Methylophaga aminisulfidivorans*) (SEQ ID NO. 5 - codon-optimized) |
| VecA3 | ppqA (SEQ ID NO. 46) | TrpB mutant (wild-type TrpB from *M. capsulatus*) (SEQ ID NO. 3) | FMO (from *Methylophaga aminisulfidivorans*) (SEQ ID NO. 5 - codon-optimized) |
| VecB1 | Hps (SEQ ID NO. 47) for TnaA Promoter ppqA (SEQ ID NO. 46) for IacA | TnaA (*E. coli* XL1 Blue) (SEQ ID NO. 1) | IacA (from *A. baumannii*) (SEQ ID NO. 7 - codon-optimized) |
| VecC1 | Hps (SEQ ID NO. 47) for TnaA Promoter ppqA (SEQ ID NO. 46) for IacA | TnaA (*E. coli* S17) (SEQ ID NO. 1) | IacA (from *A. baumannii*) (SEQ ID NO. 7 - codon-optimized) |

As shown in Table 1, to engineer recombinant strains for indigo production, Flavin-monooxygenase (FMO) gene from Methylophaga sp. was codon optimised (SEQ ID NO. 5) for expression in *Methylococcus capsulatus* Bath. All genes were synthesized and sequences were confirmed by nucleotide sequencing. FMO was PCR amplified with primers containing BamHI restriction sites on both ends. PCR amplified gene was cloned downstream to pyrroloquinoline quinone biosynthesis protein A (ppqA) gene promoter in a shuttle vector using sequence and ligation independent cloning (SLIC) method. The shuttle vector consisted of a kanamycin resistance gene cassette (SEQ ID NO. 50) as a selection marker. The shuttle vector backbone used for cloning the gene of interest and regulatory sequences is provided under SEQ ID NO. 27. Said vector backbone was suitably employed in all the present examples. Colonies were screened by performing PCR. The resultant vector vecA was verified using DNA sequencing.

Next, tryptophanase gene (TnaA) (SEQ ID NO. 1) from *E. coli* was amplified using genomic DNA from strains XL1-Blue and S-17. The TnaA genes were cloned downstream to FMO gene using SLIC method. The vectors thus generated were called vecA1 and vecA2 containing FMO gene along with TnaA genes from XL1-Blue (VecA1) and S-17 strain (VecA2), respectively.

The gene coding for beta subunit of tryptophan synthase (TrpB) enzyme was PCR amplified from genomic DNA of *Methylococcus capsulatus*. Said wild-type TrpB gene (SEQ ID NO. 25) was cloned in a commercially procured pET21a vector (https://www.snapgene.com/resources/plasmid-files/?-set=pet_and_duct_vectors_(novagen)&plasmid=pET-21a(%2B) at BamHI site using the SLIC method. The clone was confirmed by sequencing the vector. The vector generated was labelled vecC. Site-directed mutagenesis was performed on TrpB gene in vecC to introduce R389P and K392M double mutation in the coding region of the gene. The mutation was verified by sequencing. The generated mutant TrpB gene (SEQ ID NO. 3) was PCR amplified for cloning in vecA downstream to FMO gene using the SLIC method of cloning. The resulting vector vecA3 was verified by PCR and DNA sequencing. Accordingly, the indigo biosynthesis pathway was cloned under a constitutive ppqA promoter as an operon.

Another set of vectors using TnaA genes (SEQ ID NO. 1) from *E. coli* were generated. The TnaA genes were PCR amplified using genomic DNA from strains XL1-Blue and S-17 using primers containing BamHI restriction sites on both ends. The PCR amplified TnaA genes were cloned downstream to constitutive 3-hexulose-6-phosphate synthase (hps) gene promoter using the SLIC method of cloning. The resultant vectors, vecB and vecC containing TnaA gene from XL1-Blue and S-17 respectively were screened using PCR and verified by DNA sequencing.

Next, acyl-CoA dehydrogenase-like protein (IacA) from *Acinetobacter baumannii* was codon optimised (SEQ ID NO. 7) for *Methylococcus capsulatus*. IacA was PCR amplified with primers containing BamHI restriction sites on both ends. ppqA promoter containing shuttle vector was restriction digested using BamHI enzyme for cloning IacA gene. Clones were screened by PCR and confirmed by sequencing (vecD). Subsequently, ppqA promoter-IacA gene-T7 terminator cassette (SEQ ID NO. 46-SEQ ID NO. 7-SEQ ID NO. 32) was mobilised from vecD into vecB and vecC. The primers designed to amplify this promoter-gene-terminator cassette added FspI restriction sites on both ends of the PCR product. Vectors vecB and vecC were digested using FspI enzyme. PCR amplified ppqA promoter-iacA gene-T7 terminator cassette was cloned using the SLIC method. The resultant vectors vecB1 and vecC1 were verified by PCR and DNA sequencing.

Example 2

Indole/Indigo Production Using Recombinant *Methylococcus capsulatus*

Wild-type methanotrophs, such as *Methylococcus capsulatus* do not have the genes required for the conversion of indole to indigo. Hence, the native/wild-type methanotrophic bacteria strains do not produce any indigo.

For indigo production in recombinant methanotrophs, the relevant genes described in Example 1 were transformed into *M. capsulatus*. Said transformation into *M. capsulatus* was carried out by first transforming the desired plasmid to a host cell (*E. coli*), followed by transforming the genes in *M. capsulatus* from the *E. coli* transformants using conjugation technique (solid mating technique). The detailed procedure of transformation to obtain recombinant *M. capsulatus* is as follows:

*E. coli* XL1-Blue competent cells were separately transformed with vectors vecA1, vecA2, vecA3, vecB1 and vecC1 containing indigo biosynthetic pathway genes (Example 1). The transformants were selected by plating on Luria Bertani media plates supplemented with about 50 µg/ml kanamycin. One colony from each plate was inoculated in about 5 ml Luria Bertani media containing about 50 µg/ml kanamycin to generate a primary culture and incubated overnight in a shaker incubator at about 37° C. and about 180 rpm. Next day, about ml of sterile Luria Bertani media supplemented with tryptophan, glycerol and about 50 µg/ml kanamycin was inoculated with about 1% of the respective primary cultures. Flasks were incubated again in a shaker incubator for about 48 hours at about 37° C. and 180 rpm. Gradual change in colour of the media from yellow to blue of indigo was observed during the incubation. After about 48 hours of incubation, cells were pelleted by centrifugation at about 4,700 rpm for about 15 minutes. Cell pellets and media supernatants were analysed for indole and indigo production using HPLC analysis. In clones transformed with vecA1, vecA2 and vecA3, HPLC analysis revealed indole accumulation in the supernatant at levels up to 100 mg/L and blue colored indigo accumulation up to 80 mg/L in the pellets. Most of the indole was present in the supernatant. Further, clones transformed with vecB1 and vecC1 containing IacA gene, showed an indigo titre of 94 mg/L. Said results confirm the success of the present strategy of employing gene encoding enzyme for increasing concentration of indole (TnaA or mutant TrpB) and gene encoding enzyme for catalysing indole to indoxyl conversion (FMO or IacA), and thereby indigo production.

Bioreactor run was performed for *E. coli* XL1-Blue competent cells transformed with vecB1 comprising TnaA and IacA. The transformants were selected by plating on Luria Bertani media plates supplemented with about 50 µg/ml kanamycin. One colony from the transformation plate was inoculated in about 100 ml of sterile Luria Bertani media containing about 50 m/ml kanamycin to generate primary culture for a bioreactor run. The flask was incubated overnight at about 37° C. and about 180 rpm.

The recombinant strains were run in about 5000 ml non-jacketed bioreactor containing 4000 ml sterile Luria Bertani media supplemented with tryptophan, glycerol and about 50 µg/mlkanamycin. Entire primary culture of about 100 ml was inoculated in the reactor and grown for about 48 hours at about 37° C. with dissolved oxygen maintained at about 20%. Indigo production was visible by the change in colour of the reactor media from yellow to blue of indigo. After about 48 hours of reactor run, cells were harvested by centrifugation at about 6000 rpm for about 15 minutes at about 4° C. Cell pellets and media supernatant were analysed for indigo titre determination. HPLC analysis revealed an indigo titre of 115 mg/L.

The above indole and indigo production results substantiate that the genes (i.e. the gene encoding enzyme for increasing concentration of indole such as TnaA and mutant TrpB; and the gene encoding enzyme for converting the indole to indoxyl such as FMO and IacA) actively function to result in indole and indigo synthesis.

Based on the successful confirmation of the activity of target genes (TnaA, mutant TrpB, FMO and IacA) described above, wild-type *Methylococcus capsulatus* was now transformed with different indigo pathway clones generated in *E. coli* (i.e. *E. coli* transformants) using a solid mating protocol (conjugation technique). In this technique, transformation was initiated by plating a loopful of *M. capsulatus* cells on nitrate minimal salt (NMS) media plate supplemented with about 0.02% protease peptone. Plates were incubated at about 37° C. for about 24 to 48 hours in an anaerobic jar fed with methane. *E. coli* S17 competent cells transformed with vectors of interest were incubated overnight at about 37° C. Next day, a loopful of *E. coli* transformants (comprising vectors vecA1, vecA2, vecA3, vecB1, vecC1, vecB and vecC) were uniformly spread on *M. capsulatus* containing NMS-protease peptone media plates. Plates were incubated at about 37° C. for about 48 hours in an anaerobic jar fed with methane. After about 48 hours of incubation, a loopful of culture from NMS-protease peptone plate was spread on NMS plates supplemented with kanamycin for selection of transformants. Plates were incubated at about 45° C. in an anaerobic jar fed with methane. Colonies appearing after 5 to 6 days of transformation were screened by PCR and further verified using DNA sequencing. Confirmed transformant colonies were patched on NMS-kanamycin plates and incubated at about 45° C. in an anaerobic jar containing methane for about 3 to 4 days or till the complete visible growth of the patch.

For growth studies, primary culture was generated by inoculating a loopful of culture from each transformant in about 20 ml sterile NMS media supplemented with 30 µg/ml of kanamycin. Flasks were sealed using sterile suba seals and about 20% v/v methane was fed in the flasks. Flasks were incubated at about 45° C. for about 12 to 16 hours at about 160 rpm. Next day, in 500 ml flasks containing about 100 ml sterile NMS media supplemented with about 30 µg/ml of kanamycin was inoculated with the primary culture. Flasks were sealed and methane feeding was performed. Cultures were incubated at about 45° C. for as mentioned about 24 to 72 hours at about 160 rpm. Post incubation, cells were pelleted by centrifugation at about 4,700 rpm for about 15 minutes. Cell pellets and media supernatants were analysed to confirm the presence of indole and indigo from recombinant *Methylococcus capsulatus* cells, and were subjected to further determination of the titres of said compounds.

Example 3

Bioreactor Run (Batch Fermentation) for Indole/Indigo Production in Recombinant *M. capsulatus* Expressing Indigo Biosynthesis Pathway Genes

*Methylococcus capsulatus* cells were transformed with vector vecB1 harboring TnaA and IacA genes. The same procedure as outlined under Example 2 was followed to obtain transformed *M. capsulatus* cells. Transformants were patched on a fresh NMS plate containing kanamycin for selection of transformants. Primary culture was prepared by inoculation of about 100 ml sterile NMS media supplemented with 30 μg/ml kanamycin with a loopful of recombinant *M. capsulatus* containing vecB1. Flask was sealed using suba seal and about 20% v/v methane was fed in the flask as a sole carbon source for growth. Flask was incubated at about 45° C. for about 12 to 16 hours at about 160 rpm. Next day, cells from primary culture was used as inoculum for about 200 ml NMS media. Flasks were sealed and methane feeding and incubation was performed as mentioned above. The secondary culture generated was used as an inoculum for batch fermentation in bioreactor.

In a 5 L reactor, about 3000 ml sterile NMS media supplemented with 30 μg/ml kanamycin was inoculated with about 1000 ml of secondary culture. The reactor temperature was maintained at about 45° C. throughout the reactor run. About 0.1 to 0.2 lpm (litres per minute) of methane gas was fed into the reactor. The dissolved oxygen level was maintained between 15 to 20%. pH of the media was maintained by addition of acid and base solutions. Anti-foam was added as and when required. The reactor was run in batch mode for about 72 hours. At the end of the run, cells were harvested by centrifugation at about 6000 rpm for about 15 minutes at about 4° C. Cell pellets and media supernatants were analysed to confirm the presence of indole and indigo from recombinant *Methylococcus capsulatus* cells, and were subjected to further determination of the titres of said compounds.

Example 4

Indole/Indigo Production Using Recombinant *Methylomicrobium buryatense*

*Methylomicrobium buryatense* cells were transformed with vectors containing indigo biosynthesis pathway genes (vectors—vecA1, vecA2, vecA3, vecB1, vecC1, vecB and vecC). The transformations were performed using the solid mating technique as described below. Wild type *M. buryatense* strain was spread in DSMZ media and incubated in anaerobic jar fed with methane. The anaerobic jar was incubated at about 30° C. for about 24 to 48 hours. A loopful of *M. buryatense* was spread on to mating plate (DSMZ media with 15% nutrient agar) and further incubated at about 30° C. for about 24 hours. After the incubation period, a loopful of *E. coli* containing appropriate vector was spread onto mating plate containing *M. buryatense* and incubated at about 30° C. for about 48 hours. For selecting recombinant *M. buryatense*, a loopful of cells from mating plate was spread on to DSMZ media with about 30 mg/l kanamycin. Recombinant clones were confirmed by PCR and restriction digestion.

For growth studies, primary culture was generated by inoculating a loopful of culture from each transformant in about 20 ml sterile DSMZ media supplemented with about 30 μg/ml of kanamycin. Flasks were sealed using sterile suba seals and about 20% v/v methane was fed in the flasks. Flasks were incubated at about 45° C. for about 12 to 16 hours at about 160 rpm. Next day, 500 ml flasks containing 100 ml sterile DSMZ media supplemented with about 30 μg/ml of kanamycin was inoculated with the primary culture. Flasks were sealed and methane feeding was performed as mentioned before. Cultures were incubated at about 45° C. for about 48 to 50 hours at about 160 rpm. Post incubation, cells were pelleted by centrifugation at about 4,700 rpm for about 15 minutes. Cell pellets and media supernatants were analysed to confirm the presence of indole and indigo from recombinant *Methylococcus buryatense* cells, and were subjected to further determination of the titres of said compounds.

Example 5

Overexpression of Shikimic Acid Pathway Genes and Effect on Indigo Production

Shikimic acid pathway provides flux for aromatic amino acid biosynthesis pathway. Hence, shikimic acid biosynthesis pathway enzymes were overexpressed to improve the intracellular levels of chorismate and aromatic amino acids like tryptophan. Genes aroA, aroC, aroK, aroE, aro Q, DAHP synthase and aroB were PCR amplified from genomic DNA of *Methylococcus capsulatus*. The aroF gene from *Escherichia coli* strains XL1-Blue and S-17 was PCR amplified using respective genomic DNAs. Each of the PCR amplified genes aroA (SEQ ID NO. 21), aroC (SEQ ID NO. 23), aroK (SEQ ID NO. 19), aroE (SEQ ID NO. 17), DAHP synthase (SEQ ID NO. 9), aroB (SEQ ID NO. 13) and aroF (SEQ ID NO. 11) was cloned downstream to constitutive formaldehyde activating enzyme 2 (fae2) gene promoter at BamHI site using the SLIC method of cloning (as explained in Example 1). Clones were verified by PCR and DNA sequencing.

Next, each 'fae2 promoter-GeneX-T7 terminator' cassette comprising one or more genes (Gene X) selected from aroD, aroA, aroC, aroK, aroE, DAHP synthase, aroB and aroF was PCR amplified and cloned into vecA1 (harboring TnaA and FMO genes) at the NarI site using the SLIC method. Clones were confirmed by performing PCR and DNA sequencing.

The above developed vector comprising TnaA, FMO, aroA, aroC, aroK, aroE, aroD, DAHP synthase, aroB and aroF genes was transformed in *E. coli* similar to the protocol described in Example 2. The *E. coli* transformants were used to conjugate the vector into *M. capsulatus*. The recombinant *M. capsulatus* strains with the overexpressed genes were analyzed for increase in indigo and indole production. Cell pellets and media supernatants were analysed using HPLC analysis to confirm the presence of indole and indigo from recombinant *Methylococcus capsulatus* cells, and were subjected to further determination of the titres of said compounds.

Example 6

Knock-Down of trpR and Effect on Indigo Production

Tryptophan is a precursor for indigo formation. TrpR protein (Trp operon repressor) encoded in the genome of *E. coli* regulates the intracellular levels of tryptophan and few other amino acids. It was hypothesized that the knock-down or deletion of the trpR gene can increase the intracellular free tryptophan levels. Higher tryptophan levels can lead to higher levels of indole and indigo. Tryptophan can be converted to indole by TnaA which can feed into indigo biosynthesis pathway and consequently increase the indigo titre.

Deletion of trpR gene (SEQ ID NO. 61) was carried out by replacing it with ampicillin resistance gene cassette from pUC57. Ampicillin resistance gene cassette was amplified using primers with 50 bp homology to upstream and downstream sequences of trpR coding region. The PCR amplified cassette was gel purified. *E. coli* XL1-Blue competent cells were transformed with the purified ampicillin resistance gene cassette. After 3 hours of recovery in Luria Bertani media, cells were plated on LB plates supplemented with about 100 µg/ml ampicillin. Plates were incubated overnight at about 37° C. Colonies were screened by PCR and verified by genomic DNA sequencing to select *E. coli* deltrpR cells (i.e. cells with trpR deleted). The *E. coli* deltrpR cells were used for transforming plasmids containing indigo biosynthesis pathway genes.

*E. coli* deltrpR competent cells were transformed with vectors vecA1, vecA2, vecA3, vecB1 and vecC1 in individual experiments. Transformation of vectors in *E. coli* was performed as described in Example 2. Transformants were selected on LB agar plates containing about 50 µg/ml kanamycin. Recombinant *E. coli* cells containing the genomic copy of trpR and transformed with above mentioned vectors were used as controls to compare the changes in indigo yields. One colony from each plate was inoculated in about ml Luria Bertani media containing about 50 µg/ml kanamycin to generate a primary culture and incubated overnight at about 37° C. and about 180 rpm. Next day, about 20 ml of sterile Luria Bertani media supplemented with about 2% glycerol and about 50 µg/ml kanamycin was inoculated with about 1% of the respective primary cultures. Flasks were incubated for about 48 hours at about 37° C. and about 180 rpm. Gradual change in colour of the media from yellow to blue of indigo was observed during the incubation. After about 48 hours of incubation, cells were pelleted by centrifugation at about 4,700 rpm for 15 minutes. Cell pellets and media supernatants were analysed using HPLC analysis to confirm the presence of indole and indigo, and were subjected to further determination of the titres of said compounds. Accordingly, a similar recombinant methanotrophic bacterium is obtained with deletion of tryptophan operon regulator gene(s) and transformation with individual vectors vecA1, vecA2, vecA3, vecB1 and vecC1.

Example 7

Analysis of Transcript Levels of Indigo Pathway Genes

Recombinant *Methylococcus capsulatus* cells containing individual vectors vecA1, vecA2, vecA3, vecB1 and vecC1 with indigo pathway genes were grown in about 20 ml NMS media supplemented with 30 µg/ml of kanamycin and about 20% v/v methane for about 48 hours at about 45° C. and about 160 rpm. Cells were harvested by centrifugation at about 4,700 rpm for about 15 minutes. Total RNA was extracted using TRI reagent as per manufacturer's instructions. DNase treatment was performed to remove DNA contamination from RNA samples. About 2 µg of DNase treated RNA was used for cDNA synthesis as per manufacturer's instructions (Takara—PrimeScript 1st strand cDNA Synthesis kit). cDNA was used for the next round of semi-quantitative PCR amplification for full length TnaA, TrpB, FMO and IacA genes. PCR samples were gel electrophoresed and visualized in gel documentation unit. Bands were observed at expected sizes for full length TnaA, TrpB, FMO and IacA genes in recombinant clones indicating a functional pathway for indigo biosynthesis in *M. capsulatus*. Said results further indicate the capability of the recombinant *M. capsulatus* to produce indigo.

*Methylococcus capsulatus* and *Methylomicrobium buryatense* are model methanotrophic bacteria which share similar biochemical pathways to other methanotrophic bacteria. Hence, a successful metabolic engineering of these model methanotrophic bacteria to produce indole and indigo can be used for other methanotrophic bacteria. Accordingly, the successful development of recombinant *Methylococcus capsulatus* and *Methylomicrobium buryatense* comprising indigo biosynthesis pathway genes and the functionality/activity of said indigo biosynthesis genes as shown in the above examples indicate that other methanotrophs such as *Methylomicrobium alcaliphilum*, *Methylomicrobium kenyanse*, *Methylomicrobium album*, *Methylocapsa acidiphila*, *Methylocella silvestris*, *Methylosinus trichosporium*, *Methylacidiphilum infernorum* V4, *Methylomonas methanica*, *Methylosinus sporium*, *Methylocella palustris*, *Methylocystis parvus*, *Methylovulum miyakonense*, *Methylocystis echinoides*, *Methylomonas rubra*, *Methylococcus thermophilus*, *Methylomonas aurantiaca*, *Methylomonas fodinarum*, *Methylomicrobium japanense* and *Methylococcaceae bacterium* comprising shikimate metabolic pathway for biosynthesis of aromatic amino acids (phenylalanine, tyrosine, and tryptophan) can be similarly genetically engineered for indigo biosynthesis.

As regards all the embodiments/examples characterized in this specification, in particular in the claims, it is intended that each embodiment mentioned in a dependent claim is combined with each embodiment of each claim (independent or dependent) said dependent claim depends from. As an example, in case of an independent claim 1 reciting 3 alternatives A, B and C, a dependent claim 2 reciting 3 alternatives D, E and F and a claim 3 depending from claims 1 and 2 and reciting 3 alternatives G, H and I, it is to be understood that the specification unambiguously discloses embodiments corresponding to combinations: A, D, G; A, D, H; A, D, I; A, E, G; A, E, H; A, E, I; A, F, G; A, F, H; A, F, I; B, D, G; B, D, H; B, D, I; B, E, G; B, E, H; B, E, I; B, F, G; B, F, H; B, F, I; C, D, G; C, D, H; C, D, I; C, E, G; C, E, H; C, E, I; C, F, G; C, F, H; and C, F, I, unless specifically mentioned otherwise.

Similarly, and also in those cases where independent and/or dependent claims do not recite alternatives, it is understood that if dependent claims refer back to a plurality of preceding claims or plurality of embodiments, any combination of subject-matter covered thereby is considered to be explicitly disclosed. For example, in case of an independent claim 1, a dependent claim 2 referring back to claim 1, and a dependent claim 3 referring back to both claims 2 and 1, it follows that the combination of the subject-matter of claims 3 and 1 is clearly and unambiguously disclosed as is the combination of the subject-matter of claims 3, 2 and 1. In case a further dependent claim 4 is present which refers to anyone of claims 1 to 3, it follows that the combination of the subject-matter of claims 4 and 1, of claims 4, 2 and 1, of claims 4, 3 and 1, as well as of claims 4, 3, 2 and 1 is clearly and unambiguously disclosed.

The above considerations apply mutatis mutandis to all claims and embodiments of the present specification. To give a few examples, the combination of claims 3, 5 and 1 is clearly and unambiguously envisaged in view of the claim structure/claimed subject-matter. The same applies for the combinations of claims 12, 10, 3 and 5, and, to give a few further examples which are not limiting, the combination of claims 14, 13, 9 and 8 and the combination of claims 13, 9 and 8.

The foregoing description of the specific embodiments and examples reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments in this disclosure have been described in terms of preferred embodiments, those skilled in the art will recognize that the embodiments herein can be practiced with modification within the spirit and scope of the embodiments as described herein.

Throughout this specification, the word "comprise", or variations such as "comprises" or "comprising" or "including" wherever used, will be understood to imply the inclusion of a stated element, integer or step, or group of elements, integers or steps, but not the exclusion of any other element, integer or step, or group of elements, integers or steps. Additionally, throughout the specification, "a group comprising" of a particular stated element, integer or step, or group of elements, integers or steps also envisages "a group consisting" of said stated element, integer or step, or group of elements, integers or steps without inclusion of any other element, integer or step, or group of elements, integers or steps.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

Any discussion of documents, acts, materials, devices, articles and the like that has been included in this specification is solely for the purpose of providing a context for the disclosure. It is not to be taken as an admission that any or all of these matters form a part of the prior art base or were common general knowledge in the field relevant to the disclosure as it existed anywhere before the priority date of this application.

While considerable emphasis has been placed herein on the particular features of this disclosure, it will be appreciated that various modifications can be made, and that many changes can be made in the preferred embodiments without departing from the principles of the disclosure. These and other modifications in the nature of the disclosure or the preferred embodiments will be apparent to those skilled in the art from the disclosure herein, whereby it is to be distinctly understood that the foregoing descriptive matter is to be interpreted merely as illustrative of the disclosure and not as a limitation.

We claim:

1. A recombinant methanotrophic bacterium capable of producing indigo from methane, comprising:
   - a heterologous gene encoding tryptophanase (TnaA) enzyme or mutant beta subunit of tryptophan synthase (mutant TrpB) enzyme, or both, for increasing concentration of indole; and
   - a heterologous gene encoding flavin-containing monooxygenase (FMO) or acyl-CoA dehydrogenase-like protein (lacA) enzyme, or both, for converting the indole to indoxyl, wherein the concentration of indole is increased by:
   a) conversion of tryptophan to indole, or
   b) reducing or preventing formation of tryptophan from indole, or
   both a) and b).

2. The recombinant methanotrophic bacterium as claimed in claim 1, wherein the concentration of indole is increased in the recombinant methanotrophic bacterium by at least five fold compared to a corresponding wild-type methanotrophic bacterium;

and wherein said increase in concentration of indole is caused by overexpression, codon optimization, mutation or any combination thereof, of said gene.

3. The recombinant methanotrophic bacterium as claimed in claim 1, wherein the conversion of tryptophan to indole is facilitated by TnaA; and the formation of tryptophan from indole is reduced or prevented by mutant TrpB.

4. The recombinant methanotrophic bacterium as claimed in claim 1, wherein the gene encoding enzyme for converting the indole to indoxyl is an oxidase or a dehydrogenase, or a combination thereof;
and wherein the oxidase is a flavin-containing monooxygenase (FMO), and the dehydrogenase is acyl-CoA dehydrogenase-like protein (IacA).

5. The recombinant methanotrophic bacterium as claimed in claim 1, wherein the gene encoding enzyme for converting the indole to indoxyl is a gene encoding flavin-containing monooxygenase (FMO), or a gene encoding acyl-CoA dehydrogenase-like protein (IacA), or a combination thereof.

6. The recombinant methanotrophic bacterium as claimed in claim 1, wherein the gene is a heterologous gene; and wherein the heterologous gene is either unmodified, codon-optimized, mutated, or any combination thereof; and
wherein the heterologous gene is sourced from bacteria, plant, yeast, or any combination thereof.

7. The recombinant methanotrophic bacterium as claimed in claim 3, wherein the TnaA comprises a nucleic acid sequence set forth as SEQ ID NO. 1 or a nucleic acid sequence having at least 80% identity to SEQ ID NO. 1, and a corresponding amino acid sequence set forth as SEQ ID NO. 2 or an amino acid sequence having at least 80% identity to SEQ ID NO. 2; and
the mutant TrpB comprises a nucleic acid sequence set forth as SEQ ID NO. 3 or a nucleic acid sequence having at least 80% identity to SEQ ID NO. 3, and a corresponding amino acid sequence set forth as SEQ ID NO. 4 or an amino acid sequence having at least 80% identity to SEQ ID NO. 4.

8. The recombinant methanotrophic bacterium as claimed in claim 5, wherein the FMO comprises a nucleic acid sequence set forth as SEQ ID NO. 5 or a nucleic acid sequence having at least 80% identity to SEQ ID NO. 5, and a corresponding amino acid sequence set forth as SEQ ID NO. 6 or an amino acid sequence having at least 80% identity to SEQ ID NO. 6; and
the lacA comprises a nucleic acid sequence set forth as SEQ ID NO. 7 or a nucleic acid sequence having at least 80% identity to SEQ ID NO. 7, and a corresponding amino acid sequence set forth as SEQ ID NO. 8 or an amino acid sequence having at least 80% identity to SEQ ID NO. 8.

9. The recombinant methanotrophic bacterium as claimed in claim 1, wherein the recombinant methanotrophic bacterium comprises an overexpressed gene, said overexpressed gene selected from the group consisting of 3-Deoxy-D-arabinoheptulosonate 7-phosphate synthase (DAHP synthase), Phospho-2-dehydro-3-deoxyheptonate aldolase (AroF), 3-Dehydroquinate synthase (AroB), 3-dehydroquinate dehydratase (AroD), Shikimate dehydrogenase (AroE), Shikimate kinase (AroK), 3-Phosphoshikimate1-carboxyvinyltransferase (AroA), Chorismate synthase (AroC), and combinations thereof;
and wherein the overexpression of the gene is achieved by altering promoter strength of native gene of methanotrophic bacterium selected from the group consisting of DAHP Synthase, AroF, AroB, AroD, AroE, AroK, AroA, AroC and combinations thereof, or the overexpression of the gene is achieved by transforming a gene selected from the group consisting of DAHP Synthase, AroF, AroB, AroD, AroE, AroK, AroA, AroC, and combinations thereof, and wherein the transformed gene is a gene native to methanotrophic bacterium, or is a heterologous gene;
and wherein the native gene, the heterologous gene or both are either unmodified, codon-optimized, mutated or any combination thereof.

10. The recombinant methanotrophic bacterium as claimed in claim 9, wherein the gene encoding DAHP synthase comprises a nucleic acid sequence set forth as SEQ ID NO. 9 or a nucleic acid sequence having at least 80% identity to SEQ ID NO. 9, and a corresponding amino acid sequence set forth as SEQ ID NO. 10 or an amino acid sequence having at least 80% identity to SEQ ID NO. 10;
the gene encoding AroF comprises a nucleic acid sequence set forth as SEQ ID NO. 11 or a nucleic acid sequence having at least 80% identity to SEQ ID NO. 11, and a corresponding amino acid sequence set forth as SEQ ID NO. 12 or an amino acid sequence having at least 80% identity to SEQ ID NO. 12;
the gene encoding AroB comprises a nucleic acid sequence set forth as SEQ ID NO. 13 or a nucleic acid sequence having at least 80% identity to SEQ ID NO. 13, and a corresponding amino acid sequence set forth as SEQ ID NO. 14 or an amino acid sequence having at least 80% identity to SEQ ID NO. 14;
the gene encoding AroD comprises a nucleic acid sequence set forth as SEQ ID NO. 15 or a nucleic acid sequence having at least 80% identity to SEQ ID NO. 15, and a corresponding amino acid sequence set forth as SEQ ID NO. 16 or an amino acid sequence having at least 80% identity to SEQ ID NO. 16;
the gene encoding AroE comprises a nucleic acid sequence set forth as SEQ ID NO. 17 or a nucleic acid sequence having at least 80% identity to SEQ ID NO. 17, and a corresponding amino acid sequence set forth as SEQ ID NO. 18 or an amino acid sequence having at least 80% identity to SEQ ID NO. 18;
the gene encoding AroK comprises a nucleic acid sequence set forth as SEQ ID NO. 19 or a nucleic acid sequence having at least 80% identity to SEQ ID NO. 19, and a corresponding amino acid sequence set forth as SEQ ID NO. 20 or an amino acid sequence having at least 80% identity to SEQ ID NO. 20;
the gene encoding AroA comprises a nucleic acid sequence set forth as SEQ ID NO. 21 or a nucleic acid sequence having at least 80% identity to SEQ ID NO. 21, and a corresponding amino acid sequence set forth as SEQ ID NO. 22 or an amino acid sequence having at least 80% identity to SEQ ID NO. 22; or
the gene encoding AroC comprises a nucleic acid sequence set forth as SEQ ID NO. 23 or a nucleic acid sequence having at least 80% identity to SEQ ID NO. 23, and a corresponding amino acid sequence set forth as SEQ ID NO. 24 or an amino acid sequence having at least 80% identity to SEQ ID NO. 24.

11. The recombinant methanotrophic bacterium as claimed in claim 1, wherein the recombinant methanotrophic bacterium comprises a knocked-down gene, said knocked-down gene selected from the group consisting of tryptophan operon regulator, tyrosine aminotransferase, aspartate aminotransferase and combinations thereof;
wherein the gene encoding a tryptophan operon regulator comprises a nucleic acid sequence having at least 80% identity to SEQ ID NO. 30, and a corresponding amino acid sequence having at least 80% identity to SEQ ID NO. 31;

the gene encoding tyrosine aminotransferase comprises a nucleic acid sequence having at least 80% identity to SEQ ID NO. 59, and a corresponding amino acid sequence having at least 80% identity to SEQ ID NO. 60;

or the gene encoding aspartate aminotransferase comprises a nucleic acid sequence set forth as SEQ ID NO. 34 or a nucleic acid sequence having at least 80% identity to SEQ ID NO. 34, and a corresponding amino acid sequence set forth as SEQ ID NO. 35 or an amino acid sequence having at least 80% identity to SEQ ID NO. 35.

12. The recombinant methanotrophic bacterium as claimed in claim 1, wherein the recombinant methanotrophic bacterium is selected from the group consisting of *Methylococcus capsulatus, Methylomicrobium buryatense, Methylomicrobium alcaliphilum, Methylomicrobium kenyanse, Methylomicrobium album, Methylocapsa acidiphila, Methylocella silvestris, Methylosinus trichosporium, Methylacidiphilum infernorum V4, Methylomonas methanica, Methylosinus sporium, Methylocella palustris, Methylocystis parvus, Methylovulum miyakonense, Methylocystis echinoides, Methylomonas rubra, Methylococcus thermophilus, Methylomonas aurantiaca, Methylomonas fodinarum, Methylomicrobium japanense* and *Methylococcaceae bacterium*.

13. The recombinant methanotrophic bacterium as claimed in claim 1, wherein the recombinant methanotrophic bacterium comprises a gene encoding tryptophanase (TnaA) and a gene encoding flavin-containing monooxygenase (FMO); or the recombinant methanotrophic bacterium comprises a gene encoding tryptophanase (TnaA) and a gene encoding acyl-CoA dehydrogenase-like protein (IacA); or the recombinant methanotrophic bacterium comprises a gene encoding mutant beta subunit of tryptophan synthase (mutant TrpB) and a gene encoding flavin-containing monooxygenase (FMO); or the recombinant methanotrophic bacterium comprises a gene encoding mutant beta subunit of tryptophan synthase (mutant TrpB) and a gene encoding acyl-CoA dehydrogenase-like protein (IacA); or the recombinant methanotrophic bacterium comprises a gene encoding tryptophanase (TnaA), a gene encoding mutant beta subunit of tryptophan synthase (mutant TrpB) and a gene encoding acyl-CoA dehydrogenase-like protein (IacA); or the recombinant methanotrophic bacterium comprises a gene encoding tryptophanase (TnaA), a gene encoding mutant beta subunit of tryptophan synthase (mutant TrpB) and a gene encoding flavin-containing monooxygenase (FMO).

14. The recombinant methanotrophic bacterium as claimed in claim 1, wherein the recombinant methanotrophic bacterium comprises:
a gene selected from TnaA, mutant TrpB, and a combination thereof;
a gene selected from FMO, IacA, and a combination thereof; and
a gene selected from an overexpressed gene, or a combination thereof, wherein the overexpressed gene is selected from the group consisting of DAHP Synthase, AroF, AroB, AroD, AroE, AroK, AroA, AroC, and combinations thereof, and the knocked-down gene is selected from the group consisting of tryptophan operon regulator, tyrosine aminotransferase, asparatate aminotransferase and combinations thereof.

15. The recombinant methanotrophic bacterium as claimed in claim 14, wherein the TnaA gene is sourced from *E. coli*, the TrpB gene is sourced from *Methylococcus capsulatus*, the FMO gene is sourced from *Methylophaga aminisulfidivorans* and the IacA gene is sourced from *Acinetobacter baumannii*.

16. A process for producing indigo from methane, comprising culturing the recombinant methanotrophic bacterium as claimed in claim 1, in presence of a methane source.

17. The process as claimed in claim 16, wherein the methane is a carbon and energy source for the recombinant methanotrophic bacterium;
the methane source is selected from the group consisting of pure methane, biogas, natural gas, landfill gas, organic waste, any source comprising methane and combinations thereof;
the culturing of the recombinant methanotrophic bacterium is carried out at a temperature ranging from about 30° C. to 50° C., a pH ranging from about 3 to 8, and for a time-period ranging from 24 hours to 240 hours, wherein culturing mode is selected from the group consisting of batch culturing, fed batch culturing, continuous culturing and combinations thereof;
or wherein the recombinant methanotrophic bacterium during the process produces at least about 0.01 g/L of indigo when compared to corresponding wild-type methanotrophic bacterium which does not produce any indigo.

* * * * *

SEQUENCE LISTING

```
<160> NUMBER OF SEQ ID NOS: 60

<210> SEQ ID NO 1
<211> LENGTH: 1416
<212> TYPE: DNA
<213> ORGANISM: Escherichia coli
<220> FEATURE:
<221> NAME/KEY: misc_feature
<223> OTHER INFORMATION: TnaA Gene- Escherichia coli strain K-12 (XL1-
      Blue/S17-1)

<400> SEQUENCE: 1
atggaaaact ttaaacatct ccctgaaccg ttccgcattc gtgttattga gccagtaaaa        60
cgtaccactc gcgcttatcg tgaagaggca attattaaat ccggtatgaa cccgttcctg       120
ctggatagcg aagatgtttt tatcgattta ctgaccgaca gcggcaccgg ggcggtgacg       180
cagagcatgc aggctgcgat gatgcgcggc gacgaagcct acagcggcag tcgtagctac       240
tatgcgttag ccgagtcagt gaaaaatatc tttggttatc aataccaccat tccgactcac      300 cagggccgtg gcgcagagca aatctatatt ccggtactga ttaaaaaacg cgagcaggaa       360
aaaggcctgg atcgcagcaa aatggtggcg ttctctaact atttctttga taccacgcag       420
ggccatagcc agatcaacgg ctgtaccgtg cgtaacgtct atatcaaaga agccttcgat       480
acgggcgtgc gttacgactt taaaggcaac tttgaccttg agggattaga acgcggtatt       540
gaagaagttg gtccgaataa cgtgccgtat atcgttgcaa ccatcaccag taactctgca       600
ggtggtcagc cggtttcact ggcaaactta aaagcgatgt acagcatcgc gaagaaatac       660
```

```
gatattccgg tggtaatgga ctccgcgcgc tttgctgaaa acgcctatttt catcaagcag    720 cgtgaagcag aatacaaaga ctggaccatc gagcagatca cccgcgaaac ctacaaatat    780
gccgatatgc tggcgatgtc cgccaagaaa gatgcgatgg tgccgatggg cggcctgctg    840
tgcatgaaag acgacagctt ctttgatgtg tacaccgagt gcagaaccct ttgcgtggtg    900
caggaaggct tcccgacata tggcggcctg aaggcggcg cgatggagcg tctggcggta    960
ggtctgtatg acggcatgaa tctcgactgg ctggcttatc gtatcgcgca ggtacagtat   1020
ctggtcgatg gtctggaaga gattggcgtt gtctgccagc aggcgggcgg tcacgcggca   1080
ttcgttgatg ccgtaaaact gttgccgcat atcccggcag accagttccc ggcacaggcg   1140
ctggcctgcg agctgtataa agtcgccggt atccgtgcgg tagaaattgg ctctttcctg   1200
ttaggccgcg atccgaaaac cggtaaacaa ctgccatgcc cggctgaact gctgcgttta   1260
accattccgc gcgcaacata tactcaaaca catatggact tcattattga agcctttaaa   1320
catgtgaaag agaacgcggc gaatattaaa ggattaacct ttacgtacga accgaaagta   1380
ttgcgtcact tcaccgcaaa acttaaagaa gtttaa                             1416
```

<210> SEQ ID NO 2
<211> LENGTH: 173
<212> TYPE: PRT
<213> ORGANISM: Escherichia coli
<220> FEATURE:
<221> NAME/KEY: MOD_RES
<222> LOCATION: (1)..(173)
<223> OTHER INFORMATION: TnaA Gene- Escherichia coli strain K-12 (XL1-
      Blue/S17-1)

<400> SEQUENCE: 2

Met Leu Arg Ala Glu Trp Leu Asn Ala Ala Val Gln Pro Gly Met Ala
1               5                   10                  15

Val Val Tyr Arg Phe Ser Asp Arg Gly Leu Thr Gly Lys Ser Gln Phe
                20                  25                  30

Leu Pro His Gly Tyr Arg Arg Leu Tyr Thr Ala Arg Arg Pro Ala Pro
            35                  40                  45

Val Pro Gly Thr Gly Leu Pro Gly Tyr Ala Ala Thr Val Tyr Arg His
        50                  55                  60

Gln Arg Met Pro Arg Asp Arg Pro Ala Gly Arg Gln Arg Gln Ser
65                  70                  75                  80

Leu Pro Asp His Arg Pro Asp Thr Val Pro Ala Arg Tyr Asp Lys Pro
                85                  90                  95

Ala Ser Arg Asp Ser Cys Arg His Thr Asp Leu Pro Pro Asp Ala Pro
            100                 105                 110

Ser Arg Arg Leu Pro Gly Arg His Met Ser Gly Ser Leu Pro Ala Pro
        115                 120                 125

Arg Lys Gly Phe Cys Thr Arg Cys Thr His Gln Arg Ser Cys Arg Leu
    130                 135                 140

Ser Cys Thr Ala Gly Arg Pro Ser Ala Pro Ser His Leu Ser Trp Arg
145                 150                 155                 160

Thr Ser Pro Ala Tyr Arg His Ile Cys Arg Phe Arg Gly
                165                 170

<210> SEQ ID NO 3
<211> LENGTH: 1212
<212> TYPE: DNA
<213> ORGANISM: Artificial Sequence
<220> FEATURE:

<223> OTHER INFORMATION: mutant TrpB gene (R389P K392M mutant)

<400> SEQUENCE: 3

```
atgcaagacg agattcagcc ctatgacctg cccgatgagc tcggccactt tggaccttac      60
ggtggcattt tcgtcgccga gaccttgatg gagccgctgg aagagctgaa agccgcctac     120
catcgctacc tgaaggaccc ggaattcctc gccgagctgg atcacgatct gaaccactac     180
gtcggccgcc cctcaccgat ctaccatgcc gaacgcctga gccgggagct cggcggcgca     240
cagatcttct tcaagcgcga agatctcaat cataccggtg cacacaaggt caacaacacc     300
gtcggccagg cactgctggc caagcgcatg ggcaagcggc gggtgatcgc cgagaccggt     360
gccggccagc acggcgtggc cacggccacc gtggcggccc ggctggggat ggagtgcgtg     420
gtctacatgg gggcggtcga cgtccagcgc caggcgctca acgtattccg catgaagctg     480
ctcggcgcca ccgtgatagc ggtcgactcg ggttcccgga cgctcaagga cgcgctgaac     540
gaagccatgc gcgactgggt gaccaacgtc gacgatacct tctacatcat cggtacggtg     600
gcgggtcccc atccctatcc cgccatggtg cgcgatttcc aggccgtgat cggccgcgag     660
gcgcgccggc agatgctgga gatgacgggg cgtctgcccg atgccctggt cgcctgcgtg     720
ggcggcggct cgaatgccat cggcctgttt catccgttcg tcgatgaccg cgaggtcgcc     780
atgtacgggg tcgaggccgc cggggatggt atcgaaaccg gtcgccactc ggctccgctg     840
agcgccggcc gccccggcgt gctgcacggc aaccgtacct acctgatgga agacgaagac     900
ggcgagatca tcgagaccca ttccattttcc gccgggctgg actatccggg cgtcgggccg     960
gaacacgcct ggctcaagga ctgcggccgg gcgagctatg tcagtgccac cgacgccgaa    1020
gcgctcgagg cgttccatat cctgacccgg tccgagggga tcatcccggc actggaatcc    1080
agccatgccg tggcctacgc cctcaagctg gcgccgactc tcagttccga caagatcgtc    1140
ctggtcaacc tgtctggccc tggcgacatg gatatccaca ccatcgccac ccgggagggc    1200
atcgttctgt ga                                                        1212
```

<210> SEQ ID NO 4
<211> LENGTH: 297
<212> TYPE: PRT
<213> ORGANISM: Artificial Sequence
<220> FEATURE:
<223> OTHER INFORMATION: mutant TrpB protein (R389P K392M mutant)

<400> SEQUENCE: 4

```
Met Ala Gly Phe Gln Cys Arg Asp Asp Pro Leu Gly Pro Gly Gln Asp
1               5                   10                  15

Met Glu Arg Leu Glu Arg Phe Gly Val Gly Thr Asp Ile Ala Arg
            20                  25                  30

Pro Ala Val Leu Glu Pro Gly Val Phe Arg Pro Asp Ala Arg Ile
        35                  40                  45

Val Gln Pro Gly Gly Asn Gly Met Gly Leu Asp Asp Leu Ala Val Phe
    50                  55                  60

Val Phe His Gln Val Gly Thr Val Ala Val Gln His Ala Gly Ala Ala
65                  70                  75                  80

Gly Ala Gln Arg Ser Arg Val Ala Thr Gly Phe Asp Thr Ile Pro Gly
                85                  90                  95

Gly Leu Asp Pro Val His Gly Asp Leu Ala Val Ile Asp Glu Arg Met
            100                 105                 110

Lys Gln Ala Asp Gly Ile Arg Ala Ala Ala His Ala Gly Asp Gln Gly
        115                 120                 125
```

```
Ile Gly Gln Thr Pro Arg His Leu Gln His Leu Pro Ala Arg Leu Ala
    130                 135                 140
Ala Asp His Gly Leu Glu Ile Ala His His Gly Ile Gly Met Gly
145                 150                 155                 160
Thr Arg His Arg Thr Asp Asp Val Glu Gly Ile Val Asp Val Gly His
                165                 170                 175
Pro Val Ala His Gly Phe Val Gln Arg Val Leu Glu Arg Pro Gly Thr
            180                 185                 190
Arg Val Asp Arg Tyr His Gly Gly Ala Glu Gln Leu His Ala Glu Tyr
        195                 200                 205
Val Glu Arg Leu Ala Leu Asp Val Asp Arg Pro His Val Asp His Ala
    210                 215                 220
Leu His Pro Gln Pro Gly Arg His Gly Gly Arg Gly His Ala Val Leu
225                 230                 235                 240
Ala Gly Thr Gly Leu Gly Asp His Pro Pro Leu Ala His Ala Leu Gly
                245                 250                 255
Gln Gln Cys Leu Ala Asp Gly Val Val Asp Leu Val Cys Thr Gly Met
            260                 265                 270
Ile Glu Ile Phe Ala Leu Glu Glu Asp Leu Cys Ala Ala Glu Leu Pro
        275                 280                 285
Ala Gln Ala Phe Gly Met Val Asp Arg
    290                 295

<210> SEQ ID NO 5
<211> LENGTH: 1371
<212> TYPE: DNA
<213> ORGANISM: Artificial Sequence
<220> FEATURE:
<223> OTHER INFORMATION: FMO gene (codon optimized) - Methylophaga
      aminisulfidivorans

<400> SEQUENCE: 5
atggcaaccc gtattgcaat tctcggagca ggaccttccg gcatggcgca actccgtgcc      60
tttcaatccg cccaagagaa gggtgccgag atccccgaac tcgtctgttt cgaaaagcaa     120
gccgactggg gcggacaatg gaattacacg tggcggacgg ggctcgacga aaatggagag     180
cccgtccact cctcgatgta ccgctatctc tggtcgaatg gacccaagga gtgtttggaa     240
tttgccgact acacgttcga cgagcacttc gggaagccca tcgcgtccta cccgccccgt     300
gaggtcttgt gggattatat caaggggcgt gtcgagaagg caggggtccg gaagtacatt     360
cggttcaata cggcagtccg gcacgtcgag ttcaatgagg actcgcaaac gttcacggtc     420
acggtccaag accacacgac ggacacgatc tattccgagg agttcgacta cgtcgtctgt     480
tgtacggggc acttctccac gccctacgtc cctgagttcg agggtttcga agagtttggc     540
gggcggattt gcacgcccca cgactttcgt gacgccttgg agttcaagga caagacggtc     600
ctcttggtcg gatcgtccta ctccgccgaa gatattggtt cgcaatgtta caagtacggt     660
gccaagaagt tgatctcgtg ttaccggacg gcccccatgg ggtacaaatg gcccgagaat     720
tgggacgagc gtcccaattt ggtccgggtc gatacggaga atgcatactt cgccgacggt     780
tcctcggaga aagtcgatgc aatcatcttg tgtacggggc atatccacca cttcccttc      840 ctcaatgacg atctccggct cgtcacgaat aatcggctct ggcctctcaa tttgtacaag     900
ggtgtcgtct gggaagacaa tcccaagttc ttctacattg aatgcaagac caatggtac      960 tccttcaata tgtttgacgc ccaagcctgg tacgcacgtg acgtcatcat ggggcgtctc    1020
```

```
cctctccctt ccaaggaaga gatgaaagcc gactcgatgg cctggcgtga aaaggagctg    1080
acgttggtca cggccgagga aatgtacacg taccaaggag attatatcca aaatctcatt    1140
gacatgacgg actacccctc gttcgacatc cccgccacga ataagacgtt cttggagtgg    1200
aagcatcaca agaaggagaa tattatgacg ttccgtgatc actcgtaccg gtcgttgatg    1260
acggggacga tggcccccaa gcaccacacg ccttggattg acgccttgga cgactccctg    1320
gaagcctact tgtccgacaa gtcggaaatc cccgtcgcca agaagcata g               1371
```

```
<210> SEQ ID NO 6
<211> LENGTH: 456
<212> TYPE: PRT
<213> ORGANISM: Artificial Sequence
<220> FEATURE:
<223> OTHER INFORMATION: FMO protein - Methylophaga aminisulfidivorans

<400> SEQUENCE: 6
```

Met Ala Thr Arg Ile Ala Ile Leu Gly Ala Gly Pro Ser Gly Met Ala
1               5                   10                  15

Gln Leu Arg Ala Phe Gln Ser Ala Gln Glu Lys Gly Ala Glu Ile Pro
                20                  25                  30

Glu Leu Val Cys Phe Glu Lys Gln Ala Asp Trp Gly Gly Gln Trp Asn
            35                  40                  45

Tyr Thr Trp Arg Thr Gly Leu Asp Glu Asn Gly Glu Pro Val His Ser
    50                  55                  60

Ser Met Tyr Arg Tyr Leu Trp Ser Asn Gly Pro Lys Glu Cys Leu Glu
65                  70                  75                  80

Phe Ala Asp Tyr Thr Phe Asp Glu His Phe Gly Lys Pro Ile Ala Ser
                85                  90                  95

Tyr Pro Pro Arg Glu Val Leu Trp Asp Tyr Ile Lys Gly Arg Val Glu
            100                 105                 110

Lys Ala Gly Val Arg Lys Tyr Ile Arg Phe Asn Thr Ala Val Arg His
        115                 120                 125

Val Glu Phe Asn Glu Asp Ser Gln Thr Phe Thr Val Thr Val Gln Asp
130                 135                 140

His Thr Asp Thr Ile Tyr Ser Glu Glu Phe Asp Tyr Val Val Cys
145                 150                 155                 160

Cys Thr Gly His Phe Ser Thr Pro Tyr Val Pro Glu Phe Glu Gly Phe
                165                 170                 175

Glu Lys Phe Gly Gly Arg Ile Leu His Ala His Asp Phe Arg Asp Ala
            180                 185                 190

Leu Glu Phe Lys Asp Lys Thr Val Leu Leu Val Gly Ser Ser Tyr Ser
        195                 200                 205

Ala Glu Asp Ile Gly Ser Gln Cys Tyr Lys Tyr Gly Ala Lys Lys Leu
    210                 215                 220

Ile Ser Cys Tyr Arg Thr Ala Pro Met Gly Tyr Lys Trp Pro Glu Asn
225                 230                 235                 240

Trp Asp Glu Arg Pro Asn Leu Val Arg Val Asp Thr Glu Asn Ala Tyr
                245                 250                 255

Phe Ala Asp Gly Ser Ser Glu Lys Val Asp Ala Ile Ile Leu Cys Thr
            260                 265                 270

Gly Tyr Ile His His Phe Pro Phe Leu Asn Asp Asp Leu Arg Leu Val
        275                 280                 285

Thr Asn Asn Arg Leu Trp Pro Leu Asn Leu Tyr Lys Gly Val Val Trp
    290                 295                 300

```
            Glu Asp Asn Pro Lys Phe Phe Tyr Ile Gly Met Gln Asp Gln Trp Tyr
            305                 310                 315                 320

Ser Phe Asn Met Phe Asp Ala Gln Ala Trp Tyr Ala Arg Asp Val Ile
                            325                 330                 335

Met Gly Arg Leu Pro Leu Pro Ser Lys Glu Glu Met Lys Ala Asp Ser
                        340                 345                 350

Met Ala Trp Arg Glu Lys Glu Leu Thr Leu Val Thr Ala Glu Glu Met
                    355                 360                 365

Tyr Thr Tyr Gln Gly Asp Tyr Ile Gln Asn Leu Ile Asp Met Thr Asp
                370                 375                 380

Tyr Pro Ser Phe Asp Ile Pro Ala Thr Asn Lys Thr Phe Leu Glu Trp
            385                 390                 395                 400

Lys His His Lys Lys Glu Asn Ile Met Thr Phe Arg Asp His Ser Tyr
                            405                 410                 415

Arg Ser Leu Met Thr Gly Thr Met Ala Pro Lys His His Thr Pro Trp
                        420                 425                 430

Ile Asp Ala Leu Asp Asp Ser Leu Glu Ala Tyr Leu Ser Asp Lys Ser
                    435                 440                 445

Glu Ile Pro Val Ala Lys Glu Ala
                450                 455

<210> SEQ ID NO 7
<211> LENGTH: 1167
<212> TYPE: DNA
<213> ORGANISM: Artificial Sequence
<220> FEATURE:
<223> OTHER INFORMATION: IacA gene (codon-optimized) - Acinetobacter
      baumannii

<400> SEQUENCE: 7
atgaacaagc tgtcgaagat ggagttcgcc tcgcaggaca aggccgtgga cctggacgcc      60
ctgtgccagg agatccggga gcgcgcctgc accggcgaat tgacaaccca ggcctacgtg     120
agccaggaca tcatcgagaa gctgaagcag atcgcgtgtc accggccct ggtcccgaag      180 cgcttcggcg gcgaagagtg gagcccgcgc cagttctgcg agctgatcga gaccctgtcg     240
aaggcggacg gcagcgtcgg ctgggtcgcc agcttcggca tgtcgccggc ctacctgggc     300
agcctgccgg aagagaccct gaaggagctg taccagaacg gccgacgt cgtcttcgcg       360 ggcggcatct tcccgccgca gccggccgag atcaccgacg aaggcgtcgt cgtccgcggc     420
cgctggaagt ctccagcgg ctgcatgggc gcggacatcg tcggcgtggg catctcgccg      480
ctgaagaaca cgaaatgca gggcctgccg cgcatggccg tgatgccggc caagaaggcc     540
aagatcgaga tgacctggga caccgtgggc ctgaagggca ccggctcgca cgacctggtc     600
gtcgaggacg tcctggtcga agaagtgg accttcgtgc gcggcgagcc gagcaagctg      660
tcggagccgt tcttcaagta cccgtcgctg tcgctggcca cccaggtcct gaccgtggtc     720
ggcatcggcg tcgcggccgc cgccctggag gagttcgaaa agctggcccc gggcaaggcc     780
agcatcaccg gcggcagcga aatcgccaac cgcccggtca cccagtacga atttgcccag     840
gccgacgccg agttccaggc cgccaagagc tggttctacc agaccatgga catcgtctgg     900
aacgaaatca tcgccggccg cgaggccacc gccgaacaga tcagcgacat cgcctggcc     960 tgcaccccacg ccgcccgcgt ctgcgccaag gtcacccgca agatgcagat gctggccggc    1020
atgaccgcca tctacaccaa caccccttc agccgcttcg tcaacgacac caacgtcgtc     1080
acccagcacg ccttcatggg cgacgccacc ctgcaaaacg ccggcctggt cagcttcggc    1140
```

```
ctgaagcccg ccccggcta cctgtga                                          1167
```

<210> SEQ ID NO 8
<211> LENGTH: 388
<212> TYPE: PRT
<213> ORGANISM: Artificial Sequence
<220> FEATURE:
<223> OTHER INFORMATION: IacA protein - Acinetobacter baumannii

<400> SEQUENCE: 8

```
Met Asn Lys Leu Ser Lys Met Glu Phe Ala Ser Gln Asp Lys Ala Val
1               5                   10                  15

Asp Leu Asp Ala Leu Cys Gln Glu Ile Arg Glu Arg Ala Cys Thr Gly
            20                  25                  30

Glu Phe Asp Asn Gln Ala Tyr Val Ser Gln Asp Ile Ile Glu Lys Leu
        35                  40                  45

Lys Gln Ile Gly Val Tyr Arg Ala Leu Val Pro Lys Arg Phe Gly Gly
    50                  55                  60

Glu Glu Trp Ser Pro Arg Gln Phe Cys Glu Leu Ile Glu Thr Leu Ser
65                  70                  75                  80

Lys Ala Asp Gly Ser Val Gly Trp Val Ala Ser Phe Gly Met Ser Pro
                85                  90                  95

Ala Tyr Leu Gly Ser Leu Pro Glu Glu Thr Leu Lys Glu Leu Tyr Gln
            100                 105                 110

Asn Gly Pro Asp Val Val Phe Ala Gly Gly Ile Phe Pro Gln Pro
        115                 120                 125

Ala Glu Ile Thr Asp Glu Gly Val Val Arg Gly Arg Trp Lys Phe
130                 135                 140

Ser Ser Gly Cys Met Gly Ala Asp Ile Val Gly Val Gly Ile Ser Pro
145                 150                 155                 160

Leu Lys Asn Asn Glu Met Gln Gly Leu Pro Arg Met Ala Val Met Pro
                165                 170                 175

Ala Lys Lys Ala Lys Ile Glu Met Thr Trp Asp Thr Val Gly Leu Lys
            180                 185                 190

Gly Thr Gly Ser His Asp Leu Val Val Glu Asp Val Leu Val Glu Lys
        195                 200                 205

Lys Trp Thr Phe Val Arg Gly Glu Pro Ser Lys Leu Ser Glu Pro Phe
    210                 215                 220

Phe Lys Tyr Pro Ser Leu Ser Leu Ala Thr Gln Val Leu Thr Val Val
225                 230                 235                 240

Gly Ile Gly Val Ala Ala Ala Leu Glu Glu Phe Glu Lys Leu Ala
                245                 250                 255

Pro Gly Lys Ala Ser Ile Thr Gly Gly Ser Glu Ile Ala Asn Arg Pro
            260                 265                 270

Val Thr Gln Tyr Glu Phe Ala Gln Ala Asp Ala Glu Phe Gln Ala Ala
        275                 280                 285

Lys Ser Trp Phe Tyr Gln Thr Met Asp Ile Val Trp Asn Glu Ile Ile
    290                 295                 300

Ala Gly Arg Glu Ala Thr Ala Glu Gln Ile Ser Asp Met Arg Leu Ala
305                 310                 315                 320

Cys Thr His Ala Ala Arg Val Cys Ala Lys Val Thr Arg Lys Met Gln
                325                 330                 335

Met Leu Ala Gly Met Thr Ala Ile Tyr Thr Asn Asn Pro Phe Ser Arg
            340                 345                 350

Phe Val Asn Asp Thr Asn Val Val Thr Gln His Ala Phe Met Gly Asp
```

```
                355                 360                 365
Ala Thr Leu Gln Asn Ala Gly Leu Val Ser Phe Gly Leu Lys Pro Ala
            370                 375                 380

Pro Gly Tyr Leu
385
```

<210> SEQ ID NO 9
<211> LENGTH: 1092
<212> TYPE: DNA
<213> ORGANISM: Methylococcus capsulatus

<400> SEQUENCE: 9

```
atgcccagcg tgtacaacac cgacgatctt cgcatctgcg agatcaagga agtcattccg      60
cccgtccagg ttcatgagga attcccgatc acggaccggg ccgcactcac gacactgacc     120
gcccgccgag ggattcacgc aatcctttcc aaggaggacg accgcctgct ggtggtgatc     180
gggccctgtt cgatccatga ccccaaggcg cgctcgaat acggggagcg gctgctgcca     240
ctccgccaga aactggcgag acatctggaa atcgtgatgc gggtctattt cgagaagccg     300
cgaacgaccg tcggctggaa gggcctgatc aatgatcccg atctggacga gagtttcaac     360
atcaacaaag gcttgcgcct cgcccgcaag ctgttgctcg atctgaacga actgggcatg     420
cccgcggcca ccgagtacct cgatctcatc accccgcagt atgtctccga cctgatcgct     480
tggggcgcca tcggtgctcg taccacggag agccagtctc accgtgaact ggcatcgggg     540
ctgtcatgtc cggttggatt caagaacgcc accgacggca cgatcaaggt tgctgtcgac     600
gccataggtg cggcacggcg ccacatcat ttcctgtctt tgaccaaggc cggtcattcg      660
gcgatcttct ccacgaccgg taacgccgac tgtcacatca tccttcgtgg cggagcccgg     720
ccgaattacg acgcggccag cgtcgaagcg gcggccaggg cgctggaagc cgtcggcctg     780
ccgcccaaca tcatggtgga ctgcagccat gccaacagca tgaaggatta cctgaagcag     840
ctgcggggtgg ccgaggacgt ggccgaacag atagacggcg cgacaggcg gatcatcggc     900
ttgatggtgg aaagtcacct caagccgggc aatcagaaac tccacaaggg catggttccc     960
gaataccggcg tcagcatcac cgatgcctgc atcggctggg atgacagcgt ggccgtgctg    1020
gaacggctcg ccgccgcggt ggagagccgg gcgcggccggt cggcaggcat ccggaacgtg   1080
cgggggggcct ga                                                       1092
```

<210> SEQ ID NO 10
<211> LENGTH: 363
<212> TYPE: PRT
<213> ORGANISM: Methylococcus capsulatus

<400> SEQUENCE: 10

```
Met Pro Ser Val Tyr Asn Thr Asp Asp Leu Arg Ile Cys Glu Ile Lys
1               5                  10                  15

Glu Val Ile Pro Pro Val Gln Val His Glu Glu Phe Pro Ile Thr Asp
            20                  25                  30

Arg Ala Ala Leu Thr Thr Leu Thr Ala Arg Arg Gly Ile His Ala Ile
        35                  40                  45

Leu Ser Lys Glu Asp Asp Arg Leu Leu Val Val Ile Gly Pro Cys Ser
    50                  55                  60

Ile His Asp Pro Lys Ala Ala Leu Glu Tyr Gly Glu Arg Leu Leu Pro
65                  70                  75                  80

Leu Arg Gln Lys Leu Ala Arg His Leu Glu Ile Val Met Arg Val Tyr
                85                  90                  95
```

Phe Glu Lys Pro Arg Thr Thr Val Gly Trp Lys Gly Leu Ile Asn Asp
            100                 105                 110

Pro Asp Leu Asp Glu Ser Phe Asn Ile Asn Lys Gly Leu Arg Leu Ala
            115                 120                 125

Arg Lys Leu Leu Leu Asp Leu Asn Glu Leu Gly Met Pro Ala Ala Thr
        130                 135                 140

Glu Tyr Leu Asp Leu Ile Thr Pro Gln Tyr Val Ser Asp Leu Ile Ala
145                 150                 155                 160

Trp Gly Ala Ile Gly Ala Arg Thr Thr Glu Ser Gln Ser His Arg Glu
                165                 170                 175

Leu Ala Ser Gly Leu Ser Cys Pro Val Gly Phe Lys Asn Ala Thr Asp
            180                 185                 190

Gly Thr Ile Lys Val Ala Val Asp Ala Ile Gly Ala Ala Arg Arg Pro
        195                 200                 205

His His Phe Leu Ser Leu Thr Lys Ala Gly His Ser Ala Ile Phe Ser
    210                 215                 220

Thr Thr Gly Asn Ala Asp Cys His Ile Ile Leu Arg Gly Gly Ala Arg
225                 230                 235                 240

Pro Asn Tyr Asp Ala Ala Ser Val Glu Ala Ala Arg Ala Leu Glu
                245                 250                 255

Ala Val Gly Leu Pro Pro Asn Ile Met Val Asp Cys Ser His Ala Asn
            260                 265                 270

Ser Met Lys Asp Tyr Leu Lys Gln Leu Arg Val Ala Glu Asp Val Ala
        275                 280                 285

Glu Gln Ile Asp Gly Gly Asp Arg Arg Ile Ile Gly Leu Met Val Glu
    290                 295                 300

Ser His Leu Lys Pro Gly Asn Gln Lys Leu His Lys Gly Met Val Pro
305                 310                 315                 320

Glu Tyr Gly Val Ser Ile Thr Asp Ala Cys Ile Gly Trp Asp Asp Ser
                325                 330                 335

Val Ala Val Leu Glu Arg Leu Ala Ala Ala Val Glu Ser Arg Arg Gly
            340                 345                 350

Arg Ser Ala Gly Ile Arg Asn Val Arg Gly Ala
        355                 360

<210> SEQ ID NO 11
<211> LENGTH: 1071
<212> TYPE: DNA
<213> ORGANISM: Escherichia coli

<400> SEQUENCE: 11
atgcaaaaag acgcgctgaa taacgtacat attaccgacg aacaggtttt aatgactccg      60
gaacaactga aggccgcttt ccattgagc ctgcaacaag aagcccagat tgctgactcg     120
cgtaaaagca tttcagatat tatcgccggg cgcgatcctc gtctgctggt agtatgtggt     180
ccttgttcca ttcatgatcc ggaaactgct ctggaatatg tcgtcgatt taaagccctt     240 gccgcagagg tcagcgatag cctctatctg gtaatgcgcg tctattttga aaaccccgt     300 accactgtcg gctggaaagg gttaattaac gatccccata tggatggctc ttttgatgta     360
gaagccgggc tgcagatcgc gcgtaaattg ctgcttgagc tggtgaatat gggactgcca     420
ctggcgacgg aagcgttaga tccgaatagc ccgcaatacc tgggcgatct gtttagctgg     480
tcagcaattg gtgctcgtac aacggaatcg caaactcacc gtgaaatggc ctccgggctt     540
tccatgccgg ttggttttaa aaacggcacc gacggcagtc tggcaacagc aattaacgct     600

```
atgcgcgccg ccgcccagcc gcaccgtttt gttggcatta accaggcagg gcaggttgcg    660
ttgctacaaa ctcagggaa tccggacggc catgtgatcc tgcgcggtgg taaagcgccg    720
aactatagcc ctgcggatgt tgcgcaatgt gaaaaagaga tggaacaggc gggactgcgc    780
ccgtctctga tggtagattg cagccacggt aattccaata aagattatcg ccgtcagcct    840
gcggtggcag aatccgtggt tgctcaaatc aaagatggca atcgctcaat tattggtctg    900
atgatcgaaa gtaatatcca cgagggcaat cagtcttccg agcaaccgcg cagtgaaatg    960
aaatacggtg tatccgtaac cgatgcctgc attagctggg aaatgaccga tgccttgctg   1020
cgtgaaattc atcaggatct gaacgggcag ctgacggctc gcgtggctta a            1071
```

<210> SEQ ID NO 12
<211> LENGTH: 356
<212> TYPE: PRT
<213> ORGANISM: Escherichia coli

<400> SEQUENCE: 12

```
Met Gln Lys Asp Ala Leu Asn Asn Val His Ile Thr Asp Glu Gln Val
1               5                   10                  15

Leu Met Thr Pro Glu Gln Leu Lys Ala Ala Phe Pro Leu Ser Leu Gln
            20                  25                  30

Gln Glu Ala Gln Ile Ala Asp Ser Arg Lys Ser Ile Ser Asp Ile Ile
        35                  40                  45

Ala Gly Arg Asp Pro Arg Leu Leu Val Val Cys Gly Pro Cys Ser Ile
    50                  55                  60

His Asp Pro Glu Thr Ala Leu Glu Tyr Ala Arg Arg Phe Lys Ala Leu
65                  70                  75                  80

Ala Ala Glu Val Ser Asp Ser Leu Tyr Leu Val Met Arg Val Tyr Phe
                85                  90                  95

Glu Lys Pro Arg Thr Thr Val Gly Trp Lys Gly Leu Ile Asn Asp Pro
            100                 105                 110

His Met Asp Gly Ser Phe Asp Val Glu Ala Gly Leu Gln Ile Ala Arg
        115                 120                 125

Lys Leu Leu Leu Glu Leu Val Asn Met Gly Leu Pro Leu Ala Thr Glu
    130                 135                 140

Ala Leu Asp Pro Asn Ser Pro Gln Tyr Leu Gly Asp Leu Phe Ser Trp
145                 150                 155                 160

Ser Ala Ile Gly Ala Arg Thr Thr Glu Ser Gln Thr His Arg Glu Met
                165                 170                 175

Ala Ser Gly Leu Ser Met Pro Val Gly Phe Lys Asn Gly Thr Asp Gly
            180                 185                 190

Ser Leu Ala Thr Ala Ile Asn Ala Met Arg Ala Ala Gln Pro His
        195                 200                 205

Arg Phe Val Gly Ile Asn Gln Ala Gly Gln Val Ala Leu Leu Gln Thr
    210                 215                 220

Gln Gly Asn Pro Asp Gly His Val Ile Leu Arg Gly Gly Lys Ala Pro
225                 230                 235                 240

Asn Tyr Ser Pro Ala Asp Val Ala Gln Cys Glu Lys Glu Met Glu Gln
                245                 250                 255

Ala Gly Leu Arg Pro Ser Leu Met Val Asp Cys Ser His Gly Asn Ser
            260                 265                 270

Asn Lys Asp Tyr Arg Arg Gln Pro Ala Val Ala Glu Ser Val Val Ala
        275                 280                 285
```

```
Gln Ile Lys Asp Gly Asn Arg Ser Ile Ile Gly Leu Met Ile Glu Ser
    290                 295                 300
Asn Ile His Glu Gly Asn Gln Ser Ser Glu Gln Pro Arg Ser Glu Met
305                 310                 315                 320
Lys Tyr Gly Val Ser Val Thr Asp Ala Cys Ile Ser Trp Glu Met Thr
                325                 330                 335
Asp Ala Leu Leu Arg Glu Ile His Gln Asp Leu Asn Gly Gln Leu Thr
            340                 345                 350
Ala Arg Val Ala
        355
```

```
<210> SEQ ID NO 13
<211> LENGTH: 1080
<212> TYPE: DNA
<213> ORGANISM: Methylococcus capsulatus

<400> SEQUENCE: 13
atgaaaacct tacacgtcga gctgggggag cgcggctacc ccatttatat aggacggggc      60
ctgctgggcc atcccgacct gatacaggcc catctgccgg cgggcaggt cctggtggtg     120
accaacgaag tggtggcgcc gctgtacctc gaccgcatgc ttgcatccct ggccggcaag    180
gacacgggca gtgtcgtgct ccccgacggc gaggcccaca gaccctgga ctcggcgatg     240
gccgtgttcg atgccttgct ggccggcgt ttcggccgca cgccgccat cgtgcgctc      300
ggcggcgggg tgatcggcga tctggccggt ttcgcggcag cctgctatca gcgcggcgtg    360
cctttcatcc aggtgcccac cacccctgttg tctcaggtcg actcctcggt gggaggcaag    420
accgcggtca ccatccgcg cggcaagaac atgatcggcg ccttctacca gccgcgctgc     480
gttctggccg acaccgacac tctggatacg ttgcccgacc gcgaactgag cgcgggtctg    540
gccgaggtca tcaagtacgg cttcatccgt gacccggaat tcctggcctg gctcgaagcg    600
aacgtcgagc gcttgctgca gcgcgatccc gaagcgctcg cctatgccat cgagcggtcc    660
tgcatcaaca aggcggaaat cgtggcggaa gacgagaccg aaaccggggt gcgggcgacg    720
ctgaacctgg ggcacacttt cggccacgcc atcgaaaccg gcatgggcta tggtgtatgt    780
ctgcacggcg aagcggtggc gatcggtatg tgccaggcgg ccgatctgtc ccgtcgcttg    840
ggctggatcg gtgacgacga ggtggcgagg gtgatccgcc tgctggagcg gcgcggctg     900
ccggtcgtcc cgccgcgcga gttggatgcg acgccttc tcgaacacat ggcggtcgac      960
aagaagaacg tcgacggcgg tctgcgactg gttctgctca aatccctggg tgaggcgacc   1020
ctgccggtgg ccgtgacgc cggactgtta cgggccacat ggaatgcta cggccgctga   1080

<210> SEQ ID NO 14
<211> LENGTH: 359
<212> TYPE: PRT
<213> ORGANISM: Methylococcus capsulatus

<400> SEQUENCE: 14

Met Lys Thr Leu His Val Glu Leu Gly Glu Arg Gly Tyr Pro Ile Tyr
1               5                   10                  15
Ile Gly Arg Gly Leu Leu Gly His Pro Asp Leu Ile Gln Ala His Leu
            20                  25                  30
Pro Gly Gly Gln Val Leu Val Val Thr Asn Glu Val Val Ala Pro Leu
        35                  40                  45
Tyr Leu Asp Arg Met Leu Ala Ser Leu Ala Gly Lys Asp Thr Gly Ser
    50                  55                  60
```

```
Val Val Leu Pro Asp Gly Glu Ala His Lys Thr Leu Asp Ser Ala Met
 65                  70                  75                  80

Ala Val Phe Asp Ala Leu Leu Ala Arg Arg Phe Gly Arg Asn Ala Ala
                 85                  90                  95

Ile Val Ala Leu Gly Gly Val Ile Gly Asp Leu Ala Gly Phe Ala
            100                 105                 110

Ala Ala Cys Tyr Gln Arg Gly Val Pro Phe Ile Gln Val Pro Thr Thr
            115                 120                 125

Leu Leu Ser Gln Val Asp Ser Ser Val Gly Gly Lys Thr Ala Val Asn
        130                 135                 140

His Pro Arg Gly Lys Asn Met Ile Gly Ala Phe Tyr Gln Pro Arg Cys
145                 150                 155                 160

Val Leu Ala Asp Thr Asp Thr Leu Asp Thr Leu Pro Asp Arg Glu Leu
                165                 170                 175

Ser Ala Gly Leu Ala Glu Val Ile Lys Tyr Gly Phe Ile Arg Asp Pro
            180                 185                 190

Glu Phe Leu Ala Trp Leu Glu Ala Asn Val Gly Arg Leu Leu Gln Arg
        195                 200                 205

Asp Pro Glu Ala Leu Ala Tyr Ala Ile Glu Arg Ser Cys Ile Asn Lys
210                 215                 220

Ala Glu Ile Val Ala Glu Asp Glu Thr Glu Thr Gly Val Arg Ala Thr
225                 230                 235                 240

Leu Asn Leu Gly His Thr Phe Gly His Ala Ile Glu Thr Gly Met Gly
                245                 250                 255

Tyr Gly Val Cys Leu His Gly Glu Ala Val Ala Ile Gly Met Cys Gln
            260                 265                 270

Ala Ala Asp Leu Ser Arg Arg Leu Gly Trp Ile Gly Asp Asp Glu Val
            275                 280                 285

Ala Arg Val Ile Arg Leu Leu Glu Arg Ala Arg Leu Pro Val Val Pro
        290                 295                 300

Pro Arg Glu Leu Asp Ala Asp Ala Phe Leu His Met Ala Val Asp
305                 310                 315                 320

Lys Lys Asn Val Asp Gly Gly Leu Arg Leu Val Leu Leu Lys Ser Leu
                325                 330                 335

Gly Glu Ala Thr Leu Pro Val Ala Val Asp Ala Gly Leu Leu Arg Ala
            340                 345                 350

Thr Leu Glu Cys Tyr Gly Arg
        355

<210> SEQ ID NO 15
<211> LENGTH: 447
<212> TYPE: DNA
<213> ORGANISM: Methylococcus capsulatus

<400> SEQUENCE: 15
atggcgggta tcttggtgct gaacgggcct aacctcaatc tgttgggggt acgtgagccg    60
ggtatctatg gcagcgacac gctttcggat atcgaatcgc gtctgcaggc acaggccagg   120
gtggcaggca tgccgatcga tttcttccag agcaatgccg agcatgctct gatcgaacgc   180 attaccagg cgttccgcga tgcggtcgac atgatcatca tcaatcccgg cgccctcacc   240
cataccagcg tcgctttgcg cgatgcgttg ctggccaccg ccgtgccttt cattgaagta   300
cacatttcga acgttcatgc gcgcgagccg ttccgccgcc attcctatct ttccgatatt   360 gccaggggg tcatctgcgg attgggcccc atgggctacg aactggcgct ccaggccgcc   420
```

```
ctgcaaatga cacataggtc gttatag                                         447
```

```
<210> SEQ ID NO 16
<211> LENGTH: 148
<212> TYPE: PRT
<213> ORGANISM: Methylococcus capsulatus

<400> SEQUENCE: 16
```

```
Met Ala Gly Ile Leu Val Leu Asn Gly Pro Asn Leu Asn Leu Leu Gly
1               5                   10                  15

Val Arg Glu Pro Gly Ile Tyr Gly Ser Asp Thr Leu Ser Asp Ile Glu
            20                  25                  30

Ser Arg Leu Gln Ala Gln Ala Arg Val Ala Gly Met Pro Ile Asp Phe
        35                  40                  45

Phe Gln Ser Asn Ala Glu His Ala Leu Ile Glu Arg Ile His Gln Ala
    50                  55                  60

Phe Arg Asp Ala Val Asp Met Ile Ile Ile Asn Pro Gly Ala Leu Thr
65                  70                  75                  80

His Thr Ser Val Ala Leu Arg Asp Ala Leu Leu Ala Thr Ala Val Pro
                85                  90                  95

Phe Ile Glu Val His Ile Ser Asn Val His Ala Arg Glu Pro Phe Arg
            100                 105                 110

Arg His Ser Tyr Leu Ser Asp Ile Ala Arg Gly Val Ile Cys Gly Leu
        115                 120                 125

Gly Pro Met Gly Tyr Glu Leu Ala Leu Gln Ala Ala Leu Gln Met Thr
    130                 135                 140

His Arg Ser Leu
145
```

```
<210> SEQ ID NO 17
<211> LENGTH: 840
<212> TYPE: DNA
<213> ORGANISM: Methylococcus capsulatus

<400> SEQUENCE: 17
atgacccagc ccgaccgata cgccgtgttc gggcacccga tcgaacacag ccagtcaccc    60
cgcatccatg ccctgttcgc cgcccagacc ggccaggacc tgatctacac cgccgaggac   120
gtgccaccog accggttcga atcctgcgtc cgcgcgttct tcgacggcgg tggccgcggc   180
ctcaactgca cgatcccgct caaggagatg gcctggctgc tcgcggacag ccgcagcggc   240
agggcaaagc gggcgcgtgc ggtcaacacg ctgctcctgc gggccgatgg ctcgatcttc   300
ggcgacaaca ccgatggcat cggtctgctc cgcgacctgc gggacaacct cggactgaac   360
ctcgcgggca cgaaaatcct catactcggc gccggcgggg cgacgcgggg aatcctggcg   420
cccctgctgg ccgagcggcc ggaccggctg gtcatcgcca accgcaccgt cgccacggcg   480
gaaaccctga ccgtggaatt cggcgacctg ggccccgtcg aaggctgcgg cttcgctgca   540
ttggccggtc gccgcttcga cctgatcatc aacgccaccg ccgccagtct gagcggcgaa   600
ctcccgccgc tccccgccga catactcgcc cccggcggca gttgctacga cctggcctat   660
gccgccgaac cgacgccctt cgtgcggtgg ggccaggaaa agcaagcggt cgtcagtgcc   720
gacggcatcg gcatgctggt ggaacaggcc gccgaagcct tcctgctctg cgcgcggtgtg   780
cgcccgcaaa cacgcccggt gatcgagacg ctcgaagccg agcgacgaac cgcgaagtga   840
```

```
<210> SEQ ID NO 18
<211> LENGTH: 279
```

```
<212> TYPE: PRT
<213> ORGANISM: Methylococcus capsulatus

<400> SEQUENCE: 18

Met Thr Gln Pro Asp Arg Tyr Ala Val Phe Gly His Pro Ile Glu His
1               5                   10                  15

Ser Gln Ser Pro Arg Ile His Ala Leu Phe Ala Ala Gln Thr Gly Gln
            20                  25                  30

Asp Leu Ile Tyr Thr Ala Glu Asp Val Pro Pro Asp Arg Phe Glu Ser
        35                  40                  45

Cys Val Arg Ala Phe Phe Asp Gly Gly Arg Gly Leu Asn Cys Thr
    50                  55                  60

Ile Pro Leu Lys Glu Met Ala Trp Leu Leu Ala Asp Ser Arg Ser Gly
65                  70                  75                  80

Arg Ala Lys Arg Ala Arg Ala Val Asn Thr Leu Leu Arg Ala Asp
                85                  90                  95

Gly Ser Ile Phe Gly Asp Asn Thr Asp Gly Ile Gly Leu Leu Arg Asp
            100                 105                 110

Leu Arg Asp Asn Leu Gly Leu Asn Leu Ala Gly Thr Lys Ile Leu Ile
        115                 120                 125

Leu Gly Ala Gly Gly Ala Thr Arg Gly Ile Leu Ala Pro Leu Leu Ala
    130                 135                 140

Glu Arg Pro Asp Arg Leu Val Ile Ala Asn Arg Thr Val Ala Thr Ala
145                 150                 155                 160

Glu Thr Leu Thr Val Glu Phe Gly Asp Leu Gly Pro Val Glu Gly Cys
                165                 170                 175

Gly Phe Ala Ala Leu Ala Gly Arg Arg Phe Asp Leu Ile Ile Asn Ala
            180                 185                 190

Thr Ala Ala Ser Leu Ser Gly Glu Leu Pro Pro Leu Pro Ala Asp Ile
        195                 200                 205

Leu Ala Pro Gly Gly Ser Cys Tyr Asp Leu Ala Tyr Ala Ala Glu Pro
    210                 215                 220

Thr Pro Phe Val Arg Trp Gly Gln Glu Lys Gln Ala Val Val Ser Ala
225                 230                 235                 240

Asp Gly Ile Gly Met Leu Val Glu Gln Ala Ala Glu Ala Phe Leu Leu
                245                 250                 255

Trp Arg Gly Val Arg Pro Gln Thr Arg Pro Val Ile Glu Thr Leu Glu
            260                 265                 270

Ala Glu Arg Arg Thr Ala Lys
        275

<210> SEQ ID NO 19
<211> LENGTH: 540
<212> TYPE: DNA
<213> ORGANISM: Methylococcus capsulatus

<400> SEQUENCE: 19
atgcgaaacc gtcgaaacat cttcctgatc ggcccgatgg agcgggcaa gaccaccgtg      60 ggacgtctgc tcgcccgtgc cctggggatg gagttctggg acagcgacaa ggaaatcgaa    120
cgccggaccg cgtcacggt gccgatgatt ttcgaatacg agggcgaggc cggattccgg    180
cgccgcgaat cggaagtcat cgccgatctc acgggcaagg aaaggatcgt gctggccacc    240
ggcggcggtt cggtgctggc agcggagaac cgggagcatc tggcggcacg ggggctggta    300
atttacctgc agtgttcggt ccagaagcag ttggagagga cgcacaagga catgaaccgg    360
```

```
cccttgttgc agacggagaa tcccaggcaa aggctggaag aactgctgcg ggtgagggat      420
cccatctacc gcgagcttgc cgactacgtc gtcgataccg ccagcattc gagccgcagt       480 gccgtgcgcc ggatcatcaa cgcctacgag aaatccggaa ccagactgcg gacggaatga     540
```

<210> SEQ ID NO 20
<211> LENGTH: 179
<212> TYPE: PRT
<213> ORGANISM: Methylococcus capsulatus

<400> SEQUENCE: 20

```
Met Arg Asn Arg Arg Asn Ile Phe Leu Ile Gly Pro Met Gly Ala Gly
1               5                   10                  15

Lys Thr Thr Val Gly Arg Leu Leu Ala Arg Ala Leu Gly Met Glu Phe
            20                  25                  30

Trp Asp Ser Asp Lys Glu Ile Glu Arg Arg Thr Gly Val Thr Val Pro
        35                  40                  45

Met Ile Phe Glu Tyr Glu Gly Glu Ala Gly Phe Arg Arg Arg Glu Ser
    50                  55                  60

Glu Val Ile Ala Asp Leu Thr Gly Lys Glu Arg Ile Val Leu Ala Thr
65                  70                  75                  80

Gly Gly Gly Ser Val Leu Ala Ala Glu Asn Arg Glu His Leu Ala Ala
                85                  90                  95

Arg Gly Leu Val Ile Tyr Leu Gln Cys Ser Val Gln Lys Gln Leu Glu
            100                 105                 110

Arg Thr His Lys Asp Met Asn Arg Pro Leu Leu Gln Thr Glu Asn Pro
        115                 120                 125

Arg Gln Arg Leu Glu Glu Leu Leu Arg Val Arg Asp Pro Ile Tyr Arg
    130                 135                 140

Glu Leu Ala Asp Tyr Val Val Asp Thr Gly Gln His Ser Ser Arg Ser
145                 150                 155                 160

Ala Val Arg Arg Ile Ile Asn Ala Tyr Glu Lys Ser Gly Thr Arg Leu
                165                 170                 175

Arg Thr Glu
```

<210> SEQ ID NO 21
<211> LENGTH: 1269
<212> TYPE: DNA
<213> ORGANISM: Methylococcus capsulatus

<400> SEQUENCE: 21

```
atgcagggcg acatccgggt accgggcgac aagtccatct cccaccggtc ggtgatgctg       60
ggctcgctcg ccgagggcgt gactgaggtg agtggcttcc tccaggctga ggactgtttg      120
gcgaccatgg cggcgttccg ggccatgggc gtcgaaatcg aaggcccgac ggagggccgg      180
ctgcggatcc acggcgtcgg cctgcacggc ctgaagccac tgccgccccc cctggatctc      240
ggcaattccg gcacctccat gcggctattg agcggactgt ggcgggaca ggcattcgac       300 accacgctga ccggcgatgc ctccctggtg cgccggccga tgcggcgggt gaccgaaccg      360
ctgcgcgcca tgggcgcgcg gatcgacacc accgaagccg gcaccgcgcc actgcgcatc      420
gccggcggaa gccgctcaa agggatcgac tatgcgatgc cggtcgccag cgcccaggtg      480
aaatcctgtc tgctgctggc gggcctctac gcggaaggga gacctgtgt caccgagccg       540 gcgccgaccc gcgaccacac cgaacgcatg ctggcgggtt cggctatcc ggtggcgcga       600 gatggcaacc gtgtatgcat ccaatccggc ggcaagcttt ccgcgacccg tatcgacgta      660
```

| | | |
|---|---|---|
| ccggcggaca tttcctcggc ggcgttcttc atgataggcg cagcgatcag ccctgggtcc | 720 | |
| gacgtgttcc tccgccatgt cgggatcaat ccgacccgga ccggcgtcat cgaaatcctg | 780 | |
| cgcgaaatgg gcgccgacat cgagatactc gctccgcgcg aagtcggcgg tgaaccggtg | 840 | |
| gcggacctcc gcatccgtta ccgggaactg cgcggcatcc gcattcccga acataccgtg | 900 | |
| ccgctggcca ttgacgaatt cccggccctg ttcatcgccg cagcctgcgc cacaggcgaa | 960 | |
| acggtgctga ccggggccga ggagctgcga gtcaaggaaa cgaccgtat ccaggccatg | 1020 | |
| gccgacggcc tgaccacgct gggcatcgat gcccgcccga ccccgatgg catggtcatc | 1080 | |
| cggggcggga gtttccgcgg cggcgcagtc gattcgcgcg gcgatcatcg catcgccatg | 1140 | |
| tcattctcga tcgcggcatt gcgcgctccc atccccatcg agattcacga ctgcgccaac | 1200 | |
| gtggcgacat cttttcccaa tttcgtcgaa ctggcgcgga ccctgggttt ggacatcgag | 1260 | |
| gtcagctga | 1269 | |

<210> SEQ ID NO 22
<211> LENGTH: 422
<212> TYPE: PRT
<213> ORGANISM: Methylococcus capsulatus

<400> SEQUENCE: 22

```
Met Gln Gly Asp Ile Arg Val Pro Gly Asp Lys Ser Ile Ser His Arg
1               5                   10                  15

Ser Val Met Leu Gly Ser Leu Ala Glu Gly Val Thr Glu Val Ser Gly
            20                  25                  30

Phe Leu Gln Ala Glu Asp Cys Leu Ala Thr Met Ala Ala Phe Arg Ala
        35                  40                  45

Met Gly Val Glu Ile Glu Gly Pro Thr Glu Gly Arg Leu Arg Ile His
    50                  55                  60

Gly Val Gly Leu His Gly Leu Lys Pro Ala Ala Pro Leu Asp Leu
65                  70                  75                  80

Gly Asn Ser Gly Thr Ser Met Arg Leu Leu Ser Gly Leu Leu Ala Gly
                85                  90                  95

Gln Ala Phe Asp Thr Thr Leu Thr Gly Asp Ala Ser Leu Val Arg Arg
            100                 105                 110

Pro Met Arg Arg Val Thr Glu Pro Leu Arg Ala Met Gly Ala Arg Ile
        115                 120                 125

Asp Thr Thr Glu Ala Gly Thr Ala Pro Leu Arg Ile Ala Gly Gly Ser
    130                 135                 140

Arg Leu Lys Gly Ile Asp Tyr Ala Met Pro Val Ala Ser Ala Gln Val
145                 150                 155                 160

Lys Ser Cys Leu Leu Leu Ala Gly Leu Tyr Ala Glu Gly Lys Thr Cys
                165                 170                 175

Val Thr Glu Pro Ala Pro Thr Arg Asp His Thr Glu Arg Met Leu Ala
            180                 185                 190

Gly Phe Gly Tyr Pro Val Ala Arg Asp Gly Asn Arg Val Cys Ile Gln
        195                 200                 205

Ser Gly Gly Lys Leu Ser Ala Thr Arg Ile Asp Val Pro Ala Asp Ile
    210                 215                 220

Ser Ser Ala Ala Phe Phe Met Ile Gly Ala Ile Ser Pro Gly Ser
225                 230                 235                 240

Asp Val Phe Leu Arg His Val Gly Ile Asn Pro Thr Arg Thr Gly Val
                245                 250                 255

Ile Glu Ile Leu Arg Glu Met Gly Ala Asp Ile Glu Ile Leu Ala Pro
```

```
                260             265             270
Arg Glu Val Gly Gly Glu Pro Val Ala Asp Leu Arg Ile Arg Tyr Arg
        275                 280                 285

Glu Leu Arg Gly Ile Arg Ile Pro Glu His Thr Val Pro Leu Ala Ile
        290                 295                 300

Asp Glu Phe Pro Ala Leu Phe Ile Ala Ala Ala Cys Ala Thr Gly Glu
305                 310                 315                 320

Thr Val Leu Thr Gly Ala Glu Glu Leu Arg Val Lys Glu Ser Asp Arg
                325                 330                 335

Ile Gln Ala Met Ala Asp Gly Leu Thr Thr Leu Gly Ile Asp Ala Arg
                340                 345                 350

Pro Thr Pro Asp Gly Met Val Ile Arg Gly Gly Ser Phe Arg Gly Gly
                355                 360                 365

Ala Val Asp Ser Arg Gly Asp His Arg Ile Ala Met Ser Phe Ser Ile
                370                 375                 380

Ala Ala Leu Arg Ala Pro Ile Pro Ile Glu Ile His Asp Cys Ala Asn
385                 390                 395                 400

Val Ala Thr Ser Phe Pro Asn Phe Val Glu Leu Ala Arg Thr Leu Gly
                405                 410                 415

Leu Asp Ile Glu Val Ser
                420

<210> SEQ ID NO 23
<211> LENGTH: 1101
<212> TYPE: DNA
<213> ORGANISM: Methylococcus capsulatus

<400> SEQUENCE: 23
atgtccggaa acaccatcgg caaactgttt accgtcacga ccttcggcga aagccacggg      60
cctgcgctcg gctgcatcgt cgacggctgc cgccgggac ttgcgttgtc cgaggccgat     120
ctgcagcacg atctgtatcg ccgccggccg ggccagtccc gccacaccac ccagcggcgt     180
gagtcggaca ccgtcaagat cctgtccggg gtgttcgagg actcaccac cgggacgccg     240 atcggtctcc tgatcgagaa cgaggaccag cggtccaagg attacgccag catcgccgac     300
cgcttccgcc ccggccatgc cgactacacc taccacatga aatacggctt ccgcgactac     360
cgtggcggcg tcgctcgtc ggcgcgtgaa accgcgatgc gggtggcggc gggaggcatc     420
gccaagaaat acctgcgtga gcggttgggt gtcgaaatcc gcggctacct ggcccagctc     480
gggccgatcc ggatcgaccc ggtggactgg aacgccatcg acgacaaccc cttcttctgt     540
cccgatcccg ccagggttcc cgagcttgaa gcttacatgg atgccctgcg caaggaaggt     600
gattcgagcg gcgcccgggt caacgtggtg gccaggggcg tgccgccggg cttgggcgag     660
ccggtcttcg accggctcga cgccgagctg gcgtatgcgc tgatgagcat caacgccgtc     720
aagggtgtgg aaatcggcgc cggtttcggc tgtgtcgaag ccaagggttc ggtgttccgc     780
gatgagatga gtccggaagg tttcctgggg aattcggcgg cgtattct gggcgggata     840 tccaccggcc aggacatcgt tgccagcatc gcgctgaagc ctacctccag tctgcgtctc     900
ccgggccggt cggtgaacat ccgcggggaa tcggtgaag tcgtgaccac cggacgccat     960
gatccctgtg tcggcatccg ggccacgccg atcgccgagg cgatgatggc catcgtgctg    1020
atggatcatt atctgcgcca ccggggtcag aaccaggacg tcgtgcgcac gctcgatccc    1080
atcccgccca gcgcgttcta g                                              1101
```

```
<210> SEQ ID NO 24
<211> LENGTH: 366
<212> TYPE: PRT
<213> ORGANISM: Methylococcus capsulatus

<400> SEQUENCE: 24

Met Ser Gly Asn Thr Ile Gly Lys Leu Phe Thr Val Thr Thr Phe Gly
1               5                   10                  15

Glu Ser His Gly Pro Ala Leu Gly Cys Ile Val Asp Gly Cys Pro Pro
            20                  25                  30

Gly Leu Ala Leu Ser Glu Ala Asp Leu Gln His Asp Leu Tyr Arg Arg
        35                  40                  45

Arg Pro Gly Gln Ser Arg His Thr Thr Gln Arg Arg Glu Ser Asp Thr
50                  55                  60

Val Lys Ile Leu Ser Gly Val Phe Glu Gly Leu Thr Thr Gly Thr Pro
65                  70                  75                  80

Ile Gly Leu Leu Ile Glu Asn Glu Asp Gln Arg Ser Lys Asp Tyr Ala
                85                  90                  95

Ser Ile Ala Asp Arg Phe Arg Pro Gly His Ala Asp Tyr Thr Tyr His
            100                 105                 110

Met Lys Tyr Gly Phe Arg Asp Tyr Arg Gly Gly Arg Ser Ser Ala
        115                 120                 125

Arg Glu Thr Ala Met Arg Val Ala Ala Gly Ile Ala Lys Lys Tyr
130                 135                 140

Leu Arg Glu Arg Leu Gly Val Glu Ile Arg Gly Tyr Leu Ala Gln Leu
145                 150                 155                 160

Gly Pro Ile Arg Ile Asp Pro Val Asp Trp Asn Ala Ile Asp Asp Asn
                165                 170                 175

Pro Phe Phe Cys Pro Asp Pro Ala Arg Val Pro Glu Leu Glu Ala Tyr
            180                 185                 190

Met Asp Ala Leu Arg Lys Glu Gly Asp Ser Ser Gly Ala Arg Val Asn
        195                 200                 205

Val Val Ala Arg Gly Val Pro Pro Gly Leu Gly Glu Pro Val Phe Asp
210                 215                 220

Arg Leu Asp Ala Glu Leu Ala Tyr Ala Leu Met Ser Ile Asn Ala Val
225                 230                 235                 240

Lys Gly Val Glu Ile Gly Ala Gly Phe Gly Cys Val Glu Ala Lys Gly
                245                 250                 255

Ser Val Phe Arg Asp Glu Met Ser Pro Glu Gly Phe Leu Gly Asn Ser
            260                 265                 270

Ala Gly Gly Ile Leu Gly Gly Ile Ser Thr Gly Gln Asp Ile Val Ala
        275                 280                 285

Ser Ile Ala Leu Lys Pro Thr Ser Ser Leu Arg Leu Pro Gly Arg Ser
290                 295                 300

Val Asn Ile Arg Gly Glu Ser Val Glu Val Thr Thr Gly Arg His
305                 310                 315                 320

Asp Pro Cys Val Gly Ile Arg Ala Thr Pro Ile Ala Glu Ala Met Met
                325                 330                 335

Ala Ile Val Leu Met Asp His Tyr Leu Arg His Arg Gly Gln Asn Gln
            340                 345                 350

Asp Val Val Arg Thr Leu Asp Pro Ile Pro Pro Ser Ala Phe
        355                 360                 365

<210> SEQ ID NO 25
<211> LENGTH: 1212
```

<212> TYPE: DNA
<213> ORGANISM: Methylococcus capsulatus

<400> SEQUENCE: 25

```
atgcaagacg agattcagcc ctatgacctg cccgatgagc tcggccactt tggaccttac    60
ggtggcattt tcgtcgccga gaccttgatg gagccgctgg aagagctgaa agccgcctac   120
catcgctacc tgaaggaccc ggaattcctc gccgagctgg atcacgatct gaaccactac   180
gtcggccgcc cctcaccgat ctaccatgcc gaacgcctga gccgggagct cggcggcgca   240
cagatcttct tcaagcgcga agatctcaat cataccggtg cacacaaggt caacaacacc   300
gtcggccagg cactgctggc caagcgcatg ggcaagcggc gggtgatcgc cgagaccggt   360
gccggccagc acggcgtggc cacggccacc gtggcggccc ggctggggat ggagtgcgtg   420
gtctacatgg gggcggtcga cgtccagcgc caggcgctca acgtattccg catgaagctg   480
ctcggcgcca ccgtgatagc ggtcgactcg ggttcccgga cgctcaagga cgcgctgaac   540
gaagccatgc gcgactgggt gaccaacgtc gacgatacct tctacatcat cggtacggtg   600
gcgggtcccc atccctatcc cgccatggtg cgcgatttcc aggccgtgat cggccgcgag   660
gcgcgccggc agatgctgga gatgacgggg cgtctgcccg atgccctggt cgcctgcgtg   720
ggcggcggct cgaatgccat cggcctgttt catccgttcg tcgatgaccg cgaggtcgcc   780
atgtacgggg tcgaggccgc cggggatggt atcgaaaccg gtcgccactc ggctccgctg   840
agcgccggcc gccccggcgt gctgcacggc aaccgtacct acctgatgga agacgaagac   900
ggcgagatca tcgagaccca ttccatttcc gccgggctgg actatccggg cgtcgggccg   960
gaacacgcct ggctcaagga ctgcggccgg gcgagctatg tcagtgccac cgacgccgaa  1020
gcgctcgagg cgttccatat cctgacccgg tccgagggga tcatcccggc actggaatcc  1080
agccatgccg tggcctacgc cctcaagctg gcgccgactc tcagttccga caagatcgtc  1140
ctggtcaacc tgtctggccg tggcgacaag gatatccaca ccatcgccac ccgggagggc  1200
atcgttctgt ga                                                      1212
```

<210> SEQ ID NO 26
<211> LENGTH: 403
<212> TYPE: PRT
<213> ORGANISM: Methylococcus capsulatus

<400> SEQUENCE: 26

```
Met Gln Asp Glu Ile Gln Pro Tyr Asp Leu Pro Asp Glu Leu Gly His
1               5                   10                  15

Phe Gly Pro Tyr Gly Gly Ile Phe Val Ala Glu Thr Leu Met Glu Pro
            20                  25                  30

Leu Glu Glu Leu Lys Ala Ala Tyr His Arg Tyr Leu Lys Asp Pro Glu
        35                  40                  45

Phe Leu Ala Glu Leu Asp His Asp Leu Asn His Tyr Val Gly Arg Pro
    50                  55                  60

Ser Pro Ile Tyr His Ala Glu Arg Leu Ser Arg Glu Leu Gly Gly Ala
65                  70                  75                  80

Gln Ile Phe Phe Lys Arg Glu Asp Leu Asn His Thr Gly Ala His Lys
                85                  90                  95

Val Asn Asn Thr Val Gly Gln Ala Leu Leu Ala Lys Arg Met Gly Lys
            100                 105                 110

Arg Arg Val Ile Ala Glu Thr Gly Ala Gly Gln His Gly Val Ala Thr
        115                 120                 125
```

```
Ala Thr Val Ala Ala Arg Leu Gly Met Glu Cys Val Val Tyr Met Gly
            130                 135                 140

Ala Val Asp Val Gln Arg Gln Ala Leu Asn Val Phe Arg Met Lys Leu
145                 150                 155                 160

Leu Gly Ala Thr Val Ile Ala Val Asp Ser Gly Ser Arg Thr Leu Lys
                165                 170                 175

Asp Ala Leu Asn Glu Ala Met Arg Asp Trp Val Thr Asn Val Asp Asp
            180                 185                 190

Thr Phe Tyr Ile Ile Gly Thr Val Ala Gly Pro His Pro Tyr Pro Ala
        195                 200                 205

Met Val Arg Asp Phe Gln Ala Val Ile Gly Arg Glu Ala Arg Arg Gln
210                 215                 220

Met Leu Glu Met Thr Gly Arg Leu Pro Asp Ala Leu Val Ala Cys Val
225                 230                 235                 240

Gly Gly Gly Ser Asn Ala Ile Gly Leu Phe His Pro Phe Val Asp Asp
                245                 250                 255

Arg Glu Val Ala Met Tyr Gly Val Glu Ala Ala Gly Asp Gly Ile Glu
            260                 265                 270

Thr Gly Arg His Ser Ala Pro Leu Ser Ala Gly Arg Pro Gly Val Leu
        275                 280                 285

His Gly Asn Arg Thr Tyr Leu Met Glu Asp Glu Asp Gly Glu Ile Ile
    290                 295                 300

Glu Thr His Ser Ile Ser Ala Gly Leu Asp Tyr Pro Gly Val Gly Pro
305                 310                 315                 320

Glu His Ala Trp Leu Lys Asp Cys Gly Arg Ala Ser Tyr Val Ser Ala
                325                 330                 335

Thr Asp Ala Glu Ala Leu Glu Ala Phe His Ile Leu Thr Arg Ser Glu
            340                 345                 350

Gly Ile Ile Pro Ala Leu Glu Ser Ser His Ala Val Ala Tyr Ala Leu
        355                 360                 365

Lys Leu Ala Pro Thr Leu Ser Ser Asp Lys Ile Val Leu Val Asn Leu
370                 375                 380

Ser Gly Arg Gly Asp Lys Asp Ile His Thr Ile Ala Thr Arg Glu Gly
385                 390                 395                 400

Ile Val Leu

<210> SEQ ID NO 27
<211> LENGTH: 6109
<212> TYPE: DNA
<213> ORGANISM: Artificial Sequence
<220> FEATURE:
<223> OTHER INFORMATION: Vector backbone (derived from vector pMHA201)

<400> SEQUENCE: 27
taattgcgtt gcgctcactg cccgctttcc agtcgggaaa cctgtcgtgc cagctgcatt      60
aatgaatcgg ccaacgcgcg gggagaggcg gtttgcgtat tgggcgctct tccgcttcct     120
cgctcactga ctcgctgcgc tcggtcgttc ggctgcggcg agcggtatca gctcactcaa     180
aggcggtaat acggttatcc acagaatcag gggataacgc aggaaagaac atgtgagcaa     240
aaggccagca aaaggccagg aaccgtaaaa aggccgcgtt gctggcgttt ttccataggc     300
tccgcccccc tgacgagcat cacaaaaatc gacgctcaag tcagaggtgg cgaaacccga     360
caggactata aagataccag gcgtttcccc ctggaagctc cctcgtgcgc tctcctgttc     420
cgaccctgcc gcttaccgga tacctgtccg cctttctccc ttcgggaagc gtggcgcttt     480
```

-continued

| | |
|---|---|
| ctcatagctc acgctgtagg tatctcagtt cggtgtaggt cgttcgctcc aagctgggct | 540 |
| gtgtgcacga accccccgtt cagcccgacc gctgcgcctt atccggtaac tatcgtcttg | 600 |
| agtccaaccc ggtaagacac gacttatcgc cactggcagc agccactggt aacaggatta | 660 |
| gcagagcgag gtatgtaggc ggtgctacag agttcttgaa gtggtggcct aactacggct | 720 |
| acactagaag gacagtattt ggtatctgcg ctctgctgaa gccagttacc ttcggaaaaa | 780 |
| gagttggtag ctcttgatcc ggcaaacaaa ccaccgctgg tagcggtggt ttttttgttt | 840 |
| gcaagcagca gattacgcgc agaaaaaaag gatctcaaga agatcctttg atcttttcta | 900 |
| cggggtctga cgctcagtgg aacgaaaact cacgttaagg gattttggtc atgagattat | 960 |
| caaaaaggat cttcacctag atccttttaa attaaaaatg aagttttaaa tcaatctaaa | 1020 |
| gtatatatga gtaaacttgg tctgacagtt accaatgctt aatcagtgag gcacctatct | 1080 |
| cagcgatctg tctatttcgt tcatccatag ttgcctgact ccccgtcgtg tagataacta | 1140 |
| cgatacggga gggcttacca tctggcccca gtgctgcaat gataccgcga gacccacgct | 1200 |
| caccggctcc agatttatca gcaataaacc agccagccgg aagggccgag cgcagaagtg | 1260 |
| gtcagcttgg ctgccatttt tggggtgagg ccgttcgcgg ccgaggggcg cagcccctgg | 1320 |
| ggggatggga ggcccgcgtt agcgggccgg gagggttcga gaaggggggg cacccccctt | 1380 |
| cggcgtgcgc ggtcacgcgc acagggcgca gccctggtta aaaacaaggt ttataaatat | 1440 |
| tggtttaaaa gcaggttaaa agacaggtta gcggtggccg aaaaacgggc ggaaaccctt | 1500 |
| gcaaatgctg gattttctgc ctgtggacag cccctcaaat gtcaataggt gcgcccctca | 1560 |
| tctgtcagca ctctgcccct caagtgtcaa ggatcgcgcc cctcatctgt cagtagtcgc | 1620 |
| gcccctcaag tgtcaatacc gcagggcact tatccccagg cttgtccaca tcatctgtgg | 1680 |
| gaaactcgcg taaaatcagg cgttttcgcc gatttgcgag gctggccagc tccacgtcgc | 1740 |
| cggccgaaat cgagcctgcc cctcatctgt caacgccgcg ccgggtgagt cggcccctca | 1800 |
| agtgtcaacg tccgccccctc atctgtcagt gagggccaag ttttccgcga ggtatccaca | 1860 |
| acgccggcgg ccgcggtgtc tcgcacacgg cttcgacggc gtttctggcg cgtttgcagg | 1920 |
| gccatagacg gccgccagcc cagcggcgag ggcaaccagc ccggtgagcg tcggaaaggg | 1980 |
| tcgacggatc ttttccgctg cataaccctg cttcggggtc attatagcga ttttttcggt | 2040 |
| atatccatcc ttttcgcac gatatacagg attttgccaa agggttcgtg tagactttcc | 2100 |
| ttggtgtatc caacggcgtc agccgggcag gataggtgaa gtaggcccac ccgcgagcgg | 2160 |
| gtgttccttc ttcactgtcc cttattcgca cctggcggtg ctcaacggga atcctgctct | 2220 |
| gcgaggctgg ccggctaccg ccggcgtaac agatgagggc aagcggatgg ctgatgaaac | 2280 |
| caagccaacc aggaagggca gcccacctat caaggtgtac tgccttccag acgaacgaag | 2340 |
| agcgattgag gaaaaggcgg cggcggccgg catgagcctg taggcctacc tgctggccgt | 2400 |
| cggccagggc tacaaaatca cgggcgtcgt ggactatgag cacgtccgcg agctggcccg | 2460 |
| catcaatggc gacctgggcc gcctgggcgg cctgctgaaa ctctggctca ccgacgaccc | 2520 |
| gcgcacggcg cggttcggtg atgccacgat cctcgccctg ctggcgaaga tcgaagagaa | 2580 |
| gcaggacgag cttggcaagg tcatgatggg cgtggtccgc ccgagggcag agccatgact | 2640 |
| tttttagccg ctaaaacggc cggggggtgc gcgtgattgc caagcacgtc cccatgcgct | 2700 |
| ccatcaagaa gagcgacttc gcggagctgg tattcgtgca gggcaagatt cggaatacca | 2760 |
| agtacgagaa ggacgccag acggtctacg ggaccgactt cattgccgat aaggtggatt | 2820 |
| atctggacac caaggcacca ggcgggtcaa atcaggaata agggcacatt gccccggcgt | 2880 |

```
gagtcggggc aatcccgcaa ggagggtgaa tgaatcggac gtttgaccgg aaggcataca    2940
ggcaagaact gatcgacgcg gggttttccg ccgaggatgc cgaaaccatc gcaagccgca    3000
ccgtcatgcg tgcgccccgc gaaaccttcc agtccgtcgg ctcgatggtc cagcaagcta    3060
cggccaagat cgagcgcgac agcgtgcaac tggctccccc tgccctgccc gcgccatcgg    3120
ccgccgtgga gcgttcgcgt cgtctcgaac aggaggcggc aggtttggcg aagtcgatga    3180
ccatcgacac gcgaggaact atgacgacca agaagcgaaa aaccgccggc gaggacctgg    3240
caaaacaggt cagcgaggcc aagcaggccg cgttgctgaa acacacgaag cagcagatca    3300
aggaaatgca gctttccttg ttcgatattg cgccgtggcc ggacacgatg cgagcgatgc    3360
caaacgacac ggcccgctct gccctgttca ccacgcgcaa caagaaaatc ccgcgcgagg    3420
cgctgcaaaa caaggtcatt ttccacgtca acaaggacgt gaagatcacc tacaccggcg    3480
tcgagctgcg ggccgacgat gacgaactgg tgtggcagca ggtgttggag tacgcgaagc    3540
gcacccctat cggcgagccg atcaccttca cgttctacga gctttgccag gacctgggct    3600
ggtcgatcaa tggccggtat tacacgaagg ccgaggaatg cctgtcgcgc ctacaggcga    3660
cggcgatggg cttcacgtcc gaccgcgttg ggcacctgga atcggtgtcg ctgctgcacc    3720
gcttccgcgt cctggaccgt ggcaagaaaa cgtcccgttg ccaggtcctg atcgacgagg    3780
aaatcgtcgt gctgtttgct ggcgaccact acacgaaatt catatgggag aagtaccgca    3840
agctgtcgcc gacggcccga cggatgttcg actatttcag ctcgcaccgg agccgtacc    3900
cgctcaagct ggaaaccttc cgcctcatgt gcggatcgga ttccacccgc gtgaagaagt    3960
ggcgcgagca ggtcggcgaa gcctgcgaag agttgcgagg cagcggcctg gtggaacacg    4020
cctgggtcaa tgatgacctg gtgcattgca aacgctaggg ccttgtgggg tcagttccgg    4080
ctgggggttc agcagccagc gctttactgg catttcagga acaagcgggc actgctcgac    4140
gcacttgctt cgctcagtat cgctcgggac gcacggcgcg ctctacgaac tgccgataaa    4200
cagaggatta aaattgacaa ttctagggcg cgtatagctt gccggaagtc gccttgaccc    4260
gcatggcata ggcctatcgt ttccacgatc agcgatcggc tcgttgccct gcgccgctcc    4320
aaagcccgcg acgcagcgcc ggcaggcaga gcaagtagag ggcagcgcct gcaatccatg    4380
cccacccgtt ccacgttgtt atagaagccg catagatcgc cgtgaagagg aggggtccga    4440
cgatcgaggt caggctggtg agcgccgcca gtgagccttg cagctgcccc tgacgttcct    4500
catccacctg cctggacaac attgcttgca gcgccggcat tccgatgcca cccgaagcaa    4560
gcaggaccat gatcgggaac gccatccatc cccgtgtcgg acctgcaggg ggggggggga    4620
aagccacgtt gtgtctcaaa atctctgatg ttacattgca caagataaaa atatatcatc    4680
atgaacaata aaactgtctg cttacataaa cagtaataca aggggtgtta tgagccatat    4740
tcaacgggaa acgtcttgct cgaggccgcg attaaattcc aacatggatg ctgatttata    4800
tgggtataaa tgggctcgcg ataatgtcgg gcaatcaggt gcgacaatct atcgattgta    4860
tgggaagccc gatgcgccag agttgtttct gaaacatggc aaaggtagcg ttgccaatga    4920
tgttacagat gagatggtca gactaaactg gctgacggaa tttatgcctc ttccgaccat    4980
caagcatttt atccgtactc ctgatgatgc atggttactc accactgcga tccccgggaa    5040
aacagcattc caggtattag aagaatatcc tgattcaggt gaaaatattg ttgatgcgct    5100
ggcagtgttc ctgcgccggt tgcattcgat tcctgtttgt aattgtcctt ttaacagcga    5160
tcgcgtattt cgtctcgctc aggcgcaatc acgaatgaat aacggtttgg ttgatgcgag    5220
```

| | | |
|---|---|---|
| tgattttgat gacgagcgta atggctggcc tgttgaacaa gtctggaaag aaatgcataa | 5280 | |
| gcttttgcca ttctcaccgg attcagtcgt cactcatggt gatttctcac ttgataacct | 5340 | |
| tatttttgac gaggggaaat taataggttg tattgatgtt ggacgagtcg gaatcgcaga | 5400 | |
| ccgataccag gatcttgcca tcctatggaa ctgcctcggt gagttttctc cttcattaca | 5460 | |
| gaaacggctt tttcaaaaat atggtattga taatcctgat atgaataaat tgcagtttca | 5520 | |
| tttgatgctc gatgagtttt tctaatcaga attggttaat tggttgtaac actggcagag | 5580 | |
| cattacgctg acttgacggg acggcggctt tgttgaataa atcgaacttt tgctgagttg | 5640 | |
| aaggatcaga tcacgcatct tcccgacaac gcagaccgtt ccgtggcaaa gcaaaagttc | 5700 | |
| aaaatcacca actggtccac ctacaacaaa gctctcatca accgtggctc cctcactttc | 5760 | |
| tggctggatg atggggcgat tcaggcctgg tatgagtcag caacaccttc ttcacgaggc | 5820 | |
| agacctcagc gccccccccc ccctgcaggt catcggcaat ataagcgccg gctaccgccc | 5880 | |
| cagtcgcccc ggtgatgccg gccacgatcc gcccgatata gagaacccaa aggaaaggcg | 5940 | |
| ctgtcgccat gatggcgtag tcgacagtgg cgccggccag cgagacgagc aagattggcc | 6000 | |
| gccgccgaa acgatccgac agcgcgccca gcacaggtgc gcaggcaaat tgcaccaacg | 6060 | |
| catacagcgc cagcagaatg ccatagtggg cggtgacgtc gttcgagtg | 6109 | |

```
<210> SEQ ID NO 28
<211> LENGTH: 861
<212> TYPE: DNA
<213> ORGANISM: Artificial Sequence
<220> FEATURE:
<223> OTHER INFORMATION: AmpR gene (from vector pCR2.1-TOPO - Ali and
      Murrell 2009)

<400> SEQUENCE: 28
```

| | | |
|---|---|---|
| atgagtattc aacatttccg tgtcgccctt attccctttt ttgcggcatt ttgccttcct | 60 | |
| gttttgctc acccagaaac gctggtgaaa gtaaaagatg ctgaagatca gttgggtgca | 120 | |
| cgagtgggtt acatcgaact ggatctcaac agcggtaaga tccttgagag ttttcgcccc | 180 | |
| gaagaacgtt ttccaatgat gagcactttt aaagttctgc tatgtggcgc ggtattatcc | 240 | |
| cgtattgacg ccgggcaaga gcaactcggt cgccgcatac actattctca gaatgacttg | 300 | |
| gttgagtact caccagtcac agaaaagcat cttacggatg gcatgacagt aagagaatta | 360 | |
| tgcagtgctg ccataaccat gagtgataac actgcggcca acttacttct gacaacgatc | 420 | |
| ggaggaccga aggagctaac cgcttttttg cacaacatgg gggatcatgt aactcgcctt | 480 | |
| gatcgttggg aaccggagct gaatgaagcc ataccaaacg acgagcgtga ccacacgatg | 540 | |
| cctgtagcaa tggcaacaac gttgcgcaaa ctattaactg gcgaactact tactctagct | 600 | |
| tcccggcaac aattaataga ctggatggag gcggataaag ttgcaggacc acttctgcgc | 660 | |
| tcggcccttc cggctggctg gtttattgct gataaatctg gagccggtga gcgtgggtct | 720 | |
| cgcggtatca ttgcagcact ggggccagat ggtaagccct cccgtatcgt agttatctac | 780 | |
| acgacgggga gtcaggcaac tatggatgaa cgaaatagac agatcgctga gataggtgcc | 840 | |
| tcactgatta agcattggta a | 861 | |

```
<210> SEQ ID NO 29
<211> LENGTH: 286
<212> TYPE: PRT
<213> ORGANISM: Artificial Sequence
<220> FEATURE:
<223> OTHER INFORMATION: AmpR protein
```

<400> SEQUENCE: 29

Met Ser Ile Gln His Phe Arg Val Ala Leu Ile Pro Phe Phe Ala Ala
1               5                   10                  15

Phe Cys Leu Pro Val Phe Ala His Pro Glu Thr Leu Val Lys Val Lys
            20                  25                  30

Asp Ala Glu Asp Gln Leu Gly Ala Arg Val Gly Tyr Ile Glu Leu Asp
        35                  40                  45

Leu Asn Ser Gly Lys Ile Leu Glu Ser Phe Arg Pro Glu Glu Arg Phe
    50                  55                  60

Pro Met Met Ser Thr Phe Lys Val Leu Leu Cys Gly Ala Val Leu Ser
65                  70                  75                  80

Arg Ile Asp Ala Gly Gln Glu Gln Leu Gly Arg Arg Ile His Tyr Ser
                85                  90                  95

Gln Asn Asp Leu Val Glu Tyr Ser Pro Val Thr Glu Lys His Leu Thr
            100                 105                 110

Asp Gly Met Thr Val Arg Glu Leu Cys Ser Ala Ala Ile Thr Met Ser
        115                 120                 125

Asp Asn Thr Ala Ala Asn Leu Leu Leu Thr Thr Ile Gly Gly Pro Lys
    130                 135                 140

Glu Leu Thr Ala Phe Leu His Asn Met Gly Asp His Val Thr Arg Leu
145                 150                 155                 160

Asp Arg Trp Glu Pro Glu Leu Asn Glu Ala Ile Pro Asn Asp Glu Arg
                165                 170                 175

Asp Thr Thr Met Pro Val Ala Met Ala Thr Thr Leu Arg Lys Leu Leu
            180                 185                 190

Thr Gly Glu Leu Leu Thr Leu Ala Ser Arg Gln Gln Leu Ile Asp Trp
        195                 200                 205

Met Glu Ala Asp Lys Val Ala Gly Pro Leu Leu Arg Ser Ala Leu Pro
    210                 215                 220

Ala Gly Trp Phe Ile Ala Asp Lys Ser Gly Ala Gly Glu Arg Gly Ser
225                 230                 235                 240

Arg Gly Ile Ile Ala Ala Leu Gly Pro Asp Gly Lys Pro Ser Arg Ile
                245                 250                 255

Val Val Ile Tyr Thr Thr Gly Ser Gln Ala Thr Met Asp Glu Arg Asn
            260                 265                 270

Arg Gln Ile Ala Glu Ile Gly Ala Ser Leu Ile Lys His Trp
        275                 280                 285

<210> SEQ ID NO 30
<211> LENGTH: 327
<212> TYPE: DNA
<213> ORGANISM: Escherichia coli

<400> SEQUENCE: 30
atggcccaac aatcacccta ttcagcagcg atggcagaac agcgtcacca ggagtggtta      60
cgttttgtcg acctgcttaa gaatgcctac caaaacgatc tccatttacc gttgttaaac     120
ctgatgctga cgccagatga gcgcgaagcg ttggggactc gcgtgcgtat tgtcgaagag     180
ctgttgcgcg cgaaatgag ccagcgtgag ttaaaaaatg aactcggcgc aggcatcgcg      240
acgattacgc gtggatctaa cagcctgaaa gccgcgcccg tcgagctgcg ccagtggctg     300
gaagaggtgt tgctgaaaag cgattga                                         327

<210> SEQ ID NO 31
<211> LENGTH: 108

```
<212> TYPE: PRT
<213> ORGANISM: Escherichia coli

<400> SEQUENCE: 31

Met Ala Gln Gln Ser Pro Tyr Ser Ala Ala Met Ala Glu Gln Arg His
1               5                   10                  15

Gln Glu Trp Leu Arg Phe Val Asp Leu Leu Lys Asn Ala Tyr Gln Asn
            20                  25                  30

Asp Leu His Leu Pro Leu Leu Asn Leu Met Leu Thr Pro Asp Glu Arg
        35                  40                  45

Glu Ala Leu Gly Thr Arg Val Arg Ile Val Glu Glu Leu Leu Arg Gly
    50                  55                  60

Glu Met Ser Gln Arg Glu Leu Lys Asn Glu Leu Gly Ala Gly Ile Ala
65                  70                  75                  80

Thr Ile Thr Arg Gly Ser Asn Ser Leu Lys Ala Ala Pro Val Glu Leu
                85                  90                  95

Arg Gln Trp Leu Glu Glu Val Leu Leu Lys Ser Asp
            100                 105

<210> SEQ ID NO 32
<211> LENGTH: 48
<212> TYPE: DNA
<213> ORGANISM: Artificial Sequence
<220> FEATURE:
<223> OTHER INFORMATION: T7 Terminator sequence (T7 RNA polymerase of T7
      phage)

<400> SEQUENCE: 32
ctagcataac cccttggggc ctctaaacgg gtcttgaggg gttttttg                  48

<210> SEQ ID NO 33
<211> LENGTH: 105
<212> TYPE: DNA
<213> ORGANISM: Artificial Sequence
<220> FEATURE:
<223> OTHER INFORMATION: AmpR Promoter gene - from vector pCR2.1-TOPO
      (Ali and Murrell 2009)

<400> SEQUENCE: 33
cgcggaaccc ctatttgttt atttttctaa atacattcaa atatgtatcc gctcatgaga      60
caataaccct gataaatgct tcaataatat tgaaaaagga agagt                    105

<210> SEQ ID NO 34
<211> LENGTH: 1182
<212> TYPE: DNA
<213> ORGANISM: Methylococcus capsulatus

<400> SEQUENCE: 34
atgagcataa aactttccgg cagagtccaa tcggttaaac catcgccaac cctggctatt      60
accgcaagag ccgccgcaat gcgcgccgcc ggcaaggaca tcatcggcct cggcgcgggc     120
gaacccgact tcgacacgcc ggaccacatc aaagccgcag caatagaagc aatgaacaaa     180
ggctttacga atacactcc ggtcgacggc accgcgagct taaaaaaagc gatcatcgaa     240
aaattcaaaa aagacaacgg cctcgattat caaccgaaac aaatcttggt ttcctgcggc     300
ggtaagcaaa gttcttacaa cctgacgcaa gcgttgctga acgacggaga cgaagtcatt     360
attccagccc cttattgggt ctcgtatcct gatatggtgc tgcttgccgg cggcgtgccg     420
gtcgtcatcg aaacaacaca ggcgcagcac tttaaaatat cgccggaaca actgcgcgcg     480
gcgattaccg acaagacccg attaatttc atcaacagcc cgtcgaatcc gaccggcgtc     540
```

```
gcctattcgc tcgacgaact gaaagcactc ggcgatgtgt tgaaagattt tccggacatc    600
atcatcgcga ccgacgacat gtacgaacat atcacctgga aaaaggcgc gttcgtcaac    660 attctgaacg cgcacccgga gttctacgac cgcaccgtcg ttatgaacgg cgtgtctaaa    720
gcttattcga tgaccggctg cgcatcggt tacgcggcag ccctatcga tttgattgaa    780 gcgatgggca cgattcaatc gcaaagcacc tcgaatccga cctcgatttc acaatatgcc    840
gccgaagccg cgctgaacgg cgatcaaggc ttcatcgaca tgatgatgac cgaattcaag    900
aagcgccatg atttcgtggt ctcggaactc aacaaaatcg acggcatcga ttgccttgaa    960
accgacggca cattctacgt attcccgaac gtggaacaag caatcgccaa atggacaac    1020 atcaaagacg acttggattt ttcagaatac ctgatcgaaa atgccggcgt agcgctagtg    1080
ccgggctcgg ccttcggttg tccgggacac gtcagaatat cgatcgcgac cagtatgaaa    1140
aacttggaaa acgcgctgga gagaattaaa aaggcggttt ga    1182
```

<210> SEQ ID NO 35
<211> LENGTH: 393
<212> TYPE: PRT
<213> ORGANISM: Methylococcus capsulatus

<400> SEQUENCE: 35

```
Met Ser Ile Lys Leu Ser Gly Arg Val Gln Ser Val Lys Pro Ser Pro
1               5                   10                  15

Thr Leu Ala Ile Thr Ala Arg Ala Ala Met Arg Ala Ala Gly Lys
            20                  25                  30

Asp Ile Ile Gly Leu Gly Ala Gly Glu Pro Asp Phe Asp Thr Pro Asp
        35                  40                  45

His Ile Lys Ala Ala Ile Glu Ala Met Asn Lys Gly Phe Thr Lys
    50                  55                  60

Tyr Thr Pro Val Asp Gly Thr Ala Ser Leu Lys Lys Ala Ile Ile Glu
65                  70                  75                  80

Lys Phe Lys Lys Asp Asn Gly Leu Asp Tyr Gln Pro Lys Gln Ile Leu
            85                  90                  95

Val Ser Cys Gly Gly Lys Gln Ser Ser Tyr Asn Leu Thr Gln Ala Leu
            100                 105                 110

Leu Asn Asp Gly Asp Glu Val Ile Ile Pro Ala Pro Tyr Trp Val Ser
            115                 120                 125

Tyr Pro Asp Met Val Leu Leu Ala Gly Gly Val Pro Val Ile Glu
        130                 135                 140

Thr Thr Gln Ala Gln His Phe Lys Ile Ser Pro Glu Gln Leu Arg Ala
145                 150                 155                 160

Ala Ile Thr Asp Lys Thr Arg Leu Ile Phe Ile Asn Ser Pro Ser Asn
                165                 170                 175

Pro Thr Gly Val Ala Tyr Ser Leu Asp Glu Leu Lys Ala Leu Gly Asp
            180                 185                 190

Val Leu Lys Asp Phe Pro Asp Ile Ile Ile Ala Thr Asp Asp Met Tyr
            195                 200                 205

Glu His Ile Thr Trp Lys Lys Gly Ala Phe Val Asn Ile Leu Asn Ala
        210                 215                 220

His Pro Glu Phe Tyr Asp Arg Thr Val Val Met Asn Gly Val Ser Lys
225                 230                 235                 240

Ala Tyr Ser Met Thr Gly Trp Arg Ile Gly Tyr Ala Ala Gly Pro Ile
            245                 250                 255
```

```
Asp Leu Ile Glu Ala Met Gly Thr Ile Gln Ser Gln Ser Thr Ser Asn
            260                 265                 270

Pro Thr Ser Ile Ser Gln Tyr Ala Ala Glu Ala Ala Leu Asn Gly Asp
        275                 280                 285

Gln Gly Phe Ile Asp Met Met Met Thr Glu Phe Lys Lys Arg His Asp
    290                 295                 300

Phe Val Val Ser Glu Leu Asn Lys Ile Asp Gly Ile Asp Cys Leu Glu
305                 310                 315                 320

Thr Asp Gly Thr Phe Tyr Val Phe Pro Asn Val Glu Gln Ala Ile Ala
                325                 330                 335

Lys Met Asp Asn Ile Lys Asp Asp Leu Asp Phe Ser Glu Tyr Leu Ile
            340                 345                 350

Glu Asn Ala Gly Val Ala Leu Val Pro Gly Ser Ala Phe Gly Cys Pro
        355                 360                 365

Gly His Val Arg Ile Ser Ile Ala Thr Ser Met Lys Asn Leu Glu Asn
    370                 375                 380

Ala Leu Glu Arg Ile Lys Lys Ala Val
385                 390
```

<210> SEQ ID NO 36
<211> LENGTH: 1413
<212> TYPE: DNA
<213> ORGANISM: Artificial Sequence
<220> FEATURE:
<223> OTHER INFORMATION: FMO gene (codon-optimized) - Corynebacterium
      glutamicum

<400> SEQUENCE: 36

```
atggagatgg tcatgaagaa caagcgggtg gcgatcatcg gcgcgggccc gagcggcatc      60
gcccagctgc gcgccttcga gtcggcgaaa agcagggcc acgagatccc ggagctggtc     120
tgcttcgaga gcaggacac ctggggcggc agtggaact acagctggcg caccggcacc      180
gactcgtacg gcgagccggt ccacagcagc atgtaccgca acctgtggag caacggcccg     240
aaggaggtcc tggagttcgc cgagtactcc ttcgacgagc acttcggcaa gccgatctcg     300
tcctacccgc cgcgcgaggt cctgtgggac tacatcgccg ccgcgccaa gaagtccaac     360 gtggagaagt acatcaagtt cgcccacgtc gtccgctggg tgagcttcga cgaggccacc     420
aagctgttca ccgtgaccgt cgagaacctg cgcaccggcg agaccagcag cgacacctac     480
gacaacgtca tcgtcggcgc gggccacttc tcgttcccga acgtcccgca cttcgacggc     540
gtcgagacct tccccggcca gatcatgcac gcccacgagt tccggggcgc ggaagccgtc     600
gccgacaagg acatcctgct gatcggcgcg tcgtactccg ccgaggacat cggcacccag     660
gcctacaaga tgggcgcgcg cagcgtcacc ttcagctacc gcagcaaccc gatgggctac     720
gagtggccgg aggaaatgac cgaactgccc ctggtcgaac ggttcgacgg cagcgaggtg     780
cacttcgtga acggcgagaa gcggaaggtc gatatcgtcg tcttctgcac cggctacctg     840
caccactacc cgttcatgcc gtccgagctg accctgagca gcccgaacaa cctgtacccc     900
gacaccctgt accgcggcgt cgtctcggaa gccaacaacc agctgttctg gctgggcgcg     960
caggaccagt ggctgacctt caatatgttt gacgcccagg cctggtacgt ccgcgacgtc    1020
atcctgggcc gcgtcgccct gccgagcaag gaagcccagc gcaaccacat ggacaagtgg    1080
ctgtcccgct cgagggcct gaagagcgag aacgaccaga tcgacttcca gtcgactac    1140 gtcgaggacc tgatcgacca gaccgactac ccgagcttcg acctgaagga agtcgccaac    1200
atcctgaagg gctgggtcaa gagcaaggaa gaggacatcc tgaactaccg ggactacacc    1260
```

```
tacacctccg tcatgaccgg caccaccagc gtcgagcacc acaccccgtg gatgatcgag    1320
ctggacgaca gcctggaacg ctacctgagc gaaccccagg aagacgaagc ccgccaggtc    1380
taccgcggca agaaggtccg cgacaaggcg tga                                 1413
```

<210> SEQ ID NO 37
<211> LENGTH: 470
<212> TYPE: PRT
<213> ORGANISM: Corynebacterium glutamicum

<400> SEQUENCE: 37

```
Met Glu Met Val Met Lys Asn Lys Arg Val Ala Ile Ile Gly Ala Gly
1               5                   10                  15

Pro Ser Gly Ile Ala Gln Leu Arg Ala Phe Glu Ser Ala Glu Lys Gln
            20                  25                  30

Gly His Glu Ile Pro Glu Leu Val Cys Phe Glu Lys Gln Asp Thr Trp
        35                  40                  45

Gly Gly Gln Trp Asn Tyr Ser Trp Arg Thr Gly Thr Asp Ser Tyr Gly
    50                  55                  60

Glu Pro Val His Ser Ser Met Tyr Arg Asn Leu Trp Ser Asn Gly Pro
65                  70                  75                  80

Lys Glu Val Leu Glu Phe Ala Glu Tyr Ser Phe Asp Glu His Phe Gly
                85                  90                  95

Lys Pro Ile Ser Ser Tyr Pro Pro Arg Glu Val Leu Trp Asp Tyr Ile
            100                 105                 110

Ala Gly Arg Ala Lys Lys Ser Asn Val Glu Lys Tyr Ile Lys Phe Ala
        115                 120                 125

His Val Val Arg Trp Val Ser Phe Asp Glu Ala Thr Lys Leu Phe Thr
    130                 135                 140

Val Thr Val Glu Asn Leu Arg Thr Gly Glu Thr Ser Ser Asp Thr Tyr
145                 150                 155                 160

Asp Asn Val Ile Val Gly Ala Gly His Phe Ser Phe Pro Asn Val Pro
                165                 170                 175

His Phe Asp Gly Val Glu Thr Phe Pro Gly Gln Ile Met His Ala His
            180                 185                 190

Glu Phe Arg Gly Ala Glu Ala Val Ala Asp Lys Asp Ile Leu Leu Ile
        195                 200                 205

Gly Ala Ser Tyr Ser Ala Glu Asp Ile Gly Thr Gln Ala Tyr Lys Met
    210                 215                 220

Gly Ala Arg Ser Val Thr Phe Ser Tyr Arg Ser Asn Pro Met Gly Tyr
225                 230                 235                 240

Glu Trp Pro Glu Glu Met Thr Glu Leu Pro Leu Val Glu Arg Phe Asp
                245                 250                 255

Gly Ser Glu Val His Phe Val Asn Gly Glu Lys Arg Lys Val Asp Ile
            260                 265                 270

Val Val Phe Cys Thr Gly Tyr Leu His His Tyr Pro Phe Met Pro Ser
        275                 280                 285

Glu Leu Thr Leu Ser Ser Pro Asn Asn Leu Tyr Pro Asp Thr Leu Tyr
    290                 295                 300

Arg Gly Val Val Ser Glu Ala Asn Asn Gln Leu Phe Trp Leu Gly Ala
305                 310                 315                 320

Gln Asp Gln Trp Leu Thr Phe Asn Met Phe Asp Ala Gln Ala Trp Tyr
                325                 330                 335

Val Arg Asp Val Ile Leu Gly Arg Val Ala Leu Pro Ser Lys Glu Ala
```

```
                340                 345                 350
Gln Arg Asn His Met Asp Lys Trp Leu Ser Arg Phe Glu Gly Leu Lys
            355                 360                 365

Ser Glu Asn Asp Gln Ile Asp Phe Gln Cys Asp Tyr Val Glu Asp Leu
        370                 375                 380

Ile Asp Gln Thr Asp Tyr Pro Ser Phe Asp Leu Lys Glu Val Ala Asn
385                 390                 395                 400

Ile Leu Lys Gly Trp Val Lys Ser Lys Glu Glu Asp Ile Leu Asn Tyr
                405                 410                 415

Arg Asp Tyr Thr Tyr Thr Ser Val Met Thr Gly Thr Thr Ser Val Glu
            420                 425                 430

His His Thr Pro Trp Met Ile Glu Leu Asp Asp Ser Leu Glu Arg Tyr
        435                 440                 445

Leu Ser Glu Pro Gln Glu Asp Glu Ala Arg Gln Val Tyr Arg Gly Lys
    450                 455                 460

Lys Val Arg Asp Lys Ala
465                 470

<210> SEQ ID NO 38
<211> LENGTH: 1071
<212> TYPE: DNA
<213> ORGANISM: Escherichia coli
<220> FEATURE:
<221> NAME/KEY: mutation
<222> LOCATION: (1)..(1071)
<223> OTHER INFORMATION: mutant AroF (N8K mutant)

<400> SEQUENCE: 38
atgcaaaaag acgcgctgaa taaggtacat attaccgacg aacaggtttt aatgactccg      60
gaacaactga aggccgcttt tccattgagc ctgcaacaag aagcccagat tgctgactcg     120
cgtaaaagca tttcagatat tatcgccggg cgcgatcctc gtctgctggt agtatgtggt     180
ccttgttcca ttcatgatcc ggaaactgct ctggaatatg ctcgtcgatt aaagcccctt     240
gccgcagagg tcagcgatag cctctatctg gtaatgcgcg tctattttga aaaaccccgt     300
accactgtcg gctggaaagg gttaattaac gatccccata tggatggctc ttttgatgta     360
gaagccgggc tgcagatcgc gcgtaaattg ctgcttgagc tggtgaatat gggactgcca     420
ctggcgacga agcgttaga tccgaatagc ccgcaatacc tgggcgatct gtttagctgg     480
tcagcaattg gtgctcgtac aacggaatcg caaactcacc gtgaaatggc ctccgggctt     540
tccatgccgg ttggttttaa aaacggcacc gacggcagtc tggcaacagc aattaacgct     600
atgcgcgccg ccgcccagcc gcaccgtttt gttggcatta accaggcagg gcaggttgcg     660
ttgctacaaa ctcaggggaa tccggacggc catgtgatcc tgcgcggtgg taaagcgccg     720
aactatagcc ctgcggatgt tgcgcaatgt gaaaaagaga tggaacaggc gggactgcgc     780
ccgtctctga tggtagattg cagccacggt aattccaata agattatcg ccgtcagcct     840 gcggtggcag aatccgtggt tgctcaaatc aaagatggca atcgctcaat tattggtctg     900
atgatcgaaa gtaatatcca cgagggcaat cagtcttccg agcaaccgcg cagtgaaatg     960
aaatacggtg tatccgtaac cgatgcctgc attagctggg aaatgaccga tgccttgctg    1020
cgtgaaattc atcaggatct gaacgggcag ctgacggctc gcgtggctta a             1071

<210> SEQ ID NO 39
<211> LENGTH: 356
<212> TYPE: PRT
<213> ORGANISM: Escherichia coli
```

```
<220> FEATURE:
<221> NAME/KEY: MUTAGEN
<222> LOCATION: (1)..(356)
<223> OTHER INFORMATION: mutant AroF protein (N8K mutant)

<400> SEQUENCE: 39
```

Met Gln Lys Asp Ala Leu Asn Lys Val His Ile Thr Asp Glu Gln Val
1               5                   10                  15

Leu Met Thr Pro Glu Gln Leu Lys Ala Ala Phe Pro Leu Ser Leu Gln
            20                  25                  30

Gln Glu Ala Gln Ile Ala Asp Ser Arg Lys Ser Ile Ser Asp Ile Ile
        35                  40                  45

Ala Gly Arg Asp Pro Arg Leu Leu Val Val Cys Gly Pro Cys Ser Ile
50                  55                  60

His Asp Pro Glu Thr Ala Leu Glu Tyr Ala Arg Arg Phe Lys Ala Leu
65                  70                  75                  80

Ala Ala Glu Val Ser Asp Ser Leu Tyr Leu Val Met Arg Val Tyr Phe
                85                  90                  95

Glu Lys Pro Arg Thr Thr Val Gly Trp Lys Gly Leu Ile Asn Asp Pro
            100                 105                 110

His Met Asp Gly Ser Phe Asp Val Glu Ala Gly Leu Gln Ile Ala Arg
        115                 120                 125

Lys Leu Leu Leu Glu Leu Val Asn Met Gly Leu Pro Leu Ala Thr Glu
130                 135                 140

Ala Leu Asp Pro Asn Ser Pro Gln Tyr Leu Gly Asp Leu Phe Ser Trp
145                 150                 155                 160

Ser Ala Ile Gly Ala Arg Thr Thr Glu Ser Gln Thr His Arg Glu Met
                165                 170                 175

Ala Ser Gly Leu Ser Met Pro Val Gly Phe Lys Asn Gly Thr Asp Gly
            180                 185                 190

Ser Leu Ala Thr Ala Ile Asn Ala Met Arg Ala Ala Gln Pro His
        195                 200                 205

Arg Phe Val Gly Ile Asn Gln Ala Gly Gln Val Ala Leu Leu Gln Thr
210                 215                 220

Gln Gly Asn Pro Asp Gly His Val Ile Leu Arg Gly Gly Lys Ala Pro
225                 230                 235                 240

Asn Tyr Ser Pro Ala Asp Val Ala Gln Cys Glu Lys Glu Met Glu Gln
                245                 250                 255

Ala Gly Leu Arg Pro Ser Leu Met Val Asp Cys Ser His Gly Asn Ser
            260                 265                 270

Asn Lys Asp Tyr Arg Arg Gln Pro Ala Val Ala Glu Ser Val Val Ala
        275                 280                 285

Gln Ile Lys Asp Gly Asn Arg Ser Ile Ile Gly Leu Met Ile Glu Ser
290                 295                 300

Asn Ile His Glu Gly Asn Gln Ser Ser Glu Gln Pro Arg Ser Glu Met
305                 310                 315                 320

Lys Tyr Gly Val Ser Val Thr Asp Ala Cys Ile Ser Trp Glu Met Thr
                325                 330                 335

Asp Ala Leu Leu Arg Glu Ile His Gln Asp Leu Asn Gly Gln Leu Thr
            340                 345                 350

Ala Arg Val Ala
355

```
<210> SEQ ID NO 40
<211> LENGTH: 1071
```

```
<212> TYPE: DNA
<213> ORGANISM: Escherichia coli
<220> FEATURE:
<221> NAME/KEY: mutation
<222> LOCATION: (1)..(1071)
<223> OTHER INFORMATION: mutant AroF gene (P148L mutant)

<400> SEQUENCE: 40
atgcaaaaag acgcgctgaa taacgtacat attaccgacg aacaggtttt aatgactccg      60
gaacaactga aggccgcttt tccattgagc ctgcaacaag aagcccagat tgctgactcg     120
cgtaaaagca tttcagatat tatcgccggg cgcgatcctc gtctgctggt agtatgtggt     180
ccttgttcca ttcatgatcc ggaaactgct ctggaatatg ctcgtcgatt taaagccctt     240
gccgcagagg tcagcgatag cctctatctg gtaatgcgcg tctattttga aaaaccccgt     300
accactgtcg gctggaaagg gttaattaac gatccccata tggatggctc ttttgatgta     360
gaagccgggc tgcagatcgc gcgtaaattg ctgcttgagc tggtgaatat gggactgcca     420
ctggcgacgg aagcgttaga tctgaatagc ccgcaatacc tgggcgatct gtttagctgg     480
tcagcaattg gtgctcgtac aacggaatcg caaactcacc gtgaaatggc tccgggctt     540
tccatgccgt tggttttaa aaacggcacc gacggcagtc tggcaacagc aattaacgct     600
atgcgcgccg ccgcccagcc gcaccgtttt gttggcatta ccaggcagg gcaggttgcg     660
ttgctacaaa ctcaggggaa tccggacggc atgtgatcc tgcgcggtgg taaagcgccg     720
aactatagcc ctgcggatgt tgcgcaatgt gaaaaagaga tggaacaggc gggactgcgc     780
ccgtctctga tggtagattg cagccacggt aattccaata agattatcg ccgtcagcct     840
gcggtggcag aatccgtggt tgctcaaatc aaagatggca atcgctcaat tattggtctg     900
atgatcgaaa gtaatatcca cgagggcaat cagtcttccg agcaaccgcg cagtgaaatg     960
aaatacggtg tatccgtaac cgatgcctgc attagctggg aaatgaccga tgccttgctg    1020
cgtgaaattc atcaggatct gaacgggcag ctgacggctc gcgtggctta a             1071

<210> SEQ ID NO 41
<211> LENGTH: 356
<212> TYPE: PRT
<213> ORGANISM: Escherichia coli
<220> FEATURE:
<221> NAME/KEY: MUTAGEN
<222> LOCATION: (1)..(356)
<223> OTHER INFORMATION: mutant AroF protein (P148L mutant)

<400> SEQUENCE: 41

Met Gln Lys Asp Ala Leu Asn Asn Val His Ile Thr Asp Glu Gln Val
1               5                   10                  15

Leu Met Thr Pro Glu Gln Leu Lys Ala Ala Phe Pro Leu Ser Leu Gln
            20                  25                  30

Gln Glu Ala Gln Ile Ala Asp Ser Arg Lys Ser Ile Ser Asp Ile Ile
        35                  40                  45

Ala Gly Arg Asp Pro Arg Leu Leu Val Val Cys Gly Pro Cys Ser Ile
    50                  55                  60

His Asp Pro Glu Thr Ala Leu Glu Tyr Ala Arg Arg Phe Lys Ala Leu
65                  70                  75                  80

Ala Ala Glu Val Ser Asp Ser Leu Tyr Leu Val Met Arg Val Tyr Phe
                85                  90                  95

Glu Lys Pro Arg Thr Thr Val Gly Trp Lys Gly Leu Ile Asn Asp Pro
            100                 105                 110

His Met Asp Gly Ser Phe Asp Val Glu Ala Gly Leu Gln Ile Ala Arg
```

```
            115                 120                 125
Lys Leu Leu Leu Glu Leu Val Asn Met Gly Leu Pro Leu Ala Thr Glu
    130                 135                 140

Ala Leu Asp Leu Asn Ser Pro Gln Tyr Leu Gly Asp Leu Phe Ser Trp
145                 150                 155                 160

Ser Ala Ile Gly Ala Arg Thr Thr Glu Ser Gln Thr His Arg Glu Met
                165                 170                 175

Ala Ser Gly Leu Ser Met Pro Val Gly Phe Lys Asn Gly Thr Asp Gly
            180                 185                 190

Ser Leu Ala Thr Ala Ile Asn Ala Met Arg Ala Ala Gln Pro His
        195                 200                 205

Arg Phe Val Gly Ile Asn Gln Ala Gly Gln Val Ala Leu Leu Gln Thr
    210                 215                 220

Gln Gly Asn Pro Asp Gly His Val Ile Leu Arg Gly Gly Lys Ala Pro
225                 230                 235                 240

Asn Tyr Ser Pro Ala Asp Val Ala Gln Cys Glu Lys Glu Met Glu Gln
                245                 250                 255

Ala Gly Leu Arg Pro Ser Leu Met Val Asp Cys Ser His Gly Asn Ser
            260                 265                 270

Asn Lys Asp Tyr Arg Arg Gln Pro Ala Val Ala Glu Ser Val Val Ala
        275                 280                 285

Gln Ile Lys Asp Gly Asn Arg Ser Ile Ile Gly Leu Met Ile Glu Ser
    290                 295                 300

Asn Ile His Glu Gly Asn Gln Ser Ser Glu Gln Pro Arg Ser Glu Met
305                 310                 315                 320

Lys Tyr Gly Val Ser Val Thr Asp Ala Cys Ile Ser Trp Glu Met Thr
                325                 330                 335

Asp Ala Leu Leu Arg Glu Ile His Gln Asp Leu Asn Gly Gln Leu Thr
            340                 345                 350

Ala Arg Val Ala
        355

<210> SEQ ID NO 42
<211> LENGTH: 1071
<212> TYPE: DNA
<213> ORGANISM: Escherichia coli
<220> FEATURE:
<221> NAME/KEY: mutation
<222> LOCATION: (1)..(1071)
<223> OTHER INFORMATION: mutant AroF gene (Q152I mutant)

<400> SEQUENCE: 42
atgcaaaaag acgcgctgaa taacgtacat attaccgacg aacaggtttt aatgactccg      60
gaacaactga aggccgcttt tccattgagc ctgcaacaag aagcccagat tgctgactcg     120
cgtaaaagca tttcagatat tatcgccggg cgcgatcctc gtctgctggt agtatgtggt     180
ccttgttcca ttcatgatcc ggaaactgct ctggaatatg ctcgtcgatt taaagccctt     240
gccgcagagg tcagcgatag cctctatctg gtaatgcgcg tctattttga aaaccccgt      300 accactgtcg gctggaaagg gttaattaac gatccccata tggatggctc ttttgatgta     360
gaagccgggc tgcagatcgc gcgtaaattg ctgcttgagc tggtgaatat gggactgcca     420
ctggcgacgg aagcgttaga tccgaatagc ccgatatacc tgggcgatct gtttagctgg     480
tcagcaattg gtgctcgtac aacggaatcg caaactcacc gtgaaatggc ctccgggctt     540
tccatgccgg ttggttttaa aaacggcacc gacggcagtc tggcaacagc aattaacgct     600
```

```
atgcgcgccg ccgcccagcc gcaccgtttt gttggcatta accaggcagg gcaggttgcg      660
ttgctacaaa ctcaggggaa tccggacggc catgtgatcc tgcgcggtgg taaagcgccg      720
aactatagcc ctgcggatgt tgcgcaatgt gaaaaagaga tggaacaggc gggactgcgc      780
ccgtctctga tggtagattg cagccacggt aattccaata aagattatcg ccgtcagcct      840
gcggtggcag aatccgtggt tgctcaaatc aaagatggca atcgctcaat tattggtctg      900
atgatcgaaa gtaatatcca cgagggcaat cagtcttccg agcaaccgcg cagtgaaatg      960
aaatacggtg tatccgtaac cgatgcctgc attagctggg aaatgaccga tgccttgctg     1020
cgtgaaattc atcaggatct gaacgggcag ctgacggctc gcgtggctta a              1071
```

<210> SEQ ID NO 43
<211> LENGTH: 356
<212> TYPE: PRT
<213> ORGANISM: Escherichia coli
<220> FEATURE:
<221> NAME/KEY: MUTAGEN
<222> LOCATION: (1)..(356)
<223> OTHER INFORMATION: mutant AroF protein (Q152I mutant)

<400> SEQUENCE: 43

```
Met Gln Lys Asp Ala Leu Asn Asn Val His Ile Thr Asp Glu Gln Val
1               5                   10                  15

Leu Met Thr Pro Glu Gln Leu Lys Ala Ala Phe Pro Leu Ser Leu Gln
            20                  25                  30

Gln Glu Ala Gln Ile Ala Asp Ser Arg Lys Ser Ile Ser Asp Ile Ile
        35                  40                  45

Ala Gly Arg Asp Pro Arg Leu Leu Val Val Cys Gly Pro Cys Ser Ile
    50                  55                  60

His Asp Pro Glu Thr Ala Leu Glu Tyr Ala Arg Arg Phe Lys Ala Leu
65                  70                  75                  80

Ala Ala Glu Val Ser Asp Ser Leu Tyr Leu Val Met Arg Val Tyr Phe
                85                  90                  95

Glu Lys Pro Arg Thr Thr Val Gly Trp Lys Gly Leu Ile Asn Asp Pro
            100                 105                 110

His Met Asp Gly Ser Phe Asp Val Glu Ala Gly Leu Gln Ile Ala Arg
        115                 120                 125

Lys Leu Leu Leu Glu Leu Val Asn Met Gly Leu Pro Leu Ala Thr Glu
    130                 135                 140

Ala Leu Asp Pro Asn Ser Pro Ile Tyr Leu Gly Asp Leu Phe Ser Trp
145                 150                 155                 160

Ser Ala Ile Gly Ala Arg Thr Thr Glu Ser Gln Thr His Arg Glu Met
                165                 170                 175

Ala Ser Gly Leu Ser Met Pro Val Gly Phe Lys Asn Gly Thr Asp Gly
            180                 185                 190

Ser Leu Ala Thr Ala Ile Asn Ala Met Arg Ala Ala Gln Pro His
        195                 200                 205

Arg Phe Val Gly Ile Asn Gln Ala Gly Gln Val Ala Leu Leu Gln Thr
    210                 215                 220

Gln Gly Asn Pro Asp Gly His Val Ile Leu Arg Gly Gly Lys Ala Pro
225                 230                 235                 240

Asn Tyr Ser Pro Ala Asp Val Ala Gln Cys Glu Lys Glu Met Glu Gln
                245                 250                 255

Ala Gly Leu Arg Pro Ser Leu Met Val Asp Cys Ser His Gly Asn Ser
            260                 265                 270
```

```
Asn Lys Asp Tyr Arg Arg Gln Pro Ala Val Ala Glu Ser Val Val Ala
            275                 280                 285
Gln Ile Lys Asp Gly Asn Arg Ser Ile Ile Gly Leu Met Ile Glu Ser
        290                 295                 300
Asn Ile His Glu Gly Asn Gln Ser Ser Glu Gln Pro Arg Ser Glu Met
305                 310                 315                 320
Lys Tyr Gly Val Ser Val Thr Asp Ala Cys Ile Ser Trp Glu Met Thr
                325                 330                 335
Asp Ala Leu Leu Arg Glu Ile His Gln Asp Leu Asn Gly Gln Leu Thr
            340                 345                 350
Ala Arg Val Ala
        355

<210> SEQ ID NO 44
<211> LENGTH: 1068
<212> TYPE: DNA
<213> ORGANISM: Escherichia coli
<220> FEATURE:
<221> NAME/KEY: mutation
<222> LOCATION: (1)..(1068)
<223> OTHER INFORMATION: mutant AroF gene (del Ile11 mutant)

<400> SEQUENCE: 44
```

| | | | | | |
|---|---|---|---|---|---|
| atgcaaaaag | acgcgctgaa | taacgtacat | accgacgaac | aggttttaat gactccggaa |    60 |
| caactgaagg | ccgcttttcc | attgagcctg | caacaagaag | cccagattgc tgactcgcgt |   120 |
| aaaagcattt | cagatattat | cgccgggcgc | gatcctcgtc | tgctggtagt atgtggtcct |   180 |
| tgttccattc | atgatccgga | aactgctctg | gaatatgctc | gtcgatttaa agcccttgcc |   240 |
| gcagaggtca | gcgatagcct | ctatctggta | atgcgcgtct | attttgaaaa accccgtacc |   300 |
| actgtcggct | ggaaagggtt | aattaacgat | ccccatatgg | atggctcttt tgatgtagaa |   360 |
| gccgggctgc | agatcgcgcg | taaattgctg | cttgagctgg | tgaatatggg actgccactg |   420 |
| gcgacggaag | cgttagatcc | gaatagcccg | caatacctgg | cgatctgtt tagctggtca |   480 |
| gcaattggtg | ctcgtacaac | ggaatcgcaa | actcaccgtg | aaatggcctc cgggctttcc |   540 |
| atgccggttg | ttttaaaaaa | cggcaccgac | ggcagtctgg | caacagcaat taacgctatg |   600 |
| cgcgccgccg | cccagccgca | ccgttttgtt | ggcattaacc | aggcagggca ggttgcgttg |   660 |
| ctacaaactc | aggggaatcc | ggacggccat | gtgatcctgc | gcggtggtaa agcgccgaac |   720 |
| tatagccctg | cggatgttgc | gcaatgtgaa | aaagagatgg | aacaggcggg actgcgcccg |   780 |
| tctctgatgg | tagattgcag | ccacggtaat | tccaataaag | attatcgccg tcagcctgcg |   840 |
| gtggcagaat | ccgtggttgc | tcaaatcaaa | gatggcaatc | gctcaattat tggtctgatg |   900 |
| atcgaaagta | atatccacga | gggcaatcag | tcttccgagc | aaccgcgcag tgaaatgaaa |   960 |
| tacggtgtat | ccgtaaccga | tgcctgcatt | agctgggaaa | tgaccgatgc cttgctgcgt |  1020 |
| gaaattcatc | aggatctgaa | cgggcagctg | acggctcgcg | tggcttaa              |  1068 |

```
<210> SEQ ID NO 45
<211> LENGTH: 355
<212> TYPE: PRT
<213> ORGANISM: Escherichia coli
<220> FEATURE:
<221> NAME/KEY: MUTAGEN
<222> LOCATION: (1)..(355)
<223> OTHER INFORMATION: mutant AroF protein (del Ile11 mutant)

<400> SEQUENCE: 45

Met Gln Lys Asp Ala Leu Asn Asn Val His Thr Asp Glu Gln Val Leu
```

```
1               5                   10                  15
Met Thr Pro Glu Gln Leu Lys Ala Ala Phe Pro Leu Ser Leu Gln Gln
            20                  25                  30

Glu Ala Gln Ile Ala Asp Ser Arg Lys Ser Ile Ser Asp Ile Ile Ala
            35                  40                  45

Gly Arg Asp Pro Arg Leu Leu Val Val Cys Gly Pro Cys Ser Ile His
50                          55                  60

Asp Pro Glu Thr Ala Leu Glu Tyr Ala Arg Arg Phe Lys Ala Leu Ala
65                      70                  75                  80

Ala Glu Val Ser Asp Ser Leu Tyr Leu Val Met Arg Val Tyr Phe Glu
                85                  90                  95

Lys Pro Arg Thr Thr Val Gly Trp Lys Gly Leu Ile Asn Asp Pro His
                100                 105                 110

Met Asp Gly Ser Phe Asp Val Glu Ala Gly Leu Gln Ile Ala Arg Lys
                115                 120                 125

Leu Leu Leu Glu Leu Val Asn Met Gly Leu Pro Leu Ala Thr Glu Ala
130                 135                 140

Leu Asp Pro Asn Ser Pro Gln Tyr Leu Gly Asp Leu Phe Ser Trp Ser
145                 150                 155                 160

Ala Ile Gly Ala Arg Thr Thr Glu Ser Gln Thr His Arg Glu Met Ala
                165                 170                 175

Ser Gly Leu Ser Met Pro Val Gly Phe Lys Asn Gly Thr Asp Gly Ser
                180                 185                 190

Leu Ala Thr Ala Ile Asn Ala Met Arg Ala Ala Ala Gln Pro His Arg
                195                 200                 205

Phe Val Gly Ile Asn Gln Ala Gly Gln Val Ala Leu Leu Gln Thr Gln
210                 215                 220

Gly Asn Pro Asp Gly His Val Ile Leu Arg Gly Gly Lys Ala Pro Asn
225                 230                 235                 240

Tyr Ser Pro Ala Asp Val Ala Gln Cys Glu Lys Glu Met Glu Gln Ala
                245                 250                 255

Gly Leu Arg Pro Ser Leu Met Val Asp Cys Ser His Gly Asn Ser Asn
                260                 265                 270

Lys Asp Tyr Arg Arg Gln Pro Ala Val Ala Glu Ser Val Val Ala Gln
                275                 280                 285

Ile Lys Asp Gly Asn Arg Ser Ile Ile Gly Leu Met Ile Glu Ser Asn
                290                 295                 300

Ile His Glu Gly Asn Gln Ser Ser Glu Gln Pro Arg Ser Glu Met Lys
305                 310                 315                 320

Tyr Gly Val Ser Val Thr Asp Ala Cys Ile Ser Trp Glu Met Thr Asp
                325                 330                 335

Ala Leu Leu Arg Glu Ile His Gln Asp Leu Asn Gly Gln Leu Thr Ala
                340                 345                 350

Arg Val Ala
        355

<210> SEQ ID NO 46
<211> LENGTH: 500
<212> TYPE: DNA
<213> ORGANISM: Methylococcus capsulatus
<220> FEATURE:
<221> NAME/KEY: misc_feature
<223> OTHER INFORMATION: Pyrroloquinoline quinone biosynthesis protein A
      (ppqA) promoter gene - Methylococcus capsulatus str. Bath

<400> SEQUENCE: 46
```

```
ctcgctgctt cagggcagcg tcttcgccac ggaatacatc tatcgcgacc tgatgggcaa    60
tacgctcccg ccccagaaat gctcgtcgag aacggaagcc gaagccgccg catccgacga   120
ctacaacctc aaaaagcacg cccggatatt ctgtgaatcc cagggctatg ctggcatgt    180 cgaacagcgc aaaagtacgg gcaagctggt ctgcgaggaa tgcagcgaag gcggcgacaa   240
cggccgcttc cgctgccata tggaagacgt ggtcgtacag tgcaagcgga tcaaacccgg   300
ttctgtcggg ttgattccag gccagggctg aggggcccgc ctgacgttca ctgatgagcg   360
atacaagccg gcgtacggcc gctgtttcgg gaaaaactct gttgcgtagg agcggggcgg   420
tacgtatact ggctgccgag ctgtaacctg ctctttctct tgaagaccag acgtataaca   480
ttatctggag gacatttaag                                              500
```

<210> SEQ ID NO 47
<211> LENGTH: 549
<212> TYPE: DNA
<213> ORGANISM: Methylococcus capsulatus
<220> FEATURE:
<221> NAME/KEY: misc_feature
<223> OTHER INFORMATION: 3-hexulose-6-phosphate synthase (hps) promoter
      gene - Methylococcus capsulatus str. Bath

<400> SEQUENCE: 47

```
gctcggatta ttacctgttc ggcggcgtgg tcgccgccct catcggcttc gtgctctgga    60
gcagccgccg tccggccacc gcccacccgg ccgcaaccgc cgcagcggcc gccccgccg    120 ccgcaccggc gccggcagcc accggcgtcg ccaaatacct ccaggccaa  gggctcgcca   180 ccggccccga aaccggtgtc gccaaatacc tcaaggcgct gccggaaccc gtccgcaccc   240
ccgaaaccgg cgtggcccgc tacctcaaga acctgccact gcccgaagtg gctgccgccg   300
ccgaaaccgg tgtcgccagg tacatcaaga acctgcccaa gcccgccgtc gtggccacgg   360
gcgaaaccgg cgtcaccaag tacctgaaaa gcctcaacgg ctgaccctgc gaaaggggg   420 gctgcattga cagcggcccc ctcactcttt acagttggga aattgtgcgt ttagcaatac   480
cccataactc ctaaggctta agcccgactt ttttctctct accttacttt tttgatcgga   540
ggagatctc                                                          549
```

<210> SEQ ID NO 48
<211> LENGTH: 809
<212> TYPE: DNA
<213> ORGANISM: Methylococcus capsulatus
<220> FEATURE:
<221> NAME/KEY: misc_feature
<223> OTHER INFORMATION: Sigma 70 gene promoter gene - Methylococcus
      capsulatus str. Bath

<400> SEQUENCE: 48

```
tgcttcagat agcgggcggc cgtggcaccg ccataaccgc caccgacgac cacgacccgg    60
ccgcctgagc gaagaccctt gccggaagcg cagccaccca gtccccagcc catgccgcag   120
actgccagca ggcgcaggaa ccgccgccgg cggatcatgg cctcttttcc agaaagccgg   180
cgatcgcttc aatgtcctgg ttcgtgagtc cggcagcgat ccggttcatg accgtgcccg   240
atctttttcc ttcacggtac tcccgcaaca gagatgccat ctccttcgca tcgaagcggc   300
gtaacgatgc cggttcggga atctgctcct cctcgtcggc atggcagccg aggcaaccga   360
gcgcagccaa aaccatgtcc ggttttttcgg cccgggccgg gaaacagaga gcgacagcga   420
tcgtaccgat ctggacgcgt ctcacaaacg acaaaacgtc acgatgggtg ttcggtagct   480
```

| | | |
|---|---|---|
| gagtcacggg gatttgtaga agtataggac cgacggattt tatgcaagca tgtcgctttg | 540 | |
| accaagccgg gattccatgg aagggatgtc atcgggagag ttatttatgt cgttgattta | 600 | |
| taagaaacta cccctgcgtc aaaatgtcgc agatttttct tgacagtttg ggggagggtg | 660 | |
| atagactccc tccaccgatg gaccggtacc gcctctgttg cggggtccat gaaatgcccg | 720 | |
| ttagaggcag aaccgatagg gaattagaga agcgggcgtc ggcgccgaat gccggcccct | 780 | |
| gtcaaccatc actttaggag gaacaaaca | 809 | |

```
<210> SEQ ID NO 49
<211> LENGTH: 500
<212> TYPE: DNA
<213> ORGANISM: Methylococcus capsulatus
<220> FEATURE:
<221> NAME/KEY: misc_feature
<223> OTHER INFORMATION: Formaldehyde activating enzyme 2 (fae2)
      promoter gene - Methylococcus capsulatus str. Bath

<400> SEQUENCE: 49
```

| | | |
|---|---|---|
| caatacacct gcgactatac ggatgttttt gatttcatga ttccacgcta tcatagtgcg | 60 | |
| ctgtcccgat gggacaatga aggctgggcg gcggtggctg cgttttccgg catgcttgct | 120 | |
| cgcataccgg atagccacat cgaacgcaaa ttcgggcccc gctactcccc gtgggtatcg | 180 | |
| gagaagatgg tgctcctcga gaaaacgctg tcctatgccg tgcgacctga ttcggttttg | 240 | |
| gggcttctac gggacgtgga tgccgaattc aagacgcgcg gaattaaccc tggaacgact | 300 | |
| gccgacctga cggtcgccgg tctgctcgcc gtgcgcctgg aggcgatttt taccgggacg | 360 | |
| ggccggggtt aaaccttcgg cacgtgggg ccgatgcggg cactccgcga gaaacttcgg | 420 | |
| tctcgaaaac ctttcccggg ggaacaacca tgtccttatt aaaaaagttt ttttcgtttt | 480 | |
| tttcacaaga ggaaattcag | 500 | |

```
<210> SEQ ID NO 50
<211> LENGTH: 816
<212> TYPE: DNA
<213> ORGANISM: Artificial Sequence
<220> FEATURE:
<223> OTHER INFORMATION: Kanamycin Resistance (KanR) gene - from vector
      pCR2.1-TOPO (Ali and Murrell 2009)

<400> SEQUENCE: 50
```

| | | |
|---|---|---|
| atgagccata ttcaacggga aacgtcttgc tcgaggccgc gattaaattc caacatggat | 60 | |
| gctgatttat atgggtataa atgggctcgc gataatgtcg ggcaatcagg tgcgacaatc | 120 | |
| tatcgattgt atgggaagcc cgatgcgcca gagttgtttc tgaaacatgg caaaggtagc | 180 | |
| gttgccaatg atgttacaga tgagatggtc agactaaact ggctgacgga atttatgcct | 240 | |
| cttccgacca tcaagcattt tatccgtact cctgatgatg catggttact caccactgcg | 300 | |
| atccccggga aaacagcatt ccaggtatta gaagaatatc ctgattcagg tgaaaatatt | 360 | |
| gttgatgcgc tggcagtgtt cctgcgccgg ttgcattcga ttcctgtttg taattgtcct | 420 | |
| tttaacagcg atcgcgtatt tcgtctcgct caggcgcaat cacgaatgaa taacggtttg | 480 | |
| gttgatgcga gtgattttga tgacgagcgt aatggctggc ctgttgaaca agtctggaaa | 540 | |
| gaaatgcata agcttttgcc attctcaccg gattcagtcg tcactcatgg tgatttctca | 600 | |
| cttgataacc ttatttttga cgaggggaaa ttaataggtt gtattgatgt tggacgagtc | 660 | |
| ggaatcgcag accgatacca ggatcttgcc atcctatgga actgcctcgg tgagttttct | 720 | |
| ccttcattac agaaacggct ttttcaaaaa tatggtattg ataatcctga tatgaataaa | 780 | | ttgcagtttc atttgatgct cgatgagttt ttctaa 816

<210> SEQ ID NO 51
<211> LENGTH: 271
<212> TYPE: PRT
<213> ORGANISM: Artificial Sequence
<220> FEATURE:
<223> OTHER INFORMATION: Kanamycin Resistance (KanR) protein

<400> SEQUENCE: 51

```
Met Ser His Ile Gln Arg Glu Thr Ser Cys Ser Arg Pro Arg Leu Asn
1               5                   10                  15

Ser Asn Met Asp Ala Asp Leu Tyr Gly Tyr Lys Trp Ala Arg Asp Asn
            20                  25                  30

Val Gly Gln Ser Gly Ala Thr Ile Tyr Arg Leu Tyr Gly Lys Pro Asp
        35                  40                  45

Ala Pro Glu Leu Phe Leu Lys His Gly Lys Gly Ser Val Ala Asn Asp
    50                  55                  60

Val Thr Asp Glu Met Val Arg Leu Asn Trp Leu Thr Glu Phe Met Pro
65                  70                  75                  80

Leu Pro Thr Ile Lys His Phe Ile Arg Thr Pro Asp Asp Ala Trp Leu
                85                  90                  95

Leu Thr Thr Ala Ile Pro Gly Lys Thr Ala Phe Gln Val Leu Glu Glu
            100                 105                 110

Tyr Pro Asp Ser Gly Glu Asn Ile Val Asp Ala Leu Ala Val Phe Leu
        115                 120                 125

Arg Arg Leu His Ser Ile Pro Val Cys Asn Cys Pro Phe Asn Ser Asp
    130                 135                 140

Arg Val Phe Arg Leu Ala Gln Ala Gln Ser Arg Met Asn Asn Gly Leu
145                 150                 155                 160

Val Asp Ala Ser Asp Phe Asp Asp Glu Arg Asn Gly Trp Pro Val Glu
                165                 170                 175

Gln Val Trp Lys Glu Met His Lys Leu Leu Pro Phe Ser Pro Asp Ser
            180                 185                 190

Val Val Thr His Gly Asp Phe Ser Leu Asp Asn Leu Ile Phe Asp Glu
        195                 200                 205

Gly Lys Leu Ile Gly Cys Ile Asp Val Gly Arg Val Gly Ile Ala Asp
    210                 215                 220

Arg Tyr Gln Asp Leu Ala Ile Leu Trp Asn Cys Leu Gly Glu Phe Ser
225                 230                 235                 240

Pro Ser Leu Gln Lys Arg Leu Phe Gln Lys Tyr Gly Ile Asp Asn Pro
                245                 250                 255

Asp Met Asn Lys Leu Gln Phe His Leu Met Leu Asp Glu Phe Phe
            260                 265                 270
```

<210> SEQ ID NO 52
<211> LENGTH: 589
<212> TYPE: DNA
<213> ORGANISM: Artificial Sequence
<220> FEATURE:
<223> OTHER INFORMATION: ColE1 plasmid Ori - from pUC18/19 vector (Ali
      and Murrell 2009)

<400> SEQUENCE: 52
tttccatagg ctccgccccc ctgacgagca tcacaaaaat cgacgctcaa gtcagaggtg    60
gcgaaacccg acaggactat aaagatacca ggcgtttccc cctggaagct ccctcgtgcg   120
ctctcctgtt ccgaccctgc cgcttaccgg atacctgtcc gcctttctcc cttcgggaag   180

```
cgtggcgctt tctcatagct cacgctgtag gtatctcagt tcggtgtagg tcgttcgctc      240
caagctgggc tgtgtgcacg aaccccccgt tcagcccgac cgctgcgcct tatccggtaa      300
ctatcgtctt gagtccaacc cggtaagaca cgacttatcg ccactggcag cagccactgg      360
taacaggatt agcagagcga ggtatgtagg cggtgctaca gagttcttga agtggtggcc      420
taactacggc tacactagaa ggacagtatt tggtatctgc gctctgctga agccagttac      480
cttcggaaaa agagttggta gctcttgatc cggcaaacaa accaccgctg gtagcggtgg      540
tttttttgtt tgcaagcagc agattacgcg cagaaaaaaa ggatctcaa               589

<210> SEQ ID NO 53
<211> LENGTH: 110
<212> TYPE: DNA
<213> ORGANISM: Artificial Sequence
<220> FEATURE:
<223> OTHER INFORMATION: OriT (origin of transfer) - from pMJ153 vector
      (Ali and Murrell 2009)

<400> SEQUENCE: 53
gggcaggata ggtgaagtag gcccacccgc gagcgggtgt tccttcttca ctgtcccgtta      60 ttcgcacctg gcggtgctca acgggaatcc tgctctgcga ggctggccgg                110

<210> SEQ ID NO 54
<211> LENGTH: 632
<212> TYPE: DNA
<213> ORGANISM: Artificial Sequence
<220> FEATURE:
<223> OTHER INFORMATION: OriV (origin of replication)

<400> SEQUENCE: 54
agcgggccgg gagggttcga gaagggggg caccccccctt cggcgtgcgc ggtcacgcgc      60
acagggcgca gccctggtta aaaacaaggt ttataaatat tggtttaaaa gcaggttaaa     120
agacaggtta gcggtggccg aaaaacgggc ggaaaccctt gcaaatgctg gatttttctgc    180 ctgtggacag cccctcaaat gtcaataggt gcgcccctca tctgtcagca ctctgcccct    240
caagtgtcaa ggatcgcgcc cctcatctgt cagtagtcgc gcccctcaag tgtcaatacc    300
gcagggcact tatccccagg cttgtccaca tcatctgtgg gaaactcgcg taaaatcagg    360
cgttttcgcc gatttgcgag gctggccagc tccacgtcgc cggccgaaat cgagcctgcc    420
cctcatctgt caacgccgcg ccgggtgagt cggcccctca agtgtcaacg tccgcccctc    480
atctgtcagt gagggccaag ttttccgcga ggtatccaca acgccggcgg ccgcggtgtc    540
tcgcacacgg cttcgacggc gtttctggcg cgtttgcagg gccatagacg gccgccagcc    600
cagcggcgag ggcaaccagc ccggtgagcg tc                                 632

<210> SEQ ID NO 55
<211> LENGTH: 372
<212> TYPE: DNA
<213> ORGANISM: Escherichia coli

<400> SEQUENCE: 55
atggctgatg aaaccaagcc aaccaggaag ggcagcccac ctatcaaggt gtactgcctt      60
ccagacgaac gaagagcgat tgaggaaaag gcggcggcgg ccggcatgag cctgtaggcc     120
tacctgctgg ccgtcggcca gggctacaaa atcacgggcg tcgtggacta tgagcacgtc     180
cgcgagctgg cccgcatcaa tggcgacctg ggccgcctgg gcggcctgct gaaactctgg     240
ctcaccgacg acccgcgcac ggcgcggttc ggtgatgcca cgatcctcgc cctgctggcg     300
```

-continued

```
aagatcgaag agaagcagga cgagcttggc aaggtcatga tgggcgtggt ccgcccgagg    360
gcagagccat ga                                                        372
```

<210> SEQ ID NO 56
<211> LENGTH: 122
<212> TYPE: PRT
<213> ORGANISM: Escherichia coli
<220> FEATURE:
<221> NAME/KEY: MOD_RES
<222> LOCATION: (1)..(122)
<223> OTHER INFORMATION: TnaA Gene- Escherichia coli strain K-12 (XL1-
      Blue/S17-1)

<400> SEQUENCE: 56

```
Met Ala Asp Glu Thr Lys Pro Thr Arg Lys Gly Ser Pro Pro Ile Lys
1               5                   10                  15

Val Tyr Cys Leu Pro Asp Glu Arg Arg Ala Ile Glu Glu Lys Ala Ala
                20                  25                  30

Ala Ala Gly Met Ser Leu Ala Tyr Leu Leu Ala Val Gly Gln Gly Tyr
            35                  40                  45

Lys Ile Thr Gly Val Val Asp Tyr Glu His Val Arg Glu Leu Ala Arg
    50                  55                  60

Ile Asn Gly Asp Leu Gly Arg Leu Gly Gly Leu Leu Lys Leu Trp Leu
65                  70                  75                  80

Thr Asp Asp Pro Arg Thr Ala Arg Phe Gly Asp Ala Thr Ile Leu Ala
                85                  90                  95

Leu Leu Ala Lys Ile Glu Glu Lys Gln Asp Glu Leu Gly Lys Val Met
            100                 105                 110

Met Gly Val Val Arg Pro Arg Ala Glu Pro
        115                 120
```

<210> SEQ ID NO 57
<211> LENGTH: 1149
<212> TYPE: DNA
<213> ORGANISM: Escherichia coli

<400> SEQUENCE: 57

```
atgaatcgga cgtttgaccg gaaggcatac aggcaagaac tgatcgacgc ggggttttcc    60
gccgaggatg ccgaaaccat cgcaagccgc accgtcatgc gtgcgccccg cgaaaccttc    120
cagtccgtcg gctcgatggt ccagcaagct acggccaaga tcgagcgcga cagcgtgcaa    180
ctggctcccc ctgccctgcc cgcgccatcg gccgccgtgg agcgttcgcg tcgtctcgaa    240
caggaggcgg caggtttggc gaagtcgatg accatcgaca cgcgaggaac tatgacgacc    300
aagaagcgaa aaccgccgg cgaggacctg caaaacagg tcagcgaggc caagcaggcc    360
gcgttgctga acacacgaa gcagcagatc aaggaaatgc agctttcctt gttcgatatt    420
gcgccgtggc cggacacgat gcgagcgatg ccaaacgaca cggcccgctc tgccctgttc    480
accacgcgca acaagaaaat cccgcgcgag gcgctgcaaa acaaggtcat tttccacgtc    540
aacaaggacg tgaagatcac ctacaccggc gtcgagctgc gggccgacga tgacgaactg    600
gtgtggcagc aggtgttgga gtacgcgaag cgcaccccta tcggcgagcc gatcaccttc    660
acgttctacg agctttgcca ggacctgggc tggtcgatca atggccggta ttacacgaag    720
gccgaggaat gcctgtcgcg cctacaggcg acggcgatgg gcttcacgtc cgaccgcgtt    780
gggcacctgg aatcggtgtc gctgctgcac cgcttccgcg tcctggaccg tggcaagaaa    840
acgtcccgtt gccaggtcct gatcgacgag gaaatcgtcg tgctgtttgc tggcgaccac    900
```

```
tacacgaaat tcatatggga gaagtaccgc aagctgtcgc cgacggcccg acggatgttc    960
gactatttca gctcgcaccg ggagccgtac ccgctcaagc tggaaacctt ccgcctcatg   1020
tgcggatcgg attccacccg cgtgaagaag tggcgcgagc aggtcggcga agcctgcgaa   1080
gagttgcgag gcagcggcct ggtggaacac gcctgggtca atgatgacct ggtgcattgc   1140
aaacgctag                                                           1149
```

```
<210> SEQ ID NO 58
<211> LENGTH: 382
<212> TYPE: PRT
<213> ORGANISM: Escherichia coli

<400> SEQUENCE: 58

Met Asn Arg Thr Phe Asp Arg Lys Ala Tyr Arg Gln Glu Leu Ile Asp
1               5                   10                  15

Ala Gly Phe Ser Ala Glu Asp Ala Glu Thr Ile Ala Ser Arg Thr Val
                20                  25                  30

Met Arg Ala Pro Arg Glu Thr Phe Gln Ser Val Gly Ser Met Val Gln
            35                  40                  45

Gln Ala Thr Ala Lys Ile Glu Arg Asp Ser Val Gln Leu Ala Pro Pro
    50                  55                  60

Ala Leu Pro Ala Pro Ser Ala Ala Val Glu Arg Ser Arg Arg Leu Glu
65                  70                  75                  80

Gln Glu Ala Ala Gly Leu Ala Lys Ser Met Thr Ile Asp Thr Arg Gly
                85                  90                  95

Thr Met Thr Thr Lys Lys Arg Lys Thr Ala Gly Glu Asp Leu Ala Lys
            100                 105                 110

Gln Val Ser Glu Ala Lys Gln Ala Ala Leu Leu Lys His Thr Lys Gln
        115                 120                 125

Gln Ile Lys Glu Met Gln Leu Ser Leu Phe Asp Ile Ala Pro Trp Pro
    130                 135                 140

Asp Thr Met Arg Ala Met Pro Asn Asp Thr Ala Arg Ser Ala Leu Phe
145                 150                 155                 160

Thr Thr Arg Asn Lys Lys Ile Pro Arg Glu Ala Leu Gln Asn Lys Val
                165                 170                 175

Ile Phe His Val Asn Lys Asp Val Lys Ile Thr Tyr Thr Gly Val Glu
            180                 185                 190

Leu Arg Ala Asp Asp Glu Leu Val Trp Gln Gln Val Leu Glu Tyr
        195                 200                 205

Ala Lys Arg Thr Pro Ile Gly Glu Pro Ile Thr Phe Thr Phe Tyr Glu
    210                 215                 220

Leu Cys Gln Asp Leu Gly Trp Ser Ile Asn Gly Arg Tyr Tyr Thr Lys
225                 230                 235                 240

Ala Glu Glu Cys Leu Ser Arg Leu Gln Ala Thr Ala Met Gly Phe Thr
                245                 250                 255

Ser Asp Arg Val Gly His Leu Glu Ser Val Ser Leu His Arg Phe
            260                 265                 270

Arg Val Leu Asp Arg Gly Lys Lys Thr Ser Arg Cys Gln Val Leu Ile
        275                 280                 285

Asp Glu Glu Ile Val Val Leu Phe Ala Gly Asp His Tyr Thr Lys Phe
    290                 295                 300

Ile Trp Glu Lys Tyr Arg Lys Leu Ser Pro Thr Ala Arg Arg Met Phe
305                 310                 315                 320
```

Asp Tyr Phe Ser Ser His Arg Glu Pro Tyr Pro Leu Lys Leu Glu Thr
                325                 330                 335

Phe Arg Leu Met Cys Gly Ser Asp Ser Thr Arg Val Lys Lys Trp Arg
            340                 345                 350

Glu Gln Val Gly Glu Ala Cys Glu Leu Arg Gly Ser Gly Leu Val
        355                 360                 365

Glu His Ala Trp Val Asn Asp Leu Val His Cys Lys Arg
    370                 375                 380

<210> SEQ ID NO 59
<211> LENGTH: 1194
<212> TYPE: DNA
<213> ORGANISM: Escherichia coli

<400> SEQUENCE: 59
gtgtttcaaa aagttgacgc ctacgctggc gacccgattc ttacgcttat ggagcgtttt      60
aaagaagacc ctcgcagcga caaagtgaat ttaagtatcg gtctgtacta caacgaagac     120
ggaattattc cacaactgca agccgtggcg gaggcggaag cgcgcctgaa tgcgcagcct     180
catggcgctt cgctttattt accgatggaa gggcttaact gctatcgcca tgccattgcg     240
ccgctgctgt ttggtgcgga ccatccggta ctgaaacaac agcgcgtagc aaccattcaa     300
acccttggcg gctccggggc attgaaagtg ggcgcggatt tcctgaaacg ctacttcccg     360
gaatcaggcg tctgggtcag cgatcctacc tgggaaaacc acgtagcaat attcgccggg     420
gctggattcg aagtgagtac ttaccccctgg tatgacgaag cgactaacgg cgtgcgcttt     480
aatgacctgt tggcgacgct gaaaacatta cctgcccgca gtattgtgtt gctgcatcca     540
tgttgccaca acccaacggg tgccgatctc actaatgatc agtgggatgc ggtgattgaa     600
attctcaaag cccgcgagct tattccattc ctcgatattg cctatcaagg atttggtgcc     660
ggtatggaag aggatgccta cgctattcgc gccattgcca gcgctggatt accccgctctg     720 gtgagcaatt cgttctcgaa aattttctcc ctttacggcg agcgcgtcgg cggactttct     780
gttatgtgtg aagatgccga agccgctggc cgcgtactgg ggcaattgaa agcaacagtt     840
cgccgcaact actccagccc gccgaatttt ggtgcgcagg tggtggctgc agtgctgaat     900
gacgaggcat tgaaagccag ctggctggcg gaagtagaag agatgcgtac tcgcattctg     960
gcaatgcgtc aggaattggt gaaggtatta agcacagaga tgccagaacg caatttcgat    1020
tatctgctta atcagcgcgg catgttcagt tataccggtt taagtgccgc tcaggttgac    1080
cgactacgtg aagaatttgg tgtctatctc atcgccagcg gtcgcatgtg tgtcgccggg    1140
ttaaatacgg caaatgtaca acgtgtggca aaggcgtttg ctgcggtgat gtaa         1194

<210> SEQ ID NO 60
<211> LENGTH: 397
<212> TYPE: PRT
<213> ORGANISM: Escherichia coli

<400> SEQUENCE: 60

Met Phe Gln Lys Val Asp Ala Tyr Ala Gly Asp Pro Ile Leu Thr Leu
1               5                   10                  15

Met Glu Arg Phe Lys Glu Asp Pro Arg Ser Asp Lys Val Asn Leu Ser
            20                  25                  30

Ile Gly Leu Tyr Tyr Asn Glu Asp Gly Ile Ile Pro Gln Leu Gln Ala
        35                  40                  45

Val Ala Glu Ala Glu Ala Arg Leu Asn Ala Gln Pro His Gly Ala Ser
    50                  55                  60

```
Leu Tyr Leu Pro Met Glu Gly Leu Asn Cys Tyr Arg His Ala Ile Ala
 65              70                  75                  80

Pro Leu Leu Phe Gly Ala Asp His Pro Val Leu Lys Gln Gln Arg Val
                 85                  90                  95

Ala Thr Ile Gln Thr Leu Gly Gly Ser Gly Ala Leu Lys Val Gly Ala
            100                 105                 110

Asp Phe Leu Lys Arg Tyr Phe Pro Glu Ser Gly Val Trp Val Ser Asp
            115                 120                 125

Pro Thr Trp Glu Asn His Val Ala Ile Phe Ala Gly Ala Gly Phe Glu
130                 135                 140

Val Ser Thr Tyr Pro Trp Tyr Asp Glu Ala Thr Asn Gly Val Arg Phe
145                 150                 155                 160

Asn Asp Leu Leu Ala Thr Leu Lys Thr Leu Pro Ala Arg Ser Ile Val
                165                 170                 175

Leu Leu His Pro Cys Cys His Asn Pro Thr Gly Ala Asp Leu Thr Asn
                180                 185                 190

Asp Gln Trp Asp Ala Val Ile Glu Ile Leu Lys Ala Arg Glu Leu Ile
            195                 200                 205

Pro Phe Leu Asp Ile Ala Tyr Gln Gly Phe Gly Ala Gly Met Glu Glu
            210                 215                 220

Asp Ala Tyr Ala Ile Arg Ala Ile Ala Ser Ala Gly Leu Pro Ala Leu
225                 230                 235                 240

Val Ser Asn Ser Phe Ser Lys Ile Phe Ser Leu Tyr Gly Glu Arg Val
                245                 250                 255

Gly Gly Leu Ser Val Met Cys Glu Asp Ala Glu Ala Ala Gly Arg Val
            260                 265                 270

Leu Gly Gln Leu Lys Ala Thr Val Arg Arg Asn Tyr Ser Ser Pro Pro
            275                 280                 285

Asn Phe Gly Ala Gln Val Val Ala Ala Val Leu Asn Asp Glu Ala Leu
            290                 295                 300

Lys Ala Ser Trp Leu Ala Glu Val Glu Glu Met Arg Thr Arg Ile Leu
305                 310                 315                 320

Ala Met Arg Gln Glu Leu Val Lys Val Leu Ser Thr Glu Met Pro Glu
                325                 330                 335

Arg Asn Phe Asp Tyr Leu Leu Asn Gln Arg Gly Met Phe Ser Tyr Thr
            340                 345                 350

Gly Leu Ser Ala Ala Gln Val Asp Arg Leu Arg Glu Glu Phe Gly Val
            355                 360                 365

Tyr Leu Ile Ala Ser Gly Arg Met Cys Val Ala Gly Leu Asn Thr Ala
            370                 375                 380

Asn Val Gln Arg Val Ala Lys Ala Phe Ala Ala Val Met
385                 390                 395
```